United States Patent
Walsh et al.

(10) Patent No.: US 11,673,967 B2
(45) Date of Patent: *Jun. 13, 2023

(54) STABILIZED FORMULATIONS CONTAINING ANTI-PCSK9 ANTIBODIES

(71) Applicant: Regeneron Pharmaceuticals, Inc., Tarrytown, NY (US)

(72) Inventors: Scott M. Walsh, Sewickley, PA (US); Daniel B. Dix, Lagrangeville, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 305 days.

This patent is subject to a terminal disclaimer.

(21) Appl. No.: 16/930,595

(22) Filed: Jul. 16, 2020

(65) Prior Publication Data

US 2021/0054100 A1 Feb. 25, 2021

Related U.S. Application Data

(63) Continuation of application No. 16/384,298, filed on Apr. 15, 2019, now Pat. No. 10,752,701, which is a continuation of application No. 15/603,732, filed on May 24, 2017, now Pat. No. 10,472,425, which is a continuation of application No. 14/918,109, filed on Oct. 20, 2015, now abandoned, which is a continuation of application No. 14/319,730, filed on Jun. 30, 2014, now Pat. No. 9,193,801, which is a continuation of application No. 13/559,862, filed on Jul. 27, 2012, now Pat. No. 8,795,669.

(60) Provisional application No. 61/512,666, filed on Jul. 28, 2011.

(51) Int. Cl.
| | | |
|---|---|---|
| C07K 16/40 | (2006.01) | |
| A61K 39/395 | (2006.01) | |
| A61K 47/22 | (2006.01) | |
| A61K 47/26 | (2006.01) | |
| A61M 5/315 | (2006.01) | |
| A61M 5/32 | (2006.01) | |

(52) U.S. Cl.
CPC .......... *C07K 16/40* (2013.01); *A61K 39/3955* (2013.01); *A61K 39/39591* (2013.01); *A61K 47/22* (2013.01); *A61K 47/26* (2013.01); *A61M 5/31513* (2013.01); *A61M 5/3202* (2013.01); *C07K 2317/565* (2013.01); *C07K 2317/94* (2013.01)

(58) Field of Classification Search
CPC ............. C07K 16/40; C07K 2317/565; C07K 2317/94; A61K 39/395; A61K 39/3955; A61K 39/39591; A61K 2039/505; A61M 5/31513; A61M 5/3202; A61M 5/3287; A61M 2202/04

See application file for complete search history.

(56) References Cited

U.S. PATENT DOCUMENTS

| | | |
|---|---|---|
| 4,997,423 A | 3/1991 | Okuda et al. |
| 5,016,784 A | 5/1991 | Batson |
| 5,260,440 A | 11/1993 | Hirai et al. |
| 5,273,995 A | 12/1993 | Roth |
| 5,399,670 A | 3/1995 | Bhattacharya et al. |
| 5,480,796 A | 1/1996 | Kishimoto |
| 5,670,373 A | 9/1997 | Kishimoto |
| 5,723,120 A | 3/1998 | Brackenhoff et al. |
| 5,795,965 A | 8/1998 | Tsuchiya |
| 5,817,790 A | 10/1998 | Tsuchiya |
| 5,851,999 A | 12/1998 | Ullrich et al. |
| 5,888,510 A | 3/1999 | Kishimoto |
| 5,888,511 A | 3/1999 | Skurkovich et al. |
| 5,908,686 A | 6/1999 | Sudo et al. |
| 5,939,598 A | 8/1999 | Kucherlapati et al. |
| 6,011,003 A | 1/2000 | Charnock-Jones et al. |
| 6,086,874 A | 7/2000 | Yoshida et al. |
| 6,171,586 B1 | 1/2001 | Lam et al. |
| 6,261,560 B1 | 7/2001 | Tsujinaka et al. |
| 6,267,958 B1 | 7/2001 | Andya et al. |
| 6,270,993 B1 | 8/2001 | Shibuya et al. |
| 6,286,699 B1 | 9/2001 | Sudo |
| 6,410,691 B1 | 6/2002 | Kishimoto |
| 6,596,541 B2 | 7/2003 | Murphy et al. |

(Continued)

FOREIGN PATENT DOCUMENTS

| | | |
|---|---|---|
| CN | 101489565 A | 7/2009 |
| CN | 103476797 A | 12/2013 |

(Continued)

OTHER PUBLICATIONS

U.S. Appl. No. 16/384,298, filed Apr. 15, 2019, 2019/0284301, Sep. 19, 2019, U.S. Pat. No. 10,752,701, Aug. 25, 2020, Scott M. Walsh.
U.S. Appl. No. 15/603,732, filed May 24, 2017, 2018/0044436, Feb. 15, 2018, U.S. Pat. No. 10,472,425, Nov. 12, 2019, Scott M. Walsh.
U.S. Appl. No. 14/319,730, filed Jun. 30, 2014, 2014/0341928, Nov. 20, 2014, U.S. Pat. No. 9,193,801, Nov. 24, 2015, Scott M. Walsh.
U.S. Appl. No. 13/559,862, filed Jul. 27, 2012, 2013/0189277, Jul. 25, 2013, U.S. Pat. No. 8,795,669, Aug. 5, 2014, Scott M. Walsh.
(Jan. 1, 2015) "PRALUENT® (Alirocumab), Highlights of Prescribing Information", United States Food and Drug Administration, Retrieved from: <<https://www.accessdata.fda.gov/drugsatfda_docs/label/2015/125559orig1s000lbledt.pdf>>, 48 Pages.

(Continued)

*Primary Examiner* — Vanessa L. Ford
*Assistant Examiner* — Sandra Dillahunt
(74) *Attorney, Agent, or Firm* — Lathrop GPM LLP; James H. Velema; James V. DeGiulio

(57) ABSTRACT

The present invention provides pharmaceutical formulations comprising a human antibody that specifically binds to human proprotein convertase subtilisin/kexin type 9 (PCSK9). The formulations may contain, in addition to an anti-PCSK9 antibody, at least one amino acid, at least one sugar, or at least one non-ionic surfactant. The pharmaceutical formulations of the present invention exhibit a substantial degree of antibody stability after storage for several months.

3 Claims, No Drawings

Specification includes a Sequence Listing.

(56) References Cited

U.S. PATENT DOCUMENTS

| | | |
|---|---|---|
| 6,629,949 B1 | 10/2003 | Douglas |
| 6,632,927 B2 | 10/2003 | Adair |
| 6,645,635 B2 | 11/2003 | Muraki |
| 6,659,982 B2 | 12/2003 | Douglas et al. |
| 6,670,373 B1 | 12/2003 | Bonjouklian et al. |
| 6,692,742 B1 | 2/2004 | Nakamura et al. |
| 6,723,319 B1 | 4/2004 | Ito |
| 6,875,432 B2 | 4/2005 | Shire |
| 6,946,548 B2 | 9/2005 | Sarkar et al. |
| 7,001,892 B1 | 2/2006 | Chmielewski et al. |
| 7,029,895 B2 | 4/2006 | Glucksmann et al. |
| 7,060,268 B2 | 6/2006 | Andya et al. |
| 7,129,338 B1 | 10/2006 | Ota et al. |
| 7,226,554 B2 | 6/2007 | Sudo et al. |
| 7,300,754 B2 | 11/2007 | Abi et al. |
| 7,320,792 B2 | 1/2008 | Ito et al. |
| 7,479,543 B2 | 1/2009 | Tsuchiya et al. |
| 7,482,147 B2 | 1/2009 | Kapeller-Libermann et al. |
| 7,572,618 B2 | 8/2009 | Mintier et al. |
| 7,608,693 B2 | 10/2009 | Martin et al. |
| 7,754,208 B2 | 7/2010 | Ledbetter et al. |
| 8,030,457 B2 | 10/2011 | Jackson et al. |
| 8,062,640 B2 | 11/2011 | Sleeman et al. |
| 8,080,243 B2 | 12/2011 | Liang et al. |
| 8,092,803 B2 | 1/2012 | Furfine et al. |
| 8,168,762 B2 | 5/2012 | Jackson et al. |
| 8,188,233 B2 | 5/2012 | Condra et al. |
| 8,188,234 B2 | 5/2012 | Condra et al. |
| 8,192,741 B2 | 6/2012 | Radin et al. |
| 8,357,371 B2 | 1/2013 | Sleeman et al. |
| 8,440,890 B1 | 5/2013 | Carlone, Jr. |
| 8,501,184 B2 | 8/2013 | Sleeman et al. |
| 8,748,115 B2 | 6/2014 | Yanni et al. |
| 8,795,669 B2 | 8/2014 | Walsh et al. |
| 8,829,165 B2 | 9/2014 | Jackson et al. |
| 8,869,904 B2 | 10/2014 | Jani |
| 8,883,157 B1 | 11/2014 | Clube |
| 8,945,560 B1 | 2/2015 | Clube |
| 9,034,332 B1 | 5/2015 | Clube |
| 9,120,851 B2 | 9/2015 | Sleeman et al. |
| 9,127,068 B2 | 9/2015 | Okamoto et al. |
| 9,173,880 B2 | 11/2015 | Dix et al. |
| 9,193,801 B2 | 11/2015 | Walsh et al. |
| 9,358,287 B2 | 6/2016 | Harp et al. |
| 9,540,449 B2 | 1/2017 | Yancopoulos et al. |
| 9,550,837 B2 | 1/2017 | Sleeman et al. |
| 9,561,155 B2 | 2/2017 | Hanotin et al. |
| 9,682,013 B2 | 6/2017 | Hanotin et al. |
| 9,724,411 B2 | 8/2017 | Sleeman et al. |
| 9,884,916 B2 | 2/2018 | Stevens et al. |
| 10,023,654 B2 | 7/2018 | Sleeman et al. |
| 10,023,657 B2 | 7/2018 | Leuscher et al. |
| 10,072,086 B2 | 9/2018 | Dix et al. |
| 10,076,571 B2 | 9/2018 | Swergold et al. |
| 10,111,953 B2 | 10/2018 | Swergold et al. |
| 10,428,157 B2 | 10/2019 | Baccara-Dinet et al. |
| 10,472,425 B2 | 11/2019 | Walsh et al. |
| 10,494,442 B2 | 12/2019 | Sasiela et al. |
| 10,544,232 B2 | 1/2020 | Baccara-Dinet et al. |
| 10,752,701 B2 | 8/2020 | Walsh et al. |
| 10,772,956 B2 | 9/2020 | Pordy et al. |
| 10,927,435 B2 | 2/2021 | Huang et al. |
| 10,941,210 B2 | 3/2021 | Sleeman et al. |
| 10,995,150 B2 | 5/2021 | Sasiela et al. |
| 11,116,839 B2 | 9/2021 | Swergold et al. |
| 11,246,925 B2 | 2/2022 | Hanotin et al. |
| 11,306,155 B2 | 4/2022 | Baccara-Dinet et al. |
| 2002/0187150 A1 | 12/2002 | Mihara et al. |
| 2003/0092606 A1 | 5/2003 | L'Italien et al. |
| 2003/0113316 A1 | 6/2003 | Kaisheva et al. |
| 2003/0118592 A1 | 6/2003 | Ledbetter et al. |
| 2003/0133939 A1 | 7/2003 | Ledbetter et al. |
| 2004/0071706 A1 | 4/2004 | Ito et al. |
| 2004/0101920 A1 | 5/2004 | Radziejewski et al. |
| 2004/0115197 A1 | 6/2004 | Yoshizaki et al. |
| 2004/0197324 A1 | 10/2004 | Liu et al. |
| 2004/0219156 A1 | 11/2004 | Goldenberg et al. |
| 2005/0142635 A1 | 6/2005 | Tsuchiya et al. |
| 2005/0238644 A1 | 10/2005 | Mihara et al. |
| 2005/0281831 A1 | 12/2005 | Davis-Smyth et al. |
| 2006/0078531 A1 | 4/2006 | Sota |
| 2006/0078532 A1 | 4/2006 | Omoigui |
| 2006/0078533 A1 | 4/2006 | Omoigui |
| 2006/0147945 A1 | 7/2006 | Edmonds et al. |
| 2006/0177436 A1 | 8/2006 | Ghilardi et al. |
| 2006/0251653 A1 | 11/2006 | Okuda et al. |
| 2006/0275294 A1 | 12/2006 | Omoigui |
| 2006/0292147 A1 | 12/2006 | Yoshizaki et al. |
| 2007/0036785 A1 | 2/2007 | Kishimoto et al. |
| 2007/0036788 A1 | 2/2007 | Sheriff et al. |
| 2007/0082345 A1 | 4/2007 | Ota et al. |
| 2007/0098714 A1 | 5/2007 | Nishimoto et al. |
| 2007/0148169 A1 | 6/2007 | Yoshizaki et al. |
| 2007/0224663 A1 | 9/2007 | Rosen et al. |
| 2008/0008697 A1 | 1/2008 | Mintier et al. |
| 2008/0124325 A1 | 5/2008 | Ito et al. |
| 2008/0131374 A1 | 6/2008 | Medich et al. |
| 2008/0145367 A1 | 6/2008 | Bove et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann et al. |
| 2009/0318536 A1 | 12/2009 | Freier et al. |
| 2009/0326202 A1 | 12/2009 | Jackson et al. |
| 2010/0004061 A1 | 2/2010 | Sitlani et al. |
| 2010/0040611 A1 | 2/2010 | Sparrow et al. |
| 2010/0041102 A1 | 2/2010 | Sitlani et al. |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166468 A1 | 7/2010 | Tamaki |
| 2010/0166768 A1 | 7/2010 | Sleeman et al. |
| 2010/0216667 A1 | 8/2010 | Meyer et al. |
| 2010/0233177 A1 | 9/2010 | Yowe et al. |
| 2011/0009628 A1 | 1/2011 | Liu et al. |
| 2011/0015252 A1 | 1/2011 | Fitzgerald et al. |
| 2011/0027287 A1 | 2/2011 | Jackson et al. |
| 2011/0033465 A1 | 2/2011 | Hedrick et al. |
| 2011/0065902 A1 | 3/2011 | Sleeman et al. |
| 2011/0098450 A1 | 4/2011 | Igawa et al. |
| 2011/0111406 A1 | 5/2011 | Igawa et al. |
| 2011/0142849 A1 | 6/2011 | Rue et al. |
| 2011/0171241 A1 | 7/2011 | Dix et al. |
| 2011/0229489 A1 | 9/2011 | Pons et al. |
| 2011/0230542 A1 | 9/2011 | Tan et al. |
| 2011/0245473 A1 | 10/2011 | Igawa et al. |
| 2011/0256148 A1 | 10/2011 | Sleeman et al. |
| 2011/0313024 A1 | 12/2011 | Beigelman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0097565 A1 | 4/2012 | Dix et al. |
| 2012/0122954 A1 | 5/2012 | Staarup et al. |
| 2012/0195910 A1 | 8/2012 | Wu et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2013/0011866 A1 | 1/2013 | Igawa et al. |
| 2013/0014958 A1 | 1/2013 | Jani |
| 2013/0064825 A1 | 3/2013 | Chan et al. |
| 2013/0064834 A1 | 3/2013 | Sleeman et al. |
| 2013/0071405 A1 | 3/2013 | Davies et al. |
| 2013/0085266 A1 | 4/2013 | Sleeman et al. |
| 2013/0115223 A1 | 5/2013 | Sparrow et al. |
| 2013/0189277 A1 | 7/2013 | Walsh et al. |
| 2013/0243784 A1 | 9/2013 | Swergold |

(56) References Cited

U.S. PATENT DOCUMENTS

| | | |
|---|---|---|
| 2013/0245235 A1 | 9/2013 | Jackson et al. |
| 2014/0004122 A1 | 1/2014 | Chan et al. |
| 2014/0030270 A1 | 1/2014 | Clogston et al. |
| 2014/0044730 A1 | 2/2014 | Yancopoulos et al. |
| 2014/0065649 A1 | 3/2014 | Schafer et al. |
| 2014/0099312 A1 | 4/2014 | Sleeman et al. |
| 2014/0154262 A1 | 6/2014 | Hanotin et al. |
| 2014/0161821 A1 | 6/2014 | Udata |
| 2014/0178402 A1 | 6/2014 | Hanotin et al. |
| 2014/0341928 A1 | 11/2014 | Walsh et al. |
| 2014/0356370 A1 | 12/2014 | Swergold et al. |
| 2014/0356371 A1 | 12/2014 | Swergold et al. |
| 2015/0140002 A1 | 5/2015 | Baccara-Dinet et al. |
| 2015/0152191 A1 | 6/2015 | Baccara-Dinet et al. |
| 2015/0231236 A1 | 8/2015 | Pordy et al. |
| 2015/0283236 A1 | 10/2015 | Baccara-Dinet et al. |
| 2015/0284473 A1 | 10/2015 | Bessac et al. |
| 2015/0284474 A1 | 10/2015 | Sleeman et al. |
| 2016/0032015 A1 | 2/2016 | Walsh et al. |
| 2016/0115246 A1 | 4/2016 | Sasiela et al. |
| 2016/0137745 A1 | 5/2016 | Baccara-Dinet et al. |
| 2016/0137746 A1 | 5/2016 | Hanotin et al. |
| 2016/0152734 A1 | 6/2016 | Udata |
| 2017/0049886 A1 | 2/2017 | Pordy et al. |
| 2017/0096496 A1 | 4/2017 | Sleeman et al. |
| 2017/0266079 A1 | 9/2017 | Hanotin et al. |
| 2017/0296657 A1 | 10/2017 | Sleeman et al. |
| 2017/0340515 A1 | 11/2017 | Hanotin et al. |
| 2018/0044436 A1 | 2/2018 | Walsh et al. |
| 2018/0244801 A1 | 8/2018 | Sasiela et al. |
| 2018/0296670 A1 | 10/2018 | Jasson et al. |
| 2018/0296672 A1 | 10/2018 | Pordy et al. |
| 2018/0296675 A1 | 10/2018 | Coleman et al. |
| 2018/0333490 A1 | 11/2018 | Swergold |
| 2019/0031774 A1 | 1/2019 | Bujas-Bobanovic |
| 2019/0135941 A1 | 5/2019 | Sleeman et al. |
| 2019/0284301 A1 | 9/2019 | Walsh et al. |
| 2019/0292273 A1 | 9/2019 | Hanotin et al. |
| 2019/0330371 A1 | 10/2019 | Swergold et al. |
| 2019/0343719 A1 | 11/2019 | Hanotin et al. |
| 2020/0024364 A1 | 1/2020 | Baccara-Dinet et al. |
| 2020/0071422 A1 | 3/2020 | Sasiela et al. |
| 2020/0216565 A1 | 7/2020 | Baccara-Dinet et al. |
| 2020/0255544 A1 | 8/2020 | Hanotin et al. |
| 2021/0054100 A1 | 2/2021 | Walsh et al. |
| 2021/0100900 A1 | 4/2021 | Pordy et al. |
| 2021/0230719 A1 | 7/2021 | Huang et al. |
| 2021/0253735 A1 | 8/2021 | Sleeman et al. |
| 2022/0218823 A1 | 7/2022 | Hanotin et al. |
| 2022/0315669 A1 | 10/2022 | Baccara-Dinet et al. |

FOREIGN PATENT DOCUMENTS

| | | |
|---|---|---|
| CO | 11-37695 A | 12/2011 |
| EP | 0 409 281 A1 | 1/1991 |
| EP | 0 521 471 A1 | 1/1993 |
| EP | 1 067 182 A2 | 1/2001 |
| EP | 1 514 933 A1 | 3/2005 |
| EP | 1 317 537 B1 | 12/2006 |
| EP | 1 618 212 B1 | 11/2007 |
| EP | 2358756 A1 | 8/2011 |
| EP | 2387989 A2 | 11/2011 |
| EP | 1 528 933 B1 | 5/2012 |
| EP | 1528933 B1 | 5/2012 |
| EP | 1 802 344 B1 | 8/2012 |
| EP | 1802344 B1 | 8/2012 |
| EP | 2 238 985 B9 | 12/2012 |
| EP | 2238985 B9 | 12/2012 |
| EP | 2 275 119 B1 | 9/2013 |
| EP | 2275119 B1 | 9/2013 |
| EP | 2668211 A1 | 12/2013 |
| EP | 2668212 A2 | 12/2013 |
| EP | 2 703 008 A1 | 3/2014 |
| EP | 2 703 009 A1 | 3/2014 |
| EP | 2 706 070 A1 | 3/2014 |
| EP | 2702413 A1 | 3/2014 |
| EP | 2 234 600 B1 | 8/2014 |
| EP | 2 328 559 B1 | 1/2015 |
| EP | 2328559 B1 | 1/2015 |
| EP | 2 822 587 B1 | 2/2016 |
| EP | 2822587 B1 | 2/2016 |
| EP | 3004171 A1 | 4/2016 |
| EP | 3055333 A2 | 8/2016 |
| EP | 3068803 A1 | 9/2016 |
| EP | 2 648 750 B1 | 1/2017 |
| EP | 2648750 B1 | 1/2017 |
| EP | 3119810 A1 | 1/2017 |
| EP | 3156422 A2 | 4/2017 |
| EP | 3169353 A1 | 5/2017 |
| EP | 3169362 A1 | 5/2017 |
| EP | 2 704 742 B1 | 7/2017 |
| EP | 2704742 B1 | 7/2017 |
| EP | 3326648 A1 | 5/2018 |
| EP | 3337828 A1 | 6/2018 |
| EP | 3395836 A1 | 10/2018 |
| EP | 3634469 A1 | 4/2020 |
| EP | 3677277 A1 | 7/2020 |
| EP | 3689913 A1 | 8/2020 |
| EP | 3753575 A1 | 12/2020 |
| EP | 3882273 A1 | 9/2021 |
| EP | 3943510 A2 | 1/2022 |
| JP | 2000-509018 A | 7/2000 |
| JP | 2002-501886 A | 1/2002 |
| JP | 2010-523135 A | 7/2010 |
| JP | 2010-536384 A | 12/2010 |
| JP | 2011-501952 A | 1/2011 |
| JP | 2011-511637 A | 4/2011 |
| JP | 2011-512129 A | 4/2011 |
| JP | 2012-511913 A | 5/2012 |
| JP | 2014-511361 A | 5/2014 |
| JP | 2014-527967 A | 10/2014 |
| JP | 2016-538248 A | 12/2016 |
| JP | 2017-137338 A | 8/2017 |
| MA | 34923 B1 | 2/2014 |
| NZ | 613867 A | 9/2015 |
| RU | 2011129316 A | 1/2013 |
| RU | 2013139727 A | 3/2015 |
| RU | 2538801 C2 | 10/2015 |
| SG | 192117 A1 | 8/2013 |
| TW | 201036633 A | 10/2010 |
| WO | WO 1993/000807 A1 | 1/1993 |
| WO | WO 1997/035620 A1 | 10/1997 |
| WO | WO 1998/022136 A2 | 5/1998 |
| WO | WO 1999/038495 A2 | 8/1999 |
| WO | WO 2001/057081 A2 | 8/2001 |
| WO | WO 2002/020767 A2 | 3/2002 |
| WO | WO 2004/055164 A2 | 7/2004 |
| WO | WO 2004/097047 A1 | 11/2004 |
| WO | WO 2005/058365 A1 | 6/2005 |
| WO | WO 2005/103081 A2 | 11/2005 |
| WO | WO 2005/016280 A2 | 2/2006 |
| WO | WO 2006/033702 A2 | 3/2006 |
| WO | WO 2007/062040 A1 | 5/2007 |
| WO | WO 2007/143315 A2 | 12/2007 |
| WO | WO 2007/146511 A2 | 12/2007 |
| WO | WO 2007/149334 A2 | 12/2007 |
| WO | WO 2008/057457 A2 | 5/2008 |
| WO | WO 2008/057458 A2 | 5/2008 |
| WO | WO 2008/057459 A2 | 5/2008 |
| WO | WO 2008/063382 A2 | 5/2008 |
| WO | WO 2008/066776 A2 | 6/2008 |
| WO | WO 2008/125623 A2 | 10/2008 |
| WO | WO 2008/133647 A2 | 11/2008 |
| WO | WO 2008/138536 A2 | 11/2008 |
| WO | WO 2009/026558 A1 | 2/2009 |
| WO | WO 2009/042765 A1 | 4/2009 |
| WO | WO 2009/055783 A2 | 4/2009 |
| WO | WO 2009/100297 A1 | 8/2009 |
| WO | WO 2009/100318 A1 | 8/2009 |
| WO | WO 2009/125825 A1 | 10/2009 |
| WO | WO 2010/029513 A2 | 3/2010 |
| WO | WO 2010/032220 A1 | 3/2010 |
| WO | WO 2010/077854 A1 | 7/2010 |
| WO | WO 2010/102241 A1 | 9/2010 |

(56) References Cited

FOREIGN PATENT DOCUMENTS

| | | | |
|---|---|---|---|
| WO | WO 2010/148337 A1 | 12/2010 | |
| WO | WO 2011/028938 A1 | 3/2011 | |
| WO | WO 2011/039578 A1 | 4/2011 | |
| WO | WO 2011/053759 A1 | 5/2011 | |
| WO | WO 2011/061712 A1 | 5/2011 | |
| WO | WO-2011053759 A1 * | 5/2011 | ............ C07K 16/40 |
| WO | WO 2011/072263 A1 | 6/2011 | |
| WO | WO 2011/111007 A2 | 9/2011 | |
| WO | WO 2011/117401 A1 | 9/2011 | |
| WO | WO 2012/010125 A2 | 1/2012 | |
| WO | WO 2012/054438 A1 | 4/2012 | |
| WO | WO 2012/064792 A2 | 5/2012 | |
| WO | WO 2012/101251 A1 | 8/2012 | |
| WO | WO 2012/101252 A2 | 8/2012 | |
| WO | WO 2012/101253 A1 | 8/2012 | |
| WO | WO 2012/109530 A1 | 8/2012 | |
| WO | WO-2012145685 A1 * | 10/2012 | ............ A61J 1/065 |
| WO | WO 2012/146776 A1 | 11/2012 | |
| WO | WO 2012/154999 A1 | 11/2012 | |
| WO | WO 2012/168491 A1 | 12/2012 | |
| WO | WO 2013/039958 A1 | 3/2013 | |
| WO | WO 2013/039969 A1 | 3/2013 | |
| WO | WO 2013/158984 A1 | 10/2013 | |
| WO | WO 2013/166448 A1 | 11/2013 | |
| WO | WO 2013/169886 A1 | 11/2013 | |
| WO | WO 2013/177536 A2 | 11/2013 | |
| WO | WO 2014/194111 A1 | 12/2014 | |
| WO | WO 2014/197752 A1 | 12/2014 | |
| WO | WO 2015/054619 A2 | 4/2015 | |
| WO | WO 2015/073494 A1 | 5/2015 | |
| WO | WO 2015/123423 A2 | 8/2015 | |
| WO | WO 2015/140079 A1 | 9/2015 | |
| WO | WO 2015/142668 A1 | 9/2015 | |
| WO | WO 2016/011256 A1 | 1/2016 | |
| WO | WO 2016/011260 A1 | 1/2016 | |
| WO | WO 2018/225041 A1 | 12/2018 | |
| WO | WO 2019/173530 A1 | 9/2019 | |

OTHER PUBLICATIONS (Sep. 21, 2015) "Proprotein Convertase Subtilisin Kexin 9 (PCSK9) Inhibitors", Policy No. DRUG.00078, American Medical Association, Retrieved from: <<https://www.anthem.com/ca/medicalpolicies/policies/mp_pw_c182635.htm>>.

Abifadel, et al. (Aug. 2012) "Identification and Characterization of New Gain-of-Function Mutations in the PCSK9 Gene Responsible for Autosomal Dominant Hypercholesterolemia", Atherosclerosis, vol. 223, No. 2, pp. 394-400.

Abifadel, et al. (Apr. 2009) "Mutations and Polymorphisms in the Proprotein Convertase Subtilisin Kexin 9 (PCSK9) Gene in Cholesterol Metabolism and Disease", Human Mutation, vol. 30, No. 4, pp. 520-529.

Abifadel, et al. (Jun. 2003) "Mutations in PCSK9 Cause Autosomal Dominant Hypercholesterolemia", Nature Genetics, vol. 34, No. 2, pp. 154-156.

Alborn, et al. (Oct. 2007) "Serum Proprotein Convertase Subtilisin kexin type 9 is Correlated Directly with Serum LDL Cholesterol", Clinical Chemistry, vol. 53, No. 10, pp. 1814-1819.

Almagro, et al. (Jan. 1, 2008) "Humanization of Antibodies", Frontiers in Bioscience, vol. 13, pp. 1619-1633.

Al-Mashhadi, et al. (Jan. 2, 2013) "Atherosclerosis: Familial Hypercholesterolemia and Atherosclerosis in Cloned Minipigs created by DNA Transposition of a Human PCSK9 Gain-of-Function Mutant", Science Translational Medicine, vol. 5, No. 166, pp. 44-53.

Altschul, et al. (Oct. 5, 1990) "Basic Local Alignment Search Tool", Journal of Molecular Biology, vol. 215, No. 3, pp. 403-410.

Altschul, et al. (Sep. 20, 1997) "Gapped BLAST and PSI-BLAST: A New Generation of Protein Database Search Programs", Nucleic Acids Research, vol. 25, No. 17, pp. 3389-3402.

Amgen Inc. (May 27, 2010) "Ascending Multiple Dose Study to Evaluate the Safety, Tolerability, Pharmacokinetics and Pharmacodynamics of AMG 145 in Subjects with Hyperlipidemia on Stable Doses of a Statin", ClinicalTrials.gov Identifier: NCT01133522, Retrieved From: <<http://clinicaltrials.gov/ct2/show/nct01133522?term=amg+145&rank=2>>, XP002682099, 8 Pages.

Angal, et al. (Jan. 1993) "A Single Amino Acid Substitution Abolishes the Heterogeneity of Chimeric Mouse/Human (IgG4) Antibody", Molecular Immunology, vol. 30, No. 1, pp. 105-108.

Arai, Hidenori (Sep. 1, 2012) "Dyslipidemia of Diabetic Patients", From New "Guidelines for Prevention of Arteriosclerostic Diseases 2012 Edition", Seasonal Post, (Diabetes Network Editorial Department (SOUSINSYA)), vol. 4, No. 3, pp. 1-3.

Ason, et al. (2011) "Improved Efficacy for Ezetimibe and Rosuvastatin by Attenuating the Induction of PCSK9", Journal of Lipid Research, vol. 52, No. 4, pp. 679-687.

Attie, et al. (May 1, 2005) "Dual Regulation of the LDL Receptor-Some Clarity and New Questions", Cell Metabolism, vol. 5, pp. 290-292.

Bambauer, et al. (2012) "LDL-Apheresis: Technical and Clinical Aspects", The Scientific World Journal, vol. 2012, Article ID 314283, 19 Pages.

Barbie, et al. (1998) "The Human Immunoglobulin kappa Variable (IGKV) Genes and Joining (IGKJ) Segments", Experimental and Clinical Immunogenetics, vol. 15, No. 3, pp. 171-183.

Bartelds, et al. (2010) "Surprising Negative Association Between IgG1 Allotype Disparity and Anti-Adalimumab Formation: A Cohort Study", Arthritis Research & Therapy, vol. 12, No. 6: R221, pp. 1-7.

Bays, et al. (May-Jun. 2015) "Alirocumab Treatment Effect on Non-HDL-C: Pooled Analyses of 10 Phase 3 Trials in the ODYSSEY Program", Journal of Clinical Lipidology, vol. 9, Issue 3, pp. 471-472.

Bays, et al. (2014) "Efficacy and Safety of Combining Alirocumab with Atorvastatin or Rosuvastatin Versus Statin Intensification or Adding Ezetimibe in High Cardiovascular Risk Patients: Odyssey Options I and II", Circulation, vol. 130, pp. 2105-2126.

Bays, et al. (2014) "PCSK9 Inhibitor Alirocumab as Add-on to Atorvastatin versus Other Lipid Treatment Strategies in Patients at High CVD Risk: Odyssey Options I", Abstract A16194, Circulation, vol. 130, 2 Pages.

Bee, et al. (Feb. 19, 2009) "Precipitation of a Monoclonal Antibody by Soluble Tungsten", Journal of Pharmaceutical Sciences, vol. 98, Issue 9, pp. 3290-3301.

Bendig, Mary M. (1995) "Humanization of Rodent Monoclonal Antibodies by CDR Grafting", Methods: A Companion to Methods in Enzymology, vol. 8, pp. 83-93.

Benjannet, et al. (Oct. 13, 2006) "The Proprotein Convertase (PC) PCSK9 is Inactivated by Furin and/or PC5/6A: Functional Consequences of Natural Mutations and Post-Translational Modifications", Journal of Biological Chemistry, vol. 281, No. 41, pp. 30561-30572.

Berthold, et al. (Jan. 1, 2015) "Hyperlipoproteinemia(a): Clinical significance and Treatment Options", Atherosclerosis Supplements, vol. 14, No. 1, pp. 1-5.

Bird, et al. (Oct. 21, 1988) "Single-Chain Antigen-Binding Proteins", Science, vol. 242, No. 4877, pp. 423-426.

Blom, et al. (May 8, 2014) "A 52-Week Placebo-Controlled Trial of Evolocumab in Hyperlipidemia", The New England Journal of Medicine, vol. 370, No. 19, pp. 1809-1819.

Breen, et al. (Sep. 2001) "Effect of Moisture on the Stability of a Lyophilized Humanized Monoclonal Antibody Formulation", Pharmaceutical Research, vol. 18, Issue 9, pp. 1345-1353.

Brouwers, et al. (Nov. 2013) "Plasma Proprotein Convertase Subtilisin Kexin Type 9 Levels Are Related to Markers of Cholesterol Synthesis in Familial Combined Hyperlipidemia", Nutrition, Metabolism and Cardiovascular Diseases, vol. 23, Issue 11, pp. 1115-1121.

Cannon, et al. (Aug. 31, 2014) "Efficacy and Safety of Alirocumab in High Cardiovascular Risk Patients with Inadequately Controlled Hypercholesterolaemia on Maximally Tolerated Daily Statin: results from the Odyssey Combo II Study", Presentation Presented at the ESC Congress.

Cannon, et al. (May 14, 2015) "Efficacy and Safety of Alirocumab in High Cardiovascular Risk Patients with Inadequately Controlled Hypercholesterolaemia on Maximally Tolerated Doses of Statins:

(56) References Cited

OTHER PUBLICATIONS the Odyssey Combo II Randomized Controlled Trial", European Heart Journal, vol. 36, No. 19, pp. 1186-1194.
Cariou, et al. (May 23-26, 2015) "Patient and Physician Perspectives on Administration of the PCSK9 Monoclonal Antibody Alirocumab, an Injectable Medication to Lower LDL-C Levels", International Symposium on Atherosclerosis. Abstract No. 1039, 1 Page.
Carpenter, et al. (Aug. 1997) "Rational Design of Stable Lyophilized Protein Formulations: some Practical Advice", Pharmaceutical Research, vol. 14, No. 8, pp. 969-975.
Catapano, et al. (May 2013) "The Safety of Therapeutic Monoclonal Antibodies: Implications for Cardiovascular Disease and Targeting the PCSK9 Pathway", Atherosclerosis, vol. 228, No. 1, pp. 18-28.
Chan, et al. (Jun. 16, 2009) "A Proprotein Convertase Subtilisin/Kexin Type 9 Neutralizing Antibody Reduces Serum Cholesterol in Mice and Nonhuman Primates", Proceedings of the National Academy of Sciences of the United States of America, vol. 106, No. 24, pp. 9820-9825.
Chaparro-Riggers, et al. (Mar. 30, 2012) "Increasing Serum Half-Life and Extending Cholesterol Lowering in vivo by Engineering Antibody with pH-Sensitive Binding to PCSK9", Journal of Biological Chemistry, vol. 287, No. 14, pp. 11090-11097.
Chaudhary, et al. (Feb. 26, 2017) "PCSK9 Inhibitors: A New Era of Lipid Lowering Therapy", World Journal of Cardiology, vol. 9, Issue 2, pp. 76-91.
Colhoun, et al. (Sep. 20, 2014) "Efficacy and Safety of Alirocumab, a Fully Human PCSK9 Monoclonal Antibody, in High Cardiovascular Risk Patients with Poorly Controlled Hypercholesterolemia on Maximally Tolerated doses of Statins: Rationale and Design of the Odyssey Combo I and II Trials", BMC Cardiovascular Disorders, vol. 14, No. 121, 14 Pages.
Costet, P (May 1, 2012) "PCSK9 Inhibitors as LDL Cholesterol-Lowering Agents: Rationale, Concerns and Preliminary Outcomes", Drugs of the Future, vol. 37, No. 5, pp. 331-341.
Daugherty, et al. (Aug. 7, 2006) "Formulation and Delivery Issues for Monoclonal Antibody Therapeutics", Advanced Drug Delivery Reviews, vol. 58, No. 5-6, pp. 686-706.
Davidson, et al. (Sep.-Oct. 2011) "Clinical Utility of Inflammatory Markers and Advanced Lipoprotein Testing: Advice from an Expert Panel of Lipid Specialists", Journal of Clinical Lipidology, vol. 5, No. 5, pp. 338-367.
Defesche, et al. (Jun. 2-5, 2013) "Natural History of Autosomal Dominant Hypercholesterolemia Caused by Gain of Function Mutations in Proprotein Convertase Subtilisin/Kexin Type 9 (Pcsk9) (Funded by Regeneron/Sanofi)", Presentation presented at the 81st European Atherosclerosis Society.
Defesche, et al. (Jun. 2-5, 2013) "Natural History of Autosomal Dominant Hypercholesterolemia caused by Gain-of-Function Mutations in Proprotein Convertase Subtilisin/Kexin Type 9 (PCSK9) (Funded by Regeneron/Sanofi)", Abstract of a presentation presented at the 81st European Atherosclerosis Society (EAS) Congress, Lyon, France.
Dube, et al. (Apr. 2012) "Lipoprotein(a): More Interesting than ever after 50 Years", Current Opinion in Lipidology, vol. 23, No. 2, pp. 133-140.
Duff, et al. (May 1, 2009) "Antibody-Mediated Disruption of the Interaction between PCSK9 and the Low-Density Lipoprotein Receptor", Biochemical Journal, vol. 419, No. 3, pp. 577-584.
Dufour, et al. (2012) "Effect of REGN727/SAR236553 PCSK9 Fully Human Monoclonal Antibody in Patients with Elevated Triglycerides/Low High-Density Lipoprotein Cholesterol: Data from Three Phase 2 Studies", Abstract A16127, Circulation, vol. 126.
Dufour, et al. (Oct. 2014) "One Year Open-Label Treatment with Alirocumab 150 Mg Every Two Weeks in Heterozygous Familial Hypercholesterolemic Patients", Canadian Journal of Cardiology, vol. 30, Issue 10, Supplement, Abstract 546., p. S338.
Epresspack (Oct. 16, 2013) "Sanofi and Regeneron Report Positive Top-line Results with Alirocumab from First Phase 3 Study of a PCSK9 Inhibitor for LDL Cholesterol Reduction", Retrieved From: <<http://www.epresspack.net/mmr/sanofi-pcsk9-1st-phase3-results>>.
Fallon, et al. (Mar. 10, 2000) "Increased Endosomal Sorting of Ligand to Recycling Enhances Potency of an Interleukin-2 Analog", Journal of Biological Chemistry, vol. 275, No. 10, pp. 6790-6797.
Farnier, et al. (Aug. 2014) "Relationship between Alirocumab, PCSK9 and LDL-C Levels: Results from the Odyssey Mono Phase 3 Trial of Alirocumab 75 mg every 2 Weeks", Atherosclerosis, vol. 235, Issue 2, pp. e34-e35.
Farnier, Michel (Jun. 1, 2011) "The Role of Proprotein Convertase Subtilisin/Kexin type 9 in Hyperlipidemia: Focus on Therapeutic Implications", American Journal of Cardiovascular Drugs, vol. 11, No. 3, pp. 145-152.
Fasano, et al. (2008) "45 Activity of Gain-of-Function Pcsk9 Mutants on LDLR Correlates with Total-Cholesterol Values in ADH Patients", Nutrition Metabolism and Cardiovascular Diseases, vol. 18, No. 1, p. S46.
Fasano, et al. (Mar. 2009) "Degradation of LDLR Protein Mediated by 'Gain of Function' PCSK9 Mutants in Normal and ARH Cells", Atherosclerosis, vol. 203, Issue 1, pp. 166-171.
Foody, et al. (2013) "Attainment of Low-Density Lipoprotein Cholesterol Goals in Patients at High Cardiovascular Risk: Results from a Managed Care Population Study", Abstract A17254, Circulation, vol. 128.
Foote, et al. (Mar. 20, 1992) "Antibody Framework Residues Affecting the Conformation of the Hypervariable Loops", Journal of Molecular Biology, vol. 224, No. 2, pp. 487-499.
Gaudet, et al. (May-Jun. 2013) "Alirocumab, a Fully Human Monoclonal Antibody to PCSK9, Reduces High Plasma Lp(a) Concentration: Pooled Analysis of 352 Patients from Phase 2", Journal of Clinical Lipidology, vol. 7, Issue 3, pp. 283-284.
Gaudet, et al. (Sep. 29, 2016) "Effect of Alirocumab on Lipoprotein(a) Over ≥1.5 Years (from the Phase 3 ODYSSEY Program)", The American Journal of Cardiology, vol. 119, Issue 1, pp. 40-46.
Gaudet, et al. (Sep. 1, 2014) "Effect of Alirocumab, a Monoclonal Proprotein Convertase Subtilisin/Kexin 9 Antibody, on Lipoprotein(a) Concentrations (A Pooled Analysis of 150 mg Every Two Weeks Dosing from Phase 2 Trials)", The American Journal of Cardiology, vol. 114, No. 5, pp. 711-715.
Gaudet, et al. (2012) "Effect of SAR236553/REGN727 Fully Human Monoclonal Anti-Proprotein Convertase Subtilisin/Kexin type 9 Antibody on Plasma Lipoprotein(a) Concentrations: Pooled Analysis from Three Phase 2 Studies (NCT:01266876; 01288469; 01288443)", Abstract A14725, Circulation, vol. 126.
Gaudet, et al. (Nov. 20, 2012) "Effect of SAR236553/REGN727 Fully Human Monoclonal Anti-Proprotein Convertase Subtilisin/Kexin Type 9 Antibody on Plasma Lipoprotein(a) Concentrations: Pooled Analysis from Three Phase 2 Studies (NCT:01266876; 01288469; 01288443)", Abstract A16125, Circulation, vol. 126, No. 21.
Ginsberg, et al. (2014) "Odyssey High FH: Efficacy and Safety of Alirocumab In Patients with Severe Heterozygous Familial Hypercholesterolemia", Circulation, vol. 130, p. N2119.
Gonnet, et al. (Jun. 5, 1992) "Exhaustive Matching of the Entire Protein Sequence Database", Science, vol. 256, No. 5062, pp. 1443-1445.
Goodson, et al. (1984) "Dental Applications", Medical Applications of Controlled Release, vol. 2, pp. 115-138.
Gorcyca, et al. (May-Jun. 2015) "Prevalence of Atherosclerotic Cardiovascular Disease (ASCVD) and Diabetes Populations in the United States", Journal of Clinical Lipidology, vol. 9, Issue 3, 424 Pages.
Grozdanov, et al. (Feb. 2006) "Expression and Localization of PCSK9 in Rat Hepatic Cells", Biochemistry and Cell Biology, vol. 84, No. 1, pp. 80-92.
Gusarova, et al. (Mar. 25-30, 2012) "Fully Human Antibody that Blocks PCSK9 Demonstrates Reduction in LDL-C Preclinically and in early Clinical Trials", Abstract of oral presentation at the Keystone Symposia on Molecular and Cellular Biology, Montana, USA.

(56) References Cited

OTHER PUBLICATIONS

Gusarova, et al. (Sep. 25-28, 2013) "PCSK9 Inhibition by Monoclonal Antibody as a Promising Strategy for LDLC Lowering", Presented as an Oral Presentation at South East Lipid Research Conference.

Gusarova, et al. (Jan. 18, 2017) "Reduction of LDL Cholesterol by a Monoclonal Antibody to PCSK9 in Rodents and Nonhuman Primates", Clinical Lipidology, vol. 7, Issue 6, pp. 737-743.

Haddley, K. (Apr. 1, 2013) "ALIROCUMAB Anti-Proprotein Convertase 9 (PCSK9) MAb Treatment of Hypercholesterolemia", Drugs of the Future, vol. 38, No. 4, pp. 215-216.

Heap, et al. (Jun. 2005) "Analysis of a 17-Amino Acid Residue, Virus-Neutralizing Micro antibody", Journal of General Virology, vol. 86, No. Pt 6, pp. 1791-1800.

Hirayama, et al. (2014) "Effects of Evolocumab (AMG 145), a Monoclonal Antibody to PCSK9, in Hypercholesterolemic, Statin-Treated Japanese Patients at High Cardiovascular Risk-Primary Results from the Phase 2 YUKAWA Study", Circulation Journal, vol. 78, No. 5, pp. 1073-1082.

Hochleitner, et al. (Mar. 2000) "Characterization of a Discontinuous Epitope of the Human Immunodeficiency Virus (HIV) Core Protein p24 by Epitope Excision and Differential Chemical Modification Followed by Mass Spectrometric Peptide Mapping Analysis", Protein Science, vol. 9, No. 3, pp. 487-496.

Holliger, et al. (Jul. 15, 1993) ""Diabodies": Small Bivalent and Bispecific Antibody Fragments", Proceedings of the National Academy of Sciences of the United States of America, vol. 90, No. 14, pp. 6444-6448.

Hopkins, et al. (Nov. 26, 2013) "A Randomized Placebo-phase Clinical Trial with the Monoclonal Antibody Alirocumab Demonstrates Reductions in Low-density Lipoprotein Cholesterol in Patients with Proprotein Convertase Subtilisin/Kexin Type 9 Gain-of-Function Mutations", Circulation, vol. 128, Issue suppl 22, Abstract 17156.

Hopkins, et al. (Dec. 2015) "Characterization of Autosomal Dominant Hypercholesterolemia Caused by PCSK9 Gain of Function Mutations and Its Specific Treatment with Alirocumab, a PCSK9 Monoclonal Antibody", Circulation: Cardiovascular Genetics, vol. 8, No. 6, pp. 823-831.

Hopkins, et al. (Jun. 2011) "Familial Hypercholesterolemias: Prevalence, Genetics, Diagnosis and Screening Recommendations from the National Lipid Association Expert Panel on Familial Hypercholesterolemia", Journal of Clinical Lipidology, vol. 5, No. 3 Suppl, pp. S9-S17.

Hopkins, et al. (Oct. 2007) "The Lund-Mackay staging system for chronic rhinosinusitis: How is it used and what does it predict?", Otolaryngology-Head and Neck Surgery, vol. 137, No. 4, pp. 555-561.

Horton, et al. (Feb. 2007) "Molecular Biology of PCSK9: its role in LDL Metabolism", Trends in Biochemical Sciences, vol. 32, No. 2, pp. 71-77.

Hovingh, et al. (Apr. 2013) "Diagnosis and Treatment of Familial Hypercholesterolaemia", European Heart Journal, vol. 34, No. 13, pp. 962-971.

Huang, et al. (May-Jun. 2015) "Clinical Characteristics and Unmet Need Among Real-World Atherosclerotic Cardiovascular Disease (ASCVD) Patients Stratified by Stalin Use", Journal of Clinical Lipidology, vol. 9, No. 3, pp. 437-438.

Huston, et al. (Aug. 1988) "Protein Engineering of Antibody Binding Sites: Recovery of Specific Activity in an Anti-Digoxin Single-Chain Fv Analogue Produced in *Escherichia coli*", Proceedings of the National Academy of Sciences of the United States of America, vol. 85, No. 16, pp. 5879-5883.

Igawa, et al. (Nov. 2010) "Antibody Recycling by Engineered pH-Dependent Antigen Binding Improves the Duration of Antigen Neutralization", Nature Biotechnology, vol. 28, No. 11, pp. 1203-1207.

International Search Report & Written Opinion Received for PCT Application No. PCT/US2012/048574, dated Feb. 15, 2013, 18 Pages.

International Search Report & Written Opinion Received for PCT Application No. PCT/US2013/023784, dated Jul. 10, 2013, 22 Pages.

International Search Report & Written Opinion Received for PCT Application No. PCT/US2014/040695, dated Oct. 6, 14 Pages.

International Search Report & Written Opinion Received for PCT Application No. PCT/US2014/046170, dated Oct. 2, 2014, 14 Pages.

International Search Report and Written Opinion received for PCT Patent Application No. PCT/EP2012/051320, dated Sep. 21, 2012, 25 Pages.

International Search Report and Written Opinion received for PCT Patent Application No. PCT/EP2012/051321, dated Apr. 19, 2012, 10 Pages.

International Search Report and Written Opinion received for PCT Patent Application No. PCT/EP2015/055369, dated May 21, 2015, 11 Pages.

International Search Report and Written Opinion received for PCT Patent Application No. PCT/US2014/040050, dated Oct. 6, 2014, 17 Pages.

International Search Report and Written Opinion received for PCT Patent Application No. PCT/US2014/060109, dated Apr. 16, 2015, 18 Pages.

International Search Report and Written Opinion received for PCT Patent Application No. PCT/US2014/065149, dated Mar. 2, 2015, 17 Pages.

International Search Report and Written Opinion received for PCT Patent Application No. PCT/US2015/015633, dated Aug. 19, 2015, 23 Pages.

International Search Report and Written Opinion received for PCT Patent Application No. PCT/US2015/020564, dated Jun. 12, 2015, 12 Pages.

International Search Report and Written Opinion received for PCT Patent Application No. PCT/US2015/040754, dated Oct. 14, 2015, 16 Pages.

International Search Report and Written Opinion received for PCT Patent Application No. PCT/US2015/040765, dated Nov. 26, 2015, 15 Pages.

International Search Report and Written Opinion received for PCT Patent Application No. PCT/US2014/041204, dated Oct. 17, 2014, 14 Pages.

International Search Report Received for PCT Application No. PCT/EP2009/063195, dated Feb. 13, 2014, 8 Pages.

International Search Report Received for PCT Application No. PCT/US2013/055747, dated Feb. 13, 2014, 8 Pages.

International Search Report Received for PCT Application No. PCT/US2013/057898, dated Feb. 13, 2014, 8 Pages.

International Search Report Received for PCT Application No. PCT/US2012/043338, dated Aug. 23, 2012, 4 Pages.

Ito, et al. (Aug. 31, 1992) "The His-Probe Method: Effects of Histidine Residues Introduced into the Complementarity-Determining Regions of Antibodies on Antigen-Antibody Interactions at Different pH Values", FEBS Letters, vol. 309, No. 1, pp. 85-88.

Jefferis, et al. (Jul./Aug. 2009) "Human Immunoglobulin Allotypes", mAbs, vol. 1, No. 4, pp. 332-338.

Jones, et al. (Mar. 2015) "Pooled Safety and Adverse Events in Nine Randomized, Placebo-Controlled, Phase 2 and 3 Clinical Trials of Alirocumab", Journal of the American College of Cardiology, vol. 65, Issue 10 Supplement, A1363 Page.

Jorgensen, et al. (Jun. 2013) "Genetically Elevated Non-Fasting Triglycerides and Calculated Remnant Cholesterol as Causal Risk Factors for Myocardial Infarction", European Heart Journal, vol. 34, No. 24, pp. 1826-1833.

Junghans, et al. (Mar. 1, 1990) "Anti-Tac-H, a Humanized Antibody to the Interleukin 2 Receptor with New Features for Immunotherapy in Malignant and Immune Disorders", Cancer Research, vol. 50, No. 5, pp. 1495-1502.

Kastelein, et al. (Jun. 2014) "Efficacy and Safety of Alirocumab in Patients with Heterozygous Familial Hypercholesterolemia Not Adequately Controlled with Current Lipid-Lowering Therapy: Design and Rationale of the Odyssey FH Studies", Cardiovascular Drugs and Therapy, vol. 28, No. 3, pp. 281-289.

(56) References Cited

OTHER PUBLICATIONS

Kastelein, et al. (Aug. 31, 2014) "Efficacy and Safety of Alirocumab in Patients with Heterozygous Familial Hypercholesterolemia Not Adequately Controlled with Current Lipid-Lowering Therapy: Results of Odyssey FH I and FH II Studies", Poster Presented at the ECS Congress, Barcelona, Spain.

Kastner, et al. (2010) "Synergistic Effect of IL-6 and IL-4 in Driving Fate Revision of Natural Foxp3+ Regulatory T Cells", The Journal of Immunology, vol. 185, pp. 5778-5786.

Katayama, et al. (Oct. 2004) "Retrospective Statistical Analysis of Lyophilized Protein Formulations of Progenipoietin using PLS: Determination of the Critical Parameters for Long-Term Storage Stability", Journal of Pharmaceutical Sciences, vol. 93, No. 10, pp. 2609-2623.

Kawashiri, et al. (Nov. 20, 2012) "Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope", Circulation, vol. 126, Issue suppl_21, Abstract 1386.

Kereiakes, et al. (Dec. 2, 2014) "Efficacy and Safety of Alirocumab in High Cardiovascular Risk Patients with Suboptimally Controlled Hypercholesterolemia on Maximally Tolerated Doses of Statins: The Odyssey Combo I Study", Circulation, vol. 130, pp. 2119-2120.

Kereiakes, et al. (Jun. 2015) "Efficacy and Safety of The Proprotein Convertase Subtilisin/Kexin Type 9 Inhibitor Alirocumab Among High Cardiovascular Risk Patients on Maximally Tolerated Statin Therapy: The Odyssey Combo I Study", American Heart Journal, vol. 169, No. 6, pp. 906-915.

Khawli, et al. (2010) "Charge Variants in IgG1: Isolation, Characterization, In Vitro Binding Properties and Pharmacokinetics in Rats", mAbs, vol. 2, No. 6, pp. 613-624.

Kolata, Gina (Jul. 27, 2015) "Praluent Looks Cheap to Those with Extreme Cholesterol", The New York Times, Retrieved From:<<https://www.nytimes.com/2015/07/28/health/praluent-looks-cheap-to-those-with-extreme-cholesterol.html>>, 4 Pages.

Konrad, et al. (2011) "Effects of Currently Prescribed LDL-C-Lowering Drugs on PCSK9 and Implications for the Next Generation of LDL-C-Lowering Agents", Lipids in Health and Disease, vol. 10, No. 1, 38 Pages.

Koren, et al. (Apr. 2014) "Effects of Alirocumab, a Fully Human Monoclonal Antibody to Proprotein Convertase Subtilisin/Kexin Type 9, on Lipoprotein Particle Concentrations Determined by Nuclear Magnetic Resonance: Substudy of a Randomized Double-Blind Phase II Clinical Trial", Abstract A1373, Journal of the American College of Cardiology, vol. 63, Issue 12 Supplement.

Koren, et al. (2012) "Efficacy, Safety and Tolerability of 150 mg Q2W Dose of the Anti-PCSK9 mAb, REGN727/SAR236553: Data from 3 Phase 2 Studies", European Heart Journal, vol. 33, (Abstract Supplement), Abstract 429, 37 Pages.

Koren, et al. (May-Jun. 2013) "Efficacy, Safety and Tolerability of Alirocumab 150 mg Q2W, a Fully Human PCSK9 Monoclonal Antibody: A Pooled Analysis of 352 Patients from Phase 2", Journal of Clinical Lipidology, vol. 7, Issue 3, pp. 279-280.

Koren, et al. (Jan. 22, 2015) "Safety and Efficacy of Alirocumab 150 mg Every 2 Weeks, a Fully Human Proprotein Convertase Subtilisin/Kexin Type 9 Monoclonal Antibody: A Phase II Pooled Analysis", Postgraduate Medicine, vol. 127, Issue 2, pp. 125-132.

Koschinsky, et al. (Dec. 2014) "Lipoprotein(a): An Important Cardiovascular Risk Factor and a Clinical Conundrum", Endocrinology & Metabolism Clinics of North America, vol. 43, No. 4, pp. 949-962.

Kostner, et al. (Nov. 2013) "When should we Measure Lipoprotein (a)?", European Heart Journal, vol. 34, No. 42, pp. 3268-3276.

Krauss, et al. (Nov. 25, 2014) "Alirocumab, a Fully Human Monoclonal Antibody to Proprotein Convertase Subtilisin/kexin Type 9, and Its Effects on Lipoprotein Subtractions Determined by Ion Mobility", Circulation, vol. 130, issue suppl_2, Abstract 15525.

Kuhnast, et al. (Oct. 2014) "Alirocumab Inhibits Atherosclerosis, Improves the Plaque Morphology, and Enhances the Effects of a Statin", The Journal of Lipid Research, vol. 55, No. 10, pp. 2103-2112.

Kuhnast, et al. (Nov. 26, 2013) "PCSK-9 Monoclonal Antibody Alirocumab Dose-Dependently Decreases Atherosclerosis Development and Enhances the Effects of Atorvastatin in APOE*3Leiden. CETP Mice", Circulation, vol. 128, issue suppl_22, Abstract 15823, pp. 1-2.

Kuiper, et al. (May 2015) "Statin use and Low Density Lipoprotein Cholesterol Goal Attainment Among a High Cardiovascular Risk Population in the Netherlands", Pharmo ISA Poster, 1 Page.

Lagace, et al. (Nov. 1, 2006) "Secreted PCSK9 Decreases the Number of LDL Receptors in Hepatocytes and in Livers of Parabiotic Mice", Journal of Clinical Investigation, vol. 116, No. 11, pp. 2995-3005.

Lalanne, et al. (2005) "Wild-Type PCSK9 Inhibits LDL Clearance but Does Not Affect apoB-Containing Lipoprotein Production in Mouse and Cultured Cells", Journal of Lipid Research, vol. 46, No. 6, pp. 1312-1319.

Lambert, et al. (Dec. 2, 2014) "Normalization of low-density lipoprotein receptor expression in receptor defective homozygous familial hypercholesterolemia by inhibition of PCSK9 with alirocumab", Journal of the American College of Cardiology, vol. 64, No. 21, pp. 2299-2300.

Lambert, et al. (2009) "Review: Molecular Basis of PCSK9 Function", Atherosclerosis, vol. 203, No. 1, pp. 1-7.

Lambert, et al. (Dec. 2012) "The PCSK9 Decade", The Journal of Lipid Research, vol. 53, No. 12, pp. 2515-2524.

Lamon-Fava, et al. (Jun. 2011) "Lipoprotein(a) levels, apo(a) isoform size, and coronary heart disease risk in the Framingham Offspring Study", The Journal of Lipid Research, vol. 52, No. 6, pp. 1181-1187.

Langer, et al. (1974) "Medical Applications of Controlled Release", CRC Press, Boca Raton, Florida, pp. 115-138.

Langer, Robert (Sep. 28, 1990) "New Methods of Drug Delivery", Science, vol. 249, Issue 4976, pp. 1527-1533.

Lefranc, et al. (Jan. 2009) "IMGT®, the International ImMunoGeneTics Information System®", Nucleic Acids Research, vol. 37, pp. D1006-D1012.

Leuenberger, et al. (1996) "A Multilingual Glossary of Biotechnological Terms", Recueil Des Travaux Chimiques Des Pays Bas, vol. 115, No. 7, p. 382.

Li, et al. (Nov. 1, 2009) "Recent Patents on PCSK9: A New Target for Treating Hypercholesterolemia", Recent Patents on DNA and Gene Sequences, vol. 3, No. 3, pp. 201-212.

Lippi, et al. (Feb. 2000) "Lipoprotein (a): From Ancestral Benefit to Modern Pathogen?", QJM: An International Journal of Medicine, vol. 93, No. 2, pp. 75-84.

Lopez, et al. (2008) "Inhibition of PCSK9 as a Novel Strategy for the Treatment of Hypercholesterolemia", Drug News & Perspectives Abstract, vol. 21, No. 6, pp. 323-330.

Lose, et al. (Apr. 2013) "Evaluation of Proprotein Convertase Subtilisin/Kexin Type 9: Focus on Potential Clinical and Therapeutic Implications for Low-Density Lipoprotein Cholesterol Lowering", Pharmacotherapy: The Journal of Human Pharmacology and Drug Therapy, vol. 33, No. 4, pp. 447-460.

Lunven, et al. (Apr. 1, 2014) "A Randomized Study of The Relative Bioavailability, Pharmacodynamics, And Safety of Alirocumab, A Fully Human Monoclonal Antibody to Proprotein Convertase Subtilisin/Kexin Type 9, After Single Subcutaneous Administration at Three Different Injection Sites", Journal of the American College of Cardiology, vol. 63, (12 Supplement), p. A1377.

Lunven, et al. (Dec. 2014) "A Randomized Study of The Relative Pharmacokinetics, Pharmacodynamics and Safety of Alirocumab, A Fully Human Monoclonal Antibody to Pcsk9, After Single Subcutaneous Administration at Three Different Injection Sites in Healthy Subjects", Cardiovascular Therapeutics vol. 32, No. 6, pp. 297-301.

Maeda, et al. (Jul. 18, 2002) "pH-Dependent Receptor/Ligand Dissociation as a Determining Factor for Intracellular Sorting of Ligands for Epidermal Growth Factor Receptors in Rat Hepatocytes", Journal of Controlled Release, vol. 82, No. 1, pp. 71-82.

(56) References Cited

OTHER PUBLICATIONS

Majumdar, et al. (Jul. 1, 2011) "Evaluation of the Effect of Syringe Surfaces on Protein Formulations", Journal of Pharmaceutical Sciences, vol. 100, No. 7, pp. 2563-2573.
Marcovina, et al. (Dec. 17, 1998) "Lipoprotein(a) as a Risk Factor for Coronary Artery Disease", The American Journal of Cardiology, vol. 82, No. (12A), pp. 57U-66U.
Maxwell, et al. (May 4, 2004) "Adenoviral-Mediated Expression of Pcsk9 In Mice Results in A Low-Density Lipoprotein Receptor Knockout Phenotype", Proceedings of the National Academy of Sciences, vol. 101, No. 18, pp. 7100-7105.
McKenney, et al. (Mar. 24-27, 2012) "A Randomized, Double-Blind, Placebo-Controlled Trial Of The Safety And Efficacy Of A Monoclonal Antibody To Proprotein Convertase subtilisin/kexin Type 9 Serine Protease, Regn727/Sar236553, In Patients With Primary Hypercholesterolemia (NCT: 01288443)", Presented as a late-breaking oral presentation at the American College of Cardiology (ACC) Annual Scientific Session, Chicago, Illinois, USA, NCT: 01288443, 10 Pages.
McKenney, et al. (Jun. 2-5, 2013) "Dynamics Between the Monoclonal Antibody SAR236553/REGN727, Proprotein Convertase subtilisin/kexin type 9 (PCSK9) and Low-Density Lipoprotein Cholesterol (LDL-C) Levels (funding: Regeneron/ Sanofi)", Abstract of an Oral Presentation at the 81st European Atherosclerosis Society (EAS) Congress.
McKenney, et al. (Jun. 2-5, 2013) "Dynamics Between the Monoclonal Antibody SAR236553/REGN727, Proprotein Convertase subtilisin/kexin Type 9 (PCSK9) and Low-Density Lipoprotein Cholesterol (LDL-C) Levels (funding: Regeneron/Sanofi)", Presented as a poster presentation at the 81st European Atherosclerosis Society (EAS) Congress, Lyon, France.
McKenney, et al. (Mar. 28, 2012) "Safety and Efficacy of a Monoclonal Antibody to Proprotein Convertase subtilisin/kexin Type 9 Serine Protease, SAR236553/REGN727, in Patients with Primary Hypercholesterolemia Receiving Ongoing Stable Atorvastatin Therapy", Journal of the American College of Cardiology, vol. 59, No. 25, pp. 2344-2353.
McNutt, et al. (Dec. 1, 2015) "So Far, PCSK9 Inhibitors Work for All Heterozygous FH Patients", Circulation: Cardiovascular Genetics, vol. 8, pp. 749-751.
McPherson, Ruth (2013) "Remnant Cholesterol: Non-(HDL-C + LDL-C) as a Coronary Artery Disease Risk Factor", Journal of the American College of Cardiology, vol. 61, No. 4, pp. 437-439.
Meehan, et al. (May 5, 1997) "A Microinfusor Device for the Delivery of Therapeutic Levels of Peptides and Macromolecules", Journal of Controlled Release, vol. 46, Issues 1-2, pp. 107-116.
Miettinen, et al. (Nov. 1971) "Cholesterol Production in Obesity", Circulation, vol. 44, No. 5, pp. 842-850.
Missouri DU Report (2003) "Statin Therapy", Drug Use Review Newsletter, vol. 8, No. 6, pp. 1-9.
Moon, et al. (2007) "Lipoprotein(a) and LDL Particle Size are Related to the Severity of Coronary Artery Disease", Cardiology, vol. 108, pp. 282-289.
Moriarty, et al. (Nov.-Dec. 2015) "Efficacy and Safety of Alirocumab Versus Ezetimibe in Statin-Intolerant Patients, with a Statin-Re-Challenge Arm: The Odyssey Alternative Randomized Trial", Journal of Clinical Lipidology, vol. 9, Issue 6, pp. 758-769.
Moriarty, et al. (Nov.-Dec. 2014) "Efficacy and Safety of Alirocumab, a Monoclonal Antibody to PCSK9, in Statin-Intolerant Patients: Design and rationale of Odyssey Alternative, a Randomized Phase 3 trial", Journal of Clinical Lipidology, vol. 8, Issue 6, pp. 554-561.
Moriarty, et al. (Aug. 1, 2013) "Homogeneity of Treatment Effect of REGN727/SAR236553, a Fully Human Monoclonal Antibody Against PCSK9, In Lowering LDL-C: Data from Three Phase 2 Studies", European Heart Journal, vol. 34, supplement 1, Abstract 142, p. 18.
Moriarty, et al. (2014) "Odyssey Alternative: Efficacy and Safety of the proprotein Convertase subtilisin/kexin Type 9 Monoclonal Antibody, Alirocumab, Versus Ezetimibe, in Patients with Statin Intolerance as Defined by a Placebo Run-in and Statin Rechallenge Arm", Circulation, vol. 130, pp. 2108-2109.
Moriarty, et al. (May 13-16, 2015) "PCSK9 Inhibitors and their Effect on Patients who are Statin Intolerant or Receiving Lipoprotein-Apheresis", The 10th International Society for Apheresis Congress, Cancun, Mexico, 38 Pages.
Nakasako, et al. (Sep. 6, 1999) "The pH-Dependent Structural Variation of Complementarity-Determining Region H3 In the Crystal Structures of the Fv Fragment from An Anti-Dansyl Monoclonal Antibody", Journal of Molecular Biology, vol. 291, No. 1, pp. 117-134.
Naureckiene, et al. (Dec. 2003) "Functional Characterization of Narc 1, a Novel Proteinase Related to Proteinase K", Archives of Biochemistry and Biophysics, vol. 420, Issue 1, pp. 55-67.
Ned, et al. (2011) "Cascade Screening for Familial Hypercholesterolemia (FH)", PLoS Currents, vol. 3, 11 Pages.
Noguchi, et al. (May 1, 2015) "The E32K Variant of PCSK9 Exacerbates the Phenotype of Familial Hypercholesterolemia by Increasing PCSK9 Function and Concentration in The Circulation", Atherosclerosis, vol. 210, No. 1, pp. 166-172.
Nordestgaard, et al. (Oct. 21, 2010) "Lipoprotein(s) As Cardiovascular Risk Factor: Status", European Heart Journal, vol. 31, No. 23, pp. 2844-2853.
Padlan, et al. (Jan. 1995) "Identification of Specificity-Determining Residues in Antibodies", The FASEB Journal, vol. 9, No. 1, pp. 133-139.
Parhofer, Klaius G. (Mar. 1, 2011) "Lipoprotein(a): Medical Treatment Options for an Elusive Molecule", Current Pharmaceutical Design, vol. 17, No. 9, pp. 871-876.
Park, et al. (Nov. 26, 2004) "Post-transcriptional Regulation of Low Density Lipoprotein Receptor Protein by Proprotein Convertase Subtilisin/Kexin Type 9a in Mouse Liver", Journal of Biological Chemistry, vol. 279, No. 48, pp. 50630-50638.
Partial International Search Report received for PCT Patent Application No. PCT/US2014/040163, dated Nov. 6, 2014, 6 Pages.
Pearson, William R. (1994) "Using the FASTA Program to Search Protein and DNA Sequence Databases", Computer Analysis of Sequence Data, Humana Press, pp. 307-331.
Pfizer Inc. (Nov. 3, 2012) "Safety and Tolerability of Multiple Doses of PF-04950615 (RN316) In Subjects with Hypercholesterolemia", ClinicalTrials.gov Identifier: NCT01243151, Retrieved From: <<https://clinicaltrials.gov/ct2/show/NCT01243151>>, 10 Pages.
Pordy, et al. (May 1, 2013) "Alirocumab, a Fully Human Monoclonal Antibody to Proprotein Convertase subtilisin/kexin Type 9: Therapeutic Dosing in Phase 3 Studies", Journal of Clinical Lipidology, vol. 7, No. 3, p. 279.
Powell, et al. (Sep.-Oct. 1998) "Compendium of Excipients for Parenteral Formulations", PDA Journal of Pharmaceutical Science and Technology, vol. 52, No. 5, pp. 238-311.
Qiu, et al. (Aug. 2007) "Small Antibody Mimetics Comprising Two Complementarity-Determining Regions and A Framework Region for Tumor Targeting", Nature Biotechnology, vol. 25, No. 8, pp. 921-929.
QSM (2012) "Essential Medicines and Health Products", WHO Drug Information, vol. 26, No. 2, 4 Pages.
Rader, et al. (Mar. 1, 1995) "The Low-Density Lipoprotein Receptor Is Not Required for Normal Catabolism of Lp(a) in Humans", The Journal of Clinical Investigation, vol. 95, No. 3, pp. 1403-1408.
Rahilly-Tierney, et al. (Mar. 2009) "Low-Density Lipoprotein Reduction and Magnitude of Cardiovascular Risk Reduction", Preventive Cardiology, vol. 12, No. 2, pp. 80-87.
Ramanathan, et al. (Nov. 26, 2013) "Role of Alirocumab (proprotein Convertase subtilisin/kexin Type 9 Antibody) on CD81 Levels and Hepatitis C Virus Entry into Hepatocytes", Abstract A12052, Circulation, vol. 128, pp. 1-14.
Rashid, et al. (Apr. 12, 2005) "Decreased Plasma Cholesterol and Hypersensitivity to Statins in Mice Lacking Pcsk9", Proceedings of the National Academy of Sciences, vol. 102, No. 15, pp. 5374-5379.
Ray, Kausik K. (Jan. 2015) "Alirocumab: An Investigational Treatment for Hypercholesterolemia", Clinical Lipidology, vol. 10, No. 1, pp. 9-12.
Ray, et al. (Nov. 1, 2013) "Attainment of Low-Density Lipoprotein Cholesterol Goals in Patients at Very High Cardiovascular Risk in the United Kingdom: Results from A General Practice Population Study", Value Health, vol. 16, No. 7, p. A513.

(56) References Cited

OTHER PUBLICATIONS

Reddy, et al. (Feb. 15, 2000) "Elimination of Fc Receptor-Dependent Effector Functions of a Modified IgG4 Monoclonal Antibody to Human CD4", The Journal of Immunology, vol. 164, No. 4, pp. 1925-1933.

Regeneron Newsroom (Dec. 19, 2013) "Sanofi and Regeneron Announce Collaboration with American College of Cardiology for PCSK9 Inhibitor Clinical Program", Retrieved From <<https://newsroom.regeneron.com./news-releases/news-release-details/sanofi-and-regeneron-announce-collaboration-american-college>>, 2 pages.

Regeneron Pharmaceuticals (Apr. 7, 2015) "Study of Alirocumab (REGN727/SAR236553) in Patients with Heterozygous Familial Hypercholesterolemia (HeFH) Undergoing Low-density Lipoprotein (LDL) Apheresis Therapy (Odyssey Escape)", ClinicalTrials.gov Identifier: NCT02326220, ClinicalTriais.gov Archive, Retrieve From: <<https://clinicaitriais.gov/archive/NCT02326220/2015_04_07>>, 5 Pages.

Regeneron Pharmaceuticals (Mar. 10, 2015) "Study of Alirocumab (REGN727/SAR236553) in Patients with Heterozygous Familial Hypercholesterolemia (HeFH) Undergoing Low-density Lipoprotein (LDL) Apheresis Therapy (Odyssey Escape)", ClinicalTrials.gov Identifier: NCT02326220, ClinicalTriais.gov Archive, Retrieved from:<<https://clinicaitriais.gov/archive/NCT02326220/2015_03_10>>, 5 Pages.

Regeneron Pharmaceuticals (Dec. 28, 2014) "Study of Alirocumab (REGN727/SAR236553) in Patients with Heterozygous Familial Hypercholesterolemia (HeFH) Undergoing Low-density Lipoprotein (LDL) Apheresis Therapy (Odyssey Escape)", ClinicalTrials.gov Identifier: NCT02326220, ClinicalTriais.gov Archive, Retrieved From:<<https://clinicaitriais.gov/archive/NCT02326220/2014_12_28>>, 5 Pages.

Reineke, Ulrich (2004) "Antibody Epitope Mapping Using Arrays of Synthetic Peptides", Antibody Engineering, Humana Press, vol. 248, pp. 443-463.

Rey, et al. (Apr. 2014) "Randomized, Partial Blind Study of The Pharmacodynamics, Pharmacokinetics and Safety of Multiple Subcutaneous Doses of Alirocumab, A Fully Human Monoclonal Antibody to Proprotein Convertase subtilisin/kexin type 9, Administered Every 4 Weeks Alone or In Co", Journal of the American College of Cardiology, vol. 63, No. 12, Supplement 1, p. A1375.

Reyes-Soffer, et al. (2015) "Abstract 129: Effects of A Proprotein Convertase Subtilisin/Kexin Type 9 Inhibitor, Alirocumab, On Lipid and Lipoprotein Metabolism in Normal Subjects", Arteriosclerosis, Thrombosis, and Vascular Biology, vol. 35, p. A129.

Reyes-Soffer, et al. (Jan. 23, 2017) "Effects of PCSK9 Inhibition with Alirocumab on Lipoprotein Metabolism in Healthy Humans", Circulation, vol. 135, No. 4, pp. 352-362.

Rhainds, et al. (Dec. 2012) "PCSK9 Inhibition and LDL Cholesterol Lowering: The Biology of an Attractive Therapeutic Target and Critical Review of The Latest Clinical Trials", Clinical Lipidology, vol. 7, No. 6, pp. 621-640.

Robinson, et al. (Mar. 17, 2015) "Adverse Events in Patients with Low-Density Lipoprotein Cholesterol Levels <25 or <15 mg/dL on at Least Two Consecutive Visits in Fourteen Randomized, Controlled, Clinical Trials of Alirocumab", Journal of the American College of Cardiology, vol. 65, (10 Supplement), p. A1350.

Robinson, et al. (Oct. 2014) "Efficacy and Safety of Alirocumab As Add-On Therapy in High-Cardiovascular-Risk Patients with Hypercholesterolemia Not Adequately Controlled with Atorvastatin (20 Or 40 Mg) Or Rosuvastatin (10 or 20mg): Design and Rationale of The Odyssey Options Studies", Clinical cardiology, vol. 37, No. 10, pp. 597-604.

Robinson, et al. (Apr. 16, 2015) "Efficacy and Safety of Alirocumab in Reducing Lipids and Cardiovascular Events", New England Journal of Medicine, vol. 372, No. 16, pp. 1489-1499.

Robinson, et al. (Aug. 31, 2014) "Long-term safety, tolerability and efficacy of alirocumab versus placebo in high cardiovascular risk patients: first results from the Odyssey Long Term study in 2,341 patients", Highlights Presented at ESC Congress, Barcelona Spain., 1 Page.

Robinson, et al. (2014) "Long-Term Safety, Tolerability and Efficacy of Alirocumab Versus Placebo in High Cardiovascular Risk Patients: First Results from the Odyssey Long Term Study In 2,341 Patients", Circulation, vol. 130, p. 2120.

Robinson, Noah E. (Apr. 16, 2002) "Protein Deamidation", Proceedings of the National Academy of Sciences, vol. 99, No. 8, pp. 5283-5288.

Romagnuolo, et al. (Mar. 16, 2015) "Lipoprotein(a) Catabolism is Regulated by Proprotein Convertase Subtilisin/Kexin Type 9 through the Low-Density Lipoprotein Receptor", The Journal of Biological Chemistry, vol. 290, No. 18, pp. 11649-11662.

Roth, et al. (Apr. 2014) "A 24-Week Study of Alirocumab Monotherapy Versus Ezetimibe: The First Phase 3 Data of a Proprotein Convertase Subtilisin/Kexin Type 9 Inhibitor", Journal of the American College of Cardiology, vol. 63, (12 Supplement), p. A1370.

Roth, et al. (Mar. 2014) "Alirocumab for Hyperlipidemia: Physiology of PCSK9 Inhibition, Pharmacodynamics and Phase I And II Clinical Trial Results of A PCSk9 Monoclonal Antibody", Future Cardiology, vol. 10, No. 2, pp. 183-199.

Roth, et al. (Nov. 15, 2012) "Atorvastatin with Or Without an Antibody to PCSK9 In Primary Hypercholesterolemia", The new England Journal of Medicine, vol. 367, No. 20, pp. 1891-1900.

Roth, et al. (Jul. 2, 2014) "Monotherapy with The PCSK9 Inhibitor Alirocumab Versus Ezetimibe in Patients with Hypercholesterolemia: Results of A 24 Week, Double-Blind, Randomized Phase 3 Trial", International Journal of Cardiology, vol. 176, No. 1, pp. 55-61.

Roth, et al. (Jan. 2015) "Odyssey Mono: Effect of Alirocumab 75 mg Subcutaneously Every 2 Weeks as Monotherapy Versus Ezetimibe Over 24 Weeks", Future Cardiology, vol. 11, No. 1, pp. 27-37.

Roth, et al. (May 2015) "Patient and Physician Perspectives on Administration of the PCSK9 Monoclonal Antibody Alirocumab, an Injectable Medication to Lower LDL-C Levels", Journal of Clinical Lipidology, vol. 37, No. 9, pp. 1945-1954.

Roth, et al. (May 23-26, 2015) "Phase 3 Randomized Trial Evaluating Alirocumab Every Four Weeks Dosing as Add-on to Statin or as Monotherapy: Odyssey Choice I", International Symposium on Atherosclerosis, Abstract No. 254.

Roth, et al. (Mar. 27, 2012) "The Effects of Co-Administering A Monoclonal Antibody to Proprotein Convertase subtilisin/kexin Type 9 serine protease, REGN727/SAR236553, with 10 and 80 mg Atorvastatin Compared to 80 mg Atorvastatin Alone in Patients with Primary Hypercholesterolemia (NC", Journal of the American College of Cardiology, vol. 59, Supplement 13, p. E1620.

Saeedi, et al. (Mar. 31, 2016) "Lipoprotein (a), an Independent Cardiovascular Risk Marker", Clinical Diabetes and Endocrinology, vol. 2, No. 7, pp. 1-6.

Sahebkar, et al. (Aug. 8, 2013) "New LDL-Cholesterol Lowering Therapies: Pharmacology, Clinical Trials, and Relevance to Acute Coronary Syndromes", Clinical Therapeutics, vol. 35, No. 8, pp. 1082-1098.

Sanofi (Mar. 11, 2014) "A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome", Archive from ClinicalTrials.gov for NCT01663402, 3 Pages.

Sanofi (Jul. 13, 2010) "Ascending Multi-Dose Study of REGN727(SAR236553) With and Without Concomitant Atorvastatin", ClinicalTrials.gov Identifier: NCT01161082, Retrieved From: <<https://clinicaltrials.gov/ct2/show/NCT01161082?term=NCT01161082>>, 6 Pages.

Sanofi (Feb. 1, 2011) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved From: <<https://clinicaltrials.gov/archive/NCT01288443/2011_02_01>>.

Sanofi (Feb. 1, 2011) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, Retrieved from: <<https://clinicaltrials.gov/archive/NCT01288469/2011_02_01>>, 9 Pages.

(56) References Cited

OTHER PUBLICATIONS

Sanofi (Jul. 17, 2012) "Efficacy and Safety of Alirocumab (SAR236553/REGN727) Versus Ezetimibe in Patients with Hypercholesterolemia (Odyssey Mono)", ClinicalTrials.gov Identifier: NCT01644474, Retrieved from: <<https://clinicaltrials.gov/ct2/show/NCT01644474?term=NCT01644474>>, 10 Pages.

Sanofi (Jul. 16, 2012) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/ct2/show/NCT01644188?term=NCT01644188>>, 12 Pages.

Sanofi (Jun. 8, 2012) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, US National Institutes of Health, Retrieved From: <<https://clinicaltrials.gov/ct2/show/NCT01617655?term=NCT01617655>>, 12 Pages.

Sanofi (Jul. 16, 2012) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved From: <<https://clinicaltrials.gov/ct2/show/NCT01644175?term=NCT01644175>>, 11 Pages.

Sanofi (Jan. 6, 2012) "Long-term Safety and Tolerability of Alirocumab (SAR236553/REGN727) Versus Placebo on Top of Lipid-Modifying Therapy in High Cardiovascular Risk Patients with Hypercholesterolemia (ODYSSEY Long Term)", ClinicalTrials.gov Identifier: NCT01507831, Retrieved From: <<https://clinicaltrials.gov/ct2/show/NCT01507831?term=NCT01507831&draw=2&rank=1>>.

Sanofi (Jun. 27, 2013) "Long-term Safety and Tolerability of Alirocumab SAR236553 (REGN727) in High Cardiovascular Risk Patients with Hypercholesterolemia Not Adequately Controlled with Their Lipid Modifying Therapy: A Randomized, Double-Blind, Placebo-Controlled Study", Archive from ClinicalTrials.gov for NCT01507831, 3 Pages.

Sanofi (Aug. 8, 2012) "Open-Label Extension of Study R727-CL-1003 (NCT01266876) to Evaluate the Long-Term Safety and Efficacy of Alirocumab (REGN727) in Participants with Heterozygous Familial Hypercholesterolemia (HeFH)", ClinicalTrials.gov Identifier: NCT01576484, Retrieved From: <<https://clinicaltrials.gov/ct2/show/NCTO 1663402>>.

Sanofi (Oct. 8, 2012) "Study of Alirocumab (REGN727/SAR236553) in Patients with HeFH (Heterozygous Familial Hypercholesterolemia) Who Are Not Adequately Controlled with Their LMT (Lipid-Modifying Therapy) (Odyssey FH II)", ClinicalTrials.gov Identifier: NCT01709500, Retrieved from: <<https://clinicaltrials.gov/ct2/show/NCT01709500?term=NCT01709500>>, 13 Pages.

Sanofi (Dec. 23, 2010) "Study of the Safety and Efficacy of REGN727/SAR236553 in Patients with HeFH Hypercholesterolemia", ClinicalTrials.gov Identifier: NCT01266876, Retrieved From: <<https://clinicaltrials.gov/archive/NCT01266876/2010_12_23>>.

Sarkar, et al. (Sep. 2002) "Rational Cytokine Design for Increased Lifetime and Enhanced Potency Using Ph-Activated "Histidine Switching"", Nature Biotechnology, vol. 20, pp. 908-913.

Scaviner, et al. (1999) "Protein Displays of the Human Immunoglobulin Heavy, Kappa and Lambda Variable and Joining Regions", Experimental and Clinical Immunogenetics, vol. 16, No. 4, pp. 234-240.

Schäfer, et al. (Mar. 14-16, 2011) "Cholesterol Lowering Effect of SAR236553/REGN727, a Fully Human PCSK9 Blocking Monoclonal Antibody in Male Syrian hamster", Presented as a poster at the Drugs Affecting Lipid Metabolism (DALM)—XVII International Symposium, Doha, Qatar, pp. 14-16.

Schwartz, et al. (Aug. 7, 2014) "Effect of Alirocumab, A Monoclonal Antibody to pcsk9, on Long-Term Cardiovascular Outcomes Following Acute Coronary Syndromes: Rationale and Design of The ODYSSEY Outcomes Trial", American Heart Journal, vol. 168, No. 5, pp. 682-689.

Sefton, Michael V. (Jan. 1, 1987) "Implantable Pumps", Critical Reviews in Biomedical Engineering, vol. 14, No. 3, pp. 201-240.

Seidah, et al. (Feb. 4, 2003) "The Secretory Proprotein Convertase Neural Apoptosis-Regulated Convertase 1 (NARC-1): Liver Regeneration and Neuronal Differentiation", Proceedings of the National Academy of Sciences, vol. 100, No. 3, pp. 928-933.

Shao, W (Apr. 26, 2014) "New Therapies for Lowering LDL-C: Targeting PCSK9", Abstract of oral presentation at the Sino-American Pharmaceutical Professionals Association—2014 Scientific Symposium, New Jersey, USA.

Shields, et al. (Jul. 26, 2002) "Lack of Fucose on Human IgG1 N-Linked Oligosaccharide Improves Binding to Human FcγRIII and Antibody-dependent Cellular Toxicity", The Journal of Biological Chemistry, vol. 277, No. 30, pp. 26733-26740.

Shoji, et al. (Jul. 1, 1998) "Intermediate-Density Lipoprotein as an Independent Risk Factor for Aortic Atherosclerosis in Hemodialysis Patients", Journal of the American Society of Nephrology, vol. 9, No. 7, pp. 1277-1284.

Soutar, Anne K. (Jun. 1, 2011) "Unexpected Roles for PCSK9 in Lipid Metabolism", Current Opinion in Lipidology, vol. 22, No. 3, pp. 192-196.

Stahl, Neil (Jul. 15, 2010) "Early Clinical Development #1 REGN727: Anti-PCSK9", Regeneron Pharmaceuticals, pp. 1-21.

Steen, et al. (Nov. 25, 2014) "Attainment of Lipid Levels in Patients at High Cardiovascular Risk: Results from a U.S. Managed Care Population Study", Circulation, vol. 130, Supplement 2, p. A19949.

Steen, et al. (Mar. 2015) "Cardiovascular Event Rates in a High-Risk Managed Care Population in the United States", Journal of the American College of Cardiology vol. 65, Issue 10 Supplement, p. A1647.

Stein, et al. (Mar. 22, 2012) "Effect of a Monoclonal Antibody to PCSK9 on LDL Cholesterol", New England Journal of Medicine, vol. 366, No. 12, pp. 1108-1118.

Stein, et al. (Jul. 2012) "Effect of A Monoclonal Antibody to PCSK9 On LDL Cholesterol", Obstetrical and Gynecological Survey, vol. 67, No. 7, pp. 413-414.

Stein, et al. (May 26, 2012) "Effect of a Monoclonal Antibody to PCSK9, REGN727/SAR236553, to Reduce Low-Density Lipoprotein Cholesterol in Patients with Heterozygous Familial Hypercholesterolaemia on Stable Statin Dose with or Without Ezetimibe Therapy: A Phase 2 Randomised Controlled", Lancet, vol. 380, No. 9836, pp. 29-36.

Stein, et al. (Mar. 30, 2014) "One Year Open-Label Treatment with Alirocumab 150 Mg Every Two Weeks in Heterozygous familial Hypercholesterolemic Patients", Journal of the American College of Cardiology vol. 63, No. 12, Supplement 1, p. A1371.

Stein, et al. (Mar. 2013) "Potential of proprotein Convertase Subtilisin/Kexin Type 9 Based Therapeutics", Current Atherosclerosis Reports, vol. 15, No. 3, pp. 1-14.

Stein, et al. (May 25-28, 2012) "Safety and Efficacy of a Monoclonal Antibody to PCSK9, REGN727/SAR236553, in Statin-Treated Heterozygous Familial Hypercholesterolemia Patients", Presented as an oral presentation at the 80th European Atherosclerosis Society (EAS) Congress, Milan, Italy, Abstract 1398.

Steinberg, et al. (Jun. 16, 2009) "Inhibition of PCSK9: A powerful Weapon for Achieving ideal LDL Cholesterol Levels", Proceedings of the National Academy of Sciences USA, vol. 106, No. 24, pp. 9546-9547.

Stone, et al. (2014) "2013 ACC/AHA Guideline on the Treatment of Blood Cholesterol to Reduce Atherosclerotic Cardiovascular Risk in Adults", Journal of the American College of Cardiology, vol. 63, No. 25, pp. 2889-2934.

Stroes, et al. (Jun. 17, 2014) "Anti-PCSK9 Antibody Effectively Lowers Cholesterol in Patients with Statin Intolerance", Journal of the American College of Cardiology, vol. 63, No. 23, pp. 2541-2548.

Stroes, et al. (Mar. 17, 2015) "Efficacy and Safety of Different Dosing Regimens of Alirocumab (Starting Doses Of 75 Mg Every Two Weeks And 150 Mg Every Four Weeks) Versus Placebo in Patients with Hypercholesterolemia Not Treated Using Statins: The Odyssey Choice II Study", Journal of the American College of Cardiology, vol. 65, Supplement 10, p. A1370.

(56) References Cited

OTHER PUBLICATIONS

Sullivan, et al. (Dec. 19, 2012) "Effect of a Monoclonal Antibody to PCSK9 on Low-Density Lipoprotein Cholesterol Levels in Statin-Intolerant Patients", JAMA, vol. 308, No. 23, pp. 2497-2506.
Swergold, et al. (Oct. 22-26, 2013) "Identification and Characterization of Patients with Autosomal Dominant Hypercholesterolemia Caused by Gain-of-Function Mutations in Proprotein Convertase subtilisin/kexin type 9 and Comparison with Patients with Familial Hypercholesterolemia (FH) and Familial Defective Apolipoprotein B (FOB)", Abstract of a Poster Presentation at the American Society of Human Genetics (ASHG), Boston, USA.
Swergold, et al. (2011) "Inhibition of Proprotein Convertase subtilisin/kexin Type 9 With A Monoclonal Antibody REGN727/SAR236553, Effectively Reduces Low-Density-Lipoprotein Cholesterol, as Mono or Add-On Therapy in Heterozygous Familial and Non-Familial Hypercholesterolemia", Abstract 16265, Circulation, vol. 124, Supplement 21.
Swergold, et al. (2011) "REGN727/SAR236553, a Fully Human Proprotein Convertase Subtilisin Kexin 9 (PCSK9) Monoclonal Antibody: Effects on Safety and Lipid and Lipoprotein Profiles When Administered Subcutaneously", Journal of the American College of Cardiology vol. 57, No. 14, p. E2023.
Swergold, et al. (May 1, 2011) "REGN727/SAR236553, a Fully-Human Monoclonal Antibody to Proprotein Convertase subtilisin kexin 9 (PCSK9), Decreases ApoB and Non-HDL-C When Administered Intravenously to Healthy Volunteers", Abstract 135, Journal of Clinical Lipidology, vol. 5, No. 3, p. 219.
Swergold, et al. (2010) "Safety, Lipid, And Lipoprotein Effects of REGN727/SAR236553, a Fully Human Proprotein Convertase subtilisin kexin 9 (PCSK9) Neutralizing Monoclonal Antibody Administered Intravenously to Healthy volunteers", Abstract 23251, Circulation, vol. 122, Supplement 21.
Teramoto, et al. (Nov. 25, 2014) "Efficacy and Safety of Alirocumab In Japanese Patients with Hypercholesterolemia on Stable Statin Therapy: First Data with the 75 Mg Every Two Weeks Dose", Circulation, vol. 130, Supplement 2, Abstract A13651.
Third Party Observations corresponding to European Patent Application No. 12761864.3, dated Feb. 24, 2016, 9 pages.
Timms, et al. (Mar. 2004) "A Mutation in PCSK9 Causing Autosomal-Dominant Hypercholesterolemia in a Utah Pedigree", Human Genetics vol. 114, No. 4, pp. 349-353.
Tiwari, et al. (Aug. 2011) "Statins Therapy: A Review on Conventional and Novel Formulation Approaches", Journal of Pharmacy and Pharmacology, vol. 63, No. 8, pp. 983-998.
Todo, et al. (Oct. 2004) "Detailed Analysis of Serum Lipids and Lipoproteins from Japanese Type Iii Hyperlipoproteinemia with Apolipoprotein E2/2 Phenotype", Clinica Chimica Acta, vol. 348, Issues 1-2, pp. 35-40.
Toth, et al. (2013) "Alirocumab, A Proprotein Convertase subtilisin/kexin Type 9 Monoclonal Antibody, Reduces Cholesterol Concentrations of All Serum Low-Density Lipoprotein Cholesterol Fractions", Abstract 17313, Circulation, vol. 128.
Toth, et al. (2013) "Alirocumab, A Proprotein Convertase subtilisin/kexin Type 9 Monoclonal Antibody, Reduces Cholesterol Concentrations of Serum Remnant Lipoprotein Fractions, Very Low-Density Lipoproteins and Triglycerides", Abstract 17492, Circulation, vol. 128.
Toth, et al. (Aug. 1, 2014) "Proprotein Convertase subtilisin/kexin 9 Monoclonal Antibody Therapy Significantly Reduces Apoprotein CII and CIII Levels in Serum", Atherosclerosis, vol. 235, No. 2, Abstract 593], pp. e107-e108.
Tsimikas, et al. (Jul. 22, 2015) "Antisense Therapy Targeting Apolipoprotein(A): A Randomised Double-Blind, Placebo-Controlled Phase 1 Study", Lancet, vol. 386, Issue 10002, pp. 1472-1483.
Tutt, et al. (Jul. 1, 1991) "Trispecific F (ab') 3 Derivatives That Use Cooperative Signaling Via The TCR/CD3 Complex and CD2 To Activate and Redirect Resting Cytotoxic T Cells", The Journal of Immunology, vol. 147, No. 1, pp. 60-69.
Vajdos, et al. (Jul. 1, 2002) "Comprehensive Functional Maps of the Antigen-Binding Site of An Anti-ErbB2 Antibody Obtained with Shotgun Scanning Mutagenesis", Journal of Molecular Biology, vol. 320, No. 2, pp. 415-428.
Van Der Hoorn, et al. (Aug. 1, 2014) "Alirocumab, A Monoclonal Antibody to PCSK-9, Dose-Dependently Decreases Atherosclerosis, Improves Plaque Stability and Shows Additive Effects with Atorvastatin in APOE*3Leiden.CETP Mice", Atherosclerosis, vol. 235, No. 2, Abstract WS16, pp. e19.
Varbo, et al. (Jan. 29, 2013) "Remnant Cholesterol as a Casual Risk Factor for Ischemic Heart Disease", Journal of the American College of Cardiology, vol. 61, No. 4, pp. 427-436.
Varret, et al. (May 1, 1999) "A Third Major Locus for Autosomal Dominant Hypercholesterolemia Maps to 1p. 34.1-p. 32", The American Journal of Human Genetics, vol. 64, No. 5, pp. 1378-1387.
Voet, et al. (1999) "Fundamentals of Biochemistry", Von Hoffmann Press, Inc., pp. 260-264.
Voet, et al. (1999) "Fundamentals of Biochemistry", Von Hoffman Press, Inc., pp. 80-81.
Wang, et al. (Jan. 2007) "Antibody Structure, Instability, and Formulation", Journal of Pharmaceutical Sciences, vol. 96, No. 1, pp. 1-26.
Wang, et al. (Sep. 2009) "Fixed Dosing Versus Body Size-Based Dosing of Monoclonal Antibodies in Adult Clinical Trials", The Journal of Clinical Pharmacology, vol. 49, No. 9, pp. 1012-1024.
Wang, Wei (Aug. 20, 1999) "Instability, Stabilization and Formulation of Liquid Protein Pharmaceuticals", International Journal of Pharmaceutics, vol. 185, Issue 2, pp. 129-188.
Ward, et al. (Oct. 12, 1989) "Binding Activities of a Repertoire of Single Immunoglobulin Variable Domains Secreted from *Escherichia coli*", Nature, vol. 341, No. 6242, pp. 544-546.
Watanabe, et al. (May 1, 2009) "Optimizing pH Response of Affinity between Protein G and IgG Fc", Journal of Biological Chemistry, vol. 284, No. 18, pp. 12373-12383.
Webb, et al. (Feb. 1, 2002) "A New Mechanism for Decreasing Aggregation of Recombinant Human Interferon-γ by a Surfactant: Slowed Dissolution of Lyophilized Formulations in a Solution Containing 0.03% Polysorbate 20", Journal of pharmaceutical sciences, vol. 91, No. 2, pp. 543-558.
Westerterp, et al. (Nov. 2006) "Cholesteryl Ester Transfer Protein Decreases High-Density Lipoprotein and Severely Aggravates Atherosclerosis in APOE*3-Leiden Mice", Arteriosclerosis, Thrombosis, and Vascular Biology, vol. 26, No. 11, pp. 2552-2559.
Winter, et al. (Jun. 1, 1993) "Humanized Antibodies", Immunology Today, vol. 14, No. 6, pp. 243-246.
Wong, et al. (May 1-4, 2014) "Residual Dyslipidemia According to LDL-C, non-HDL-C and Apolipoprotein B by Cardiovascular Risk Category in Statin Treated US Adults", Journal of Clinical Lipidology, vol. 8, No. 3, Presented as a poster presentation at the National Lipid Association Scientific Sessions, Orlando, Florida, USA, pp. 323-324.
Wu, et al. (Apr. 5, 1987) "Receptor-Mediated In Vitro Gene Transformation by a Soluble DNA Carrier System", Journal of Biological Chemistry, vol. 262, No. 10, pp. 4429-4432.
Yamashita, Sizuya (2013) "PCSK9 (Proprotein Convertase subtilisin/kexin Type 9)", Prevention of Arteriosclerosis, vol. 11, No. 4, pp. 101-105.
Zimmerman, Marj P. (Nov. 2015) "How Do PCSK9 Inhibitors Stack Up to Statins for Low-Density Lipoprotein Cholesterol Control?", American Health Drug Benefits, vol. 8, No. 8, pp. 436-442.
U.S. Appl. No. 14/896,196, filed Dec. 4, 2016, 2016/0115246, Apr. 28, 2016, U.S. Pat. No. 10,494,442, Dec. 3, 2019, William J. Sasiela, Methods for Inhibiting Atherosclerosis by Administering an Inhibitor of PCSK9.
U.S. Appl. No. 16/505,074, filed Jul. 8, 2019, 2020/0071422, Mar. 5, 2020, U.S. Pat. No. 10,995,150, May 4, 2021, William J. Sasiela, Methods for Inhibiting Atherosclerosis by Administering an Inhibitor of PCSK9.
U.S. Appl. No. 14/511,975, filed Oct. 10, 2014, 2015/0140002, May 21, 2015, Marie Baccara-Dinet, Use Of A PCSK9 Inhibitor To Treat Hyperlipidemia.

(56) References Cited

OTHER PUBLICATIONS

U.S. Appl. No. 13/982,381, filed Jul. 29, 2013, 2014/0178402, Jun. 26, 2014, U.S. Pat. No. 9,682,013, Jun. 20, 2017, Corinne Hanotin, Pharmaceutical Compositions Comprising Human Antibodies To PCSK9.
U.S. Appl. No. 13/982,373, filed Jul. 29, 2013, 2014/0154262, Jun. 5, 2014, U.S. Pat. No. 9,561,155, Feb. 7, 2017, Corinne Hanotin, Method Of Reducing Cholesterol Levels Using A Human Anti-PCSK9 Antibody.
U.S. Appl. No. 16/365,317, filed Mar. 26, 2019, 2019/0343719, Nov. 14, 2019, U.S. Pat. No. 11,246,925, Feb. 15, 2022, Corinne Hanotin, Human Antibodies To PCSK9 For Use In Methods Of Treating Particular Groups Of Subjects.
U.S. Appl. No. 17/560,402, filed Dec. 23, 2021, 2022/0218823, Jul. 14, 2022, Corinne Hanotin, Human Antibodies To PCSK9 For Use In Methods Of Treating Particular Groups Of Subjects.
U.S. Appl. No. 14/539,199, filed Nov. 12, 2014, 2015/0152191, Jun. 4, 2015, U.S. Pat. No. 10,428,157, Oct. 1, 2019, Marie Baccara-Dinet, Dosing Regimens For Use With PCSK9 Inhibitors.
U.S. Appl. No. 16/415,837, filed May 17, 2019, 2020/0024364, Jan. 23, 2020, Marie Baccara-Dinet, Dosing Regimens For Use With PCSK9 Inhibitors.
U.S. Appl. No. 14/801,384, filed Jul. 16, 2015, 2016/0137745, May 19, 2016, U.S. Pat. No. 10,544,232, Jan. 28, 2020, Marie Baccara-Dinet, Methods For Treating Patients With Heterozygous Familial Hypercholesterolemia (heFH) With an Anti-PCSK9 Antibody.
U.S. Appl. No. 16/707,492, filed Dec. 9, 2019, 2020/0216565, Jul. 9, 2020, U.S. Pat. No. 11,306,155, Apr. 19, 2022, Marie Baccara-Dinet, Methods For Treating Patients With Heterozygous Familial Hypercholesterolemia (heFH) With an Anti-PCSK9 Antibody.
U.S. Appl. No. 17/693,837, filed Mar. 14, 2022, 2022/0315669, Oct. 6, 2022, Marie Baccara-Dinet, Methods For Treating Patients With Heterozygous Familial Hypercholesterolemia (heFH) With an Anti-PCSK9 Antibody.
U.S. Appl. No. 14/657,192, filed Mar. 13, 2015, 2015/0284473, Oct. 8, 2015, Laurence Bessac, Methods For Reducing Cardiovascular Risk.
U.S. Appl. No. 17/504,921, filed Oct. 19, 2021, 2022/0144969, May 12, 2022, Laurence Bessac, Methods For Reducing Cardiovascular Risk.
U.S. Appl. No. 12/637,942, filed Dec. 15, 2009, 2010/0166768, Jul. 1, 2010, U.S. Pat. No. 8,062,640, Nov. 22, 2011, Mark W. Sleeman, High Affinity Human Antibodies to PCSK9.
U.S. Appl. No. 13/095,234, filed Apr. 27, 2011, 2011/0256148, Oct. 20, 2011, U.S. Pat. No. 8,357,371, Jan. 22, 2013, Mark W. Sleeman, Methods for Treating Hypercholesterolemia Using Antibodies to PCSK9.
U.S. Appl. No. 14/100,992, filed Dec. 9, 2013, 2014/0099312, Apr. 10, 2014, U.S. Pat. No. 9,724,411, Aug. 8, 2017, Mark W. Sleeman, Methods for Treating Hypercholesterolemia and Reducing LDL-C Using Antibodies to PCSK9.
U.S. Appl. No. 12/949,846, filed Nov. 19, 2010, 2011/0065902, Mar. 17, 2011, U.S. Pat. No. 8,501,184, Aug. 6, 2013, Mark W. Sleeman, High Affinity Human Antibodies to PCSK9.
U.S. Appl. No. 14/737,488, filed Jun. 12, 2015, 2015/0284474, Oct. 8, 2015, U.S. Pat. No. 9,550,837, Jun. 24, 2017, Mark W. Sleeman, Therapeutic Uses Of Anti-PCSK9 Antibodies.
U.S. Appl. No. 15/377,364, filed Dec. 13, 2016, 2017/0096496, Apr. 6, 2017, U.S. Pat. No. 10,023,654, Jul. 17, 2018, Mark W. Sleeman, Anti-PCSK9 Antibodies.
U.S. Appl. No. 15/996,773, filed Jun. 4, 2018, 2019/0135941, May 9, 2019, U.S. Pat. No. 10,941,210, Mar. 9, 2021, Mark W. Sleeman, Anti-PCSK9 Antibodies.
U.S. Appl. No. 17/160,634, filed Jan. 28, 2021, 2021/0253735, Aug. 19, 2021, Mark W. Sleeman, Anti-PCSK9 Antibodies.
U.S. Appl. No. 13/559,862, filed Jul. 27, 2012, 2013/0189277, Jul. 25, 2013, U.S. Pat. No. 8,795,669, Aug. 5, 2014, Scott M. Walsh, Stabilized Formulations Containing Anti-PCSK9 Antibodies.
U.S. Appl. No. 14/319,730, filed Jun. 30, 2014, 2014/0341928, Nov. 20, 2014, U.S. Pat. No. 9,193,801, Nov. 24, 2015, Scott M. Walsh, Stabilized Formulations Containing Anti-PCSK9 Antibodies.
U.S. Appl. No. 15/603,732, filed May 24, 2017, 2018/0044436, Feb. 15, 2018, U.S. Pat. No. 10,472,425, Nov. 12, 2019, Scott M. Walsh, Stabilized Formulations Containing Anti-PCSK9 Antibodies.
U.S. Appl. No. 16/384,298, filed Apr. 15, 2019, 2019/0284301, Sep. 19, 2019, U.S. Pat. No. 10,752,701, Aug. 25, 2020, Scott M. Walsh, Stabilized Formulations Containing Anti-PCSK9 Antibodies.
U.S. Appl. No. 16/930,595, filed Jul. 16, 2020, 2021/0054100, Feb. 25, 2021, Scott M. Walsh, Stabilized Formulations Containing Anti-PCSK9 Antibodies.
U.S. Appl. No. 13/611,405, filed Sep. 12, 2012, 2013/0243784, Sep. 19, 2013, U.S. Pat. No. 10,076,571, Sep. 18, 2018, Gary Swergold, Methods for Reducing Lipoprotein(a) Levels by Administering an Inhibitor of Proprotein Convertase Subtilisin Kexin-9 (PCSK9).
U.S. Appl. No. 16/053,448, filed Aug. 2, 2018, 2018/0333490, Nov. 22, 2018, U.S. Pat. No. 11,116,839, Sep. 14, 2021, Gary Swergold, Methods for Reducing Lipoprotein(a) Levels by Administering an Inhibitor of Proprotein Convertase Subtilisin Kexin-9 (PCSK9).
U.S. Appl. No. 14/290,544, filed May 29, 2014, 2014/0356371, Dec. 4, 2014, U.S. Pat. No. 10,111,953, Oct. 30, 2018, Gary Swergold, Methods For Reducing Remnant Cholesterol And Other Lipoprotein Fractions By Administering An Inhibitor Of Proprotein Convertase Subtilisin Kexin-9 (PCSK9).
U.S. Appl. No. 16/662,313, filed Oct. 24, 2019, 2020/0255544, Aug. 13, 2020, Corinne Hanotin, Methods For Treating High Cardiovascular Risk Patients With Hypercholesterolemia.
U.S. Appl. No. 16/004,126, filed Jun. 8, 2018, 2019/0031774, Jan. 31, 2019, Maja Bujas-Bobanovic, Methods For Treating Hyperlipidemia In Diabetic Patients By Administering A PCSK9 Inhibitor.
U.S. Appl. No. 16/294,635, filed Mar. 6, 2019, 2019/0292273, Sep. 26, 2019, Corinne Hanotin, Methods For Reducing Cardiovascular Risk.
U.S. Appl. No. 15/238,890, filed Aug. 17, 2016, 2017/0049886, Feb. 23, 2017, U.S. Pat. No. 10,772,956, Sep. 15, 2020, Robert C. Pordy, Methods For Reducing Or Eliminating The Need For Lipoprotein Apheresis In Patients With Hyperlipidemia By Administering Alirocumab.
U.S. Appl. No. 16/991,269, filed Aug. 12, 2020, 2021/0100900, Apr. 8, 2021, Robert C. Pordy, Methods For Reducing Or Eliminating The Need For Lipoprotein Apheresis In Patients With Hyperlipidemia By Administering Alirocumab.
(Dec. 13, 2016) "Odyssey Long Term", Wiki journal club.
(Jul. 2005) "Guidance for Industry Estimating the Maximum Safe Starting Dose in Initial Clinical Trials for Therapeutics in Adult Healthy Volunteers", U.S. Department of Health and Human Services Food and Drug Administration Center for Drug Evaluation and Research (CDER), FDA Journal, XP055152598, 30 pages.
(Sep. 1, 1975) "A Classification and Outline of Cerebrovascular Diseases II", Advisory Council for the National Institute of Neurological and Communicative Disorders and Stroke, vol. 6, No. 5, pp. 564-616.
AACE Guidelines, "American Association of Clinical Endocrinologists' Guidelines for Management of Dyslipidemia and Prevention of Atherosclerosis", Endocrine Practice, Mar./Apr. 2012, 18(Suppl 1): 1-78.
Abdallah et al. (Jun. 2016) "Ipilimumab-Induced Necrotic Myelopathy in a Patient with Metastatic Melanoma: A Case Report and Review of Literature", Journal of Oncology Pharmacy Practice, vol. 22, No. 3, pp. 537-542.
Al-Mashhadi et al., "Familial hypercholesterolemia and atherosclerosis in clones minipigs created by DNA transposition of a human PCSK9 gain-of-function mutant", Sci Transl Med, 2; 5(166):44-53, (2013).
American College of Cardiology Press Release available at: https://www.acc.org/about-acc/press-releases/2018/03/09/16/08/sat-9am-et-alirocumab-reduces-cardiovascular-events-after-acute-coronary-syndrome, Mar. 10, 2018.
American Diabetes Association (Jan. 2012) Standards of Medical Care in Diabetes—2012, Diabetes Care, vol. 35, Supplement 1, pp. S11-S63.

(56) References Cited

OTHER PUBLICATIONS

Amit et al., "Three-Dimensional Structure of an Antigen-Antibody Complex at 2.8 a Resolution" Science (Aug. 1986) 233:747-753.
Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016].
Antonopoulos, et al. (Apr. 2012) "Statins as Anti-Inflammatory Agents in Atherogenesis: Molecular Mechanisms and Lessons from the Recent Clinical Trials", Current Pharmaceutical Drugs, vol. 18, No. 11, pp. 1519-1530.
Attarwala (Jul. 1, 2010) "TGN1412: From Discovery to Disaster", Journal of young pharmacists, vol. 2, No. 3, XP055407473, pp. 332-336.
Australian Public Assessment Report for Alirocumab (rch) (2016) Australian Government Department of Health, Therapeutic Goods Administration. Sponsor: Sanofi-Aventis Australia Pty Ltd, 93 pages.
Bambauer et al. (2003) "Low-density Lipoprotein Apheresis: An Overview," Therapeutic Apherisis and Dialysis. 7(4):382-390.
Barter, et al. (Nov. 2007,) "Effects of Torcetrapib in Patients at High Risk for Coronary Events", The New England Journal of Medicine, vol. 357, No. 21, pp. 2109-2122.
Beliard et al. (Mar. 3, 2014) "Improvement in LDL-cholesterol levels of patients with familial hypercholesterolemia: can we do better? Analysis of results obtained during the past two decades in 1669 French subjects," Atherosclerosis. 234:136-141.
Benjannet, et al., "NARC-1/PCSK9 and its Natural Mutants: Zymogen Cleavage and Effects on the Low Density Lipoprotein (LDL) Receptor and LDL Cholesterol", Journal of Biological Chemistry, vol. 279, No. 47, pp. 48865-48875, Sep. 9, 2004.
Bhatt et al. (May 2009) "The Use of Vectors Based on Gene Amplification for The Expression of Cloned Genes Mammalian Cells", European Heart Journal, vol. 30, Issue 10, pp. 1195-1202.
Boersma et al. (2011) "DARPins and other repeat protein scaffolds: advances in engineering and applications," Current Opinion in Biotechnology, 22:849-857.
Boerwinkle et al. (1992) "Apolipoprotein(a) Gene Accounts for Greater Than 90% of the Variation in Plasma Lipoprotein(a) Concentrations," J. Clin. Invest. 90:52-60.
Boes, et al., "Accelerated Development of IgG Autoantibodies and Autoimmune Disease in the Absence of Secreted IgM", Proceedings of the National Academy of Sciences, vol. 97, No. 3, pp. 1184-1189, 2000.
Borberg (Apr. 2013) "The lower the better: Target values after LDL-Apheresis and semi-selective LDL-elimination therapies," Transfusion and Apheresis Science. 48:203-206.
ClinicalTrials.gov (Oct. 22, 2015) Efficacy and Safety of Alirocumab Versus Placebo on Top of Maximally Tolerated Lipid Lowering Therapy in Patients With Hypercholesterolemia Who Have Type 1 or Type 2 Diabetes and Are Treated With Insulin (Odyssey DM—Insulin), ClinicalTrials.gov Identifier: NCT02585778.
ClinicalTrials.gov, "Odyssey Outcomes: Evaluation of Cardiovascular Outcomes After an Acute Coronary Syndrome During Treatment With Alirocumab", ClinicalTrials.gov Identifier: NCT01663402, https://clinicaltrials.gov/archive/NCT01663402/2012_08_10, (Aug. 10, 2012).
ClinicalTrials.gov, (Aug. 12, 2013) "Efficacy and Safety of Alirocumab (SAR236553/REGN727) Versus Placebo on Top of Lipid-Modifying Therapy in Patients With Heterozygous Familial Hypercholesterolemia (Odyssey High FH)", ClinicalTrials.gov Identifier: NCT01617655, https://clinicaltrials.gov/archive/NCT01617655/2013_08_12.
ClinicalTrials.gov, (Aug. 20, 2014) "A Study of Alirocumab (REGN727/SAR236553) in Patients With ADH and GOFm of the PCSK9 Gene or LOFm of the apoB Gene", ClinicalTrials.gov Identifier: NCT01604824, https://clinicaltrials.gov/archive/NCT01604824/2014_08_20.
ClinicalTrials.gov, (Aug. 7, 2014) "Long-term Safety and Tolerability of Alirocumab (SAR236553/REGN727) Versus Placebo on Top of Lipid-Modifying Therapy in High Cardiovascular Risk Patients With Hypercholesterolemia (Odyssey Long Term)", ClinicalTrials.gov Identifier: NCT01507831, https://clinicaltrials.gov/archive/NCT01507831/2014_08_07.
ClinicalTrials.gov, (Dec. 22, 2014) "Study of Alirocumab (REGN727/SAR236553) in Patients With Heterozygous Familial Hypercholesterolemia (HeFH) Undergoing Low-density Lipoprotein (LDL) Apheresis Therapy (Odyssey Escape)", ClinicalTrials.gov Identifier: NCT02326220, https://clinicaltrials.gov/ct2/show/NCT02326220?term=NCT02326220&rank=1.
ClinicalTrials.gov, (Dec. 27, 2013) "Phase III Study To Evaluate Alirocumab in Patients With Hypercholesterolemia Not Treated With a Statin (Odyssey Choice II)", ClinicalTrials.gov Identifier: NCT02023879, https://clinicaltrials.gov/archive/NCT02023879/2013_12_27.
ClinicalTrials.gov, (Feb. 1, 2011) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, https://clinicaltrials.gov/archive/NCT01288469/2011_02_01.
ClinicalTrials.gov, (Feb. 1, 2015) "Study of Alirocumab (REGN727/SAR236553) in Patients With heFH (Heterozygous Familial Hypercholesterolemia) Who Are Not Adequately Controlled with Their LMT (Lipid-Modifying Therapy) (Odyssey FH II)", ClinicalTrials.gov Identifier: NCT01709500, https://clinicaltrials.gov/archive/NCT01709500/2015_02_01.
ClinicalTrials.gov, (Feb. 1, 2015) "Study of Alirocumab (REGN727/SAR236553) in Patients with Primary Hypercholesterolemia and Moderate, High, or Very High Cardiovascular (CV) Risk, Who Are Intolerant to Statins (Odyssey Alternative)", ClinicalTrials.gov Identifier: NCT01709513, https://clinicaltrials.gov/archive/NCT01709513/2015_02_01.
ClinicalTrials.gov, (Feb. 18, 2014) "A Study of Alirocumab (REGN727/SAR236553) in Patients with ADH and GOFm of the PCSK9 Gene or LOFm of the apoB Gene", ClinicalTrials.gov Identifier: NCT01604824, https://clinicaltrials.gov/archive/NCT01604824/2014_02_18.
ClinicalTrials.gov, (Feb. 18, 2015) "Odyssey Outcomes: Evaluation of Cardiovascular Outcomes After an Acute Coronary Syndrome During Treatment with Alirocumab", ClinicalTrials.gov Identifier: NCT01663402, https://clinicaltrials.gov/archive/NCT01663402/2015_02_18.
ClinicalTrials.gov, (Feb. 24, 2015) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, https://clinicaltrials.gov/archive/NCT01644175/2015_02_24.
ClinicalTrials.gov, (Feb. 26, 2015) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2015_02_26>>.
ClinicalTrials.gov, (Feb. 26, 2015) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, https://clinicaltrials.gov/archive/NCT01617655/2015_02_26.
ClinicalTrials.gov, (Feb. 26, 2015) "Efficacy and Safety of Alirocumab (SAR236553/REGN727) Versus Placebo on Top of Lipid-Modifying Therapy in Patients with Heterozygous Familial Hypercholesterolemia Not Adequately Controlled With Their Lipid-Modifying Therapy", ClinicalTrials.gov Identifier: NCT01623115, https://clinicaltrials.gov/archive/NCT01623115/2015_02_26.
ClinicalTrials.gov, (Feb. 3, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_02_03>>.

(56) References Cited

OTHER PUBLICATIONS

ClinicalTrials.gov, (Jan. 10, 2012) "Long-term Safety and Tolerability of Alirocumab (SAR236553/REGN727) Versus Placebo on Top of Lipid-Modifying Therapy in High Cardiovascular Risk Patients with Hypercholesterolemia (Odyssey Long Term)", ClinicalTrials.gov Identifier: NCT01507831, https://clinicaltrials.gov/archive/NCT01507831/2012_01_10.
ClinicalTrials.gov, (Jan. 12, 2012) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2012_01_12>>.
ClinicalTrials.gov, (Jan. 22, 2015) "Long-term Safety and Tolerability of Alirocumab (SAR236553/REGN727) Versus Placebo on Top of Lipid-Modifying Therapy in High Cardiovascular Risk Patients with Hypercholesterolemia (Odyssey Long Term)", ClinicalTrials.gov Identifier: NCT01507831, Retrieved from: <<https://clinicaltrials.gov/archive/NCT01507831/2015_01_22>>.
ClinicalTrials.gov, (Jan. 24, 2013) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2013_01_24>>.
ClinicalTrials.gov, (Jan. 26, 2015) "Previous Study | Return to List | Next Study Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082/2015_01_26>>.
ClinicalTrials.gov, (Jan. 29, 2015) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2015_01_29>>.
ClinicalTrials.gov, (Jan. 29, 2015) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2015_01_29>>.
ClinicalTrials.gov, (Jan. 29, 2015) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2015_01_29>>.
ClinicalTrials.gov, (Jan. 29, 2015) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, Retrieved from: <<https://clinicaltrials.gov/archive/NCT01288469/2015_01_29>>.
ClinicalTrials.gov, (Jan. 29, 2015) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2015_01_29>>.
ClinicalTrials.gov, (Jan. 30, 2014) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2014_01_30>>.
ClinicalTrials.gov, (Jul. 10, 2015) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2015_07_10>>.
ClinicalTrials.gov, (Jul. 12, 2010) "Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082/2010_07_12>>.
ClinicalTrials.gov, (Jul. 17, 2012) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2012_07_17>>.
ClinicalTrials.gov, (Jul. 17, 2012) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2012_07_17>>.
ClinicalTrials.gov, (Jul. 18, 2012) "Efficacy and Safety of Alirocumab (SAR236553/REGN727) Versus Ezetimibe in Patients with Hypercholesterolemia (Odyssey Mono)", ClinicalTrials.gov Identifier: NCT01644474, <<https://clinicaltrials.gov/archive/NCT01644474/2012_07_18>>.
ClinicalTrials.gov, (Jul. 18, 2013) "Efficacy and Safety of Alirocumab (SAR236553/REGN727) Versus Ezetimibe in Patients with Hypercholesterolemia (Odyssey Mono)", ClinicalTrials.gov Identifier: NCT01644474, Retrieved from: <<https://clinicaltrials.gov/archive/NCT01644474/2013_07_18>>.
ClinicalTrials.gov, (Jul. 18, 2013) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2013_07_18>>.
ClinicalTrials.gov, (Jul. 2, 2013) "Efficacy and Safety Evaluation of Alirocumab (SAR236553/REGN727) in Patients with Primary Hypercholesterolemia on Stable Atorvastatin Therapy", ClinicalTrials.gov Identifier: NCT01288443, Retrieved from: <<https://clinicaltrials.gov/archive/NCT01288443/2013_07_02>>.
ClinicalTrials.gov, (Jul. 2, 2013) "Efficacy and Safety Evaluation of Alirocumab (SAR236553/REGN727) When Co-administered with High Dose of Atorvastatin in Patients with Primary Hypercholesterolemia", ClinicalTrials.gov Identifier: NCT01288469, Retrieved from: <<https://clinicaltrials.gov/archive/NCT01288469/2013_07_02>>.
ClinicalTrials.gov, (Jul. 22, 2014) "Package Insert for Proplex T Factor IX Complex Heat Treated (Baxter)", ClinicalTrials.gov Identifier: NCT02023879, Retrieved from: <<https://clinicaltrials.gov/archive/NCT02023879/2014_07_22>>.
ClinicalTrials.gov, (Jul. 8, 2014) "Efficacy and Safety of Alirocumab (SAR236553/REGN727) Versus Ezetimibe in Patients with Hypercholesterolemia (Odyssey Mono)", ClinicalTrials.gov Identifier: NCT01644474, Retrieved from: <<https://clinicaltrials.gov/archive/NCT01644474/2014_07_08>>.
ClinicalTrials.gov, (Jun. 10, 2014) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2014_06_10>>.
ClinicalTrials.gov, (Jun. 11, 2012) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2012_06_11>>.
ClinicalTrials.gov, (Jun. 18, 2012) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, Retrieved from: <<https://clinicaltrials.gov/archive/NCT01623115/2012_06_18>>.
ClinicalTrials.gov, (Jun. 18, 2015) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2015_06_18>>.
ClinicalTrials.gov, (Jun. 18, 2015) "Study of the Safety and Efficacy of REGN727/SAR236553 in Patients with HeFH Hypercholester-

(56) References Cited

OTHER PUBLICATIONS olemia", ClinicalTrials.gov Identifier: NCT01266876, Retrieved from: <<https://clinicaltrials.gov/archive/NCT01266876/2015_06_18>>.
ClinicalTrials.gov, (Jun. 19, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_06_19>>.
ClinicalTrials.gov, (Jun. 19, 2014) "Phase III Study to Evaluate Alirocumab in Patients with Hypercholesterolemia Not Treated With a Statin (Odyssey Choice II)", ClinicalTrials.gov Identifier: NCT02023879, Retrieved from: <<https://clinicaltrials.gov/archive/NCT02023879/2014_06_19>>.
ClinicalTrials.gov, (Jun. 27, 2013) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2013_06_27>>.
ClinicalTrials.gov, (Jun. 27, 2013) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, Retrieved from: <<https://clinicaltrials.gov/archive/NCT01623115/2013_06_27>>.
ClinicalTrials.gov, (Jun. 27, 2013) "Long-term Safety and Tolerability of Alirocumab (SAR236553/REGN727) Versus Placebo on Top of Lipid-Modifying Therapy in High Cardiovascular Risk Patients with Hypercholesterolemia (Odyssey Long Term)", ClinicalTrials.gov Identifier: NCT01507831, Retrieved from: <<https://clinicaltrials.gov/archive/NCT01507831/2013_06_27>>.
ClinicalTrials.gov, (Mar. 10, 2014) "Phase III Study to Evaluate Alirocumab in Patients With Hypercholesterolemia Not Treated With a Statin (Odyssey Choice II)", ClinicalTrials.gov Identifier: NCT02023879, Retrieved from: <<https://clinicaltrials.gov/archive/NCT02023879/2014_03_10>>.
ClinicalTrials.gov, (Mar. 15, 2013) "Efficacy and Safety Evaluation of Alirocumab (SAR236553/REGN727) in Patients with Primary Hypercholesterolemia on Stable Atorvastatin Therapy in Japan", ClinicalTrials.gov Identifier: NCT01812707, Retrieved from: <<https://clinicaltrials.gov/archive/NCT01812707/2013_03_15>>.
ClinicalTrials.gov, (Mar. 16, 2012) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2012_03_16>>.
ClinicalTrials.gov, (Mar. 26, 2015) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2015_03_26>>.
ClinicalTrials.gov, (Mar. 26, 2015) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, retrieved from: <<https://clinicaltrials.gov/archive/NCT01623115/2015_03_26>>.
ClinicalTrials.gov, (May 20, 2015) "Previous Study | Return to List | Next Study Phase III Study to Evaluate Alirocumab in Patients With Hypercholesterolemia Not Treated with a Statin (Odyssey Choice II)", ClinicalTrials.gov Identifier: NCT02023879, Retrieved from: <<https://clinicaltrials.gov/archive/NCT02023879/2015_05_20>>.
ClinicalTrials.gov, (May 21, 2013) "Study of Alirocumab (REGN727/SAR236553) in Patients With heFH (Heterozygous Familial Hypercholesterolemia) Who Are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2013_05_21>>.
ClinicalTrials.gov, (May 23, 2012) "A Study of Alirocumab (REGN727/SAR236553) in Patients with ADH and GOFm of the PCSK9 Gene or LOFm of the apoB Gene", ClinicalTrials.gov Identifier: NCT01604824, Retrieved from: <<https://clinicaltrials.gov/archive/NCT01604824/2012_05_23>>.
ClinicalTrials.gov, (May 28, 2014) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2014_05_28>>.
ClinicalTrials.gov, (Nov. 16, 2011) "Efficacy and Safety Evaluation of Alirocumab (SAR236553/REGN727) When Co-administered With High Dose of Atorvastatin in Patients with Primary Hypercholesterolemia", ClinicalTrials.gov Identifier: NCT01288469, Retrieved from: <<https://clinicaltrials.gov/archive/NCT01288469/2011_11_16>>.
ClinicalTrials.gov, (Nov. 18, 2011) "Study of the Safety and Efficacy of REGN727/SAR236553 in Patients with HeFH Hypercholesterolemia", ClinicalTrials.gov Identifier: NCT01266876, Retrieved from: <<https://clinicaltrials.gov/archive/NCT01266876/2011_11_18>>.
ClinicalTrials.gov, (Nov. 7, 2011) "Ascending Multi-dose Study of REGN727(SAR236553) With and Without Concomitant Atorvastatin", ClinicalTrials.gov Identifier: NCT01161082, Retrieved from: <<https://clinicaltrials.gov/archive/NCT01161082/2011_11_07>>.
ClinicalTrials.gov, (Oct. 1, 2014) "Efficacy and Safety of Alirocumab (SAR236553/REGN727) Versus Placebo on Top of Lipid-Modifying Therapy in Patients with High Cardiovascular Risk and Hypercholesterolemia (Odyssey Combo I)", ClinicalTrials.gov Identifier: NCT01644175, Retrieved from: <<https://clinicaltrials.gov/archive/NCT01644175/2014_10_01>>.
ClinicalTrials.gov, (Oct. 17, 2012) "Study of Alirocumab (REGN727/SAR236553) in Patients With heFH (Heterozygous Familial Hypercholesterolemia) Who Are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2012_10_17>>.
ClinicalTrials.gov, (Oct. 17, 2012) "Study of Alirocumab (REGN727/SAR236553) in Patients with Primary Hypercholesterolemia and Moderate, High, or Very High Cardiovascular (CV) Risk, Who Are Intolerant to Statins (Odyssey Alternative)", ClinicalTrials.gov Identifier: NCT01709513, Retrieved from: <<https://clinicaltrials.gov/archive/NCT01709513/2012_10_17>>.
ClinicalTrials.gov, (Oct. 22, 2013) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2013_10_22>>.
ClinicalTrials.gov, (Oct. 25, 2013) "Study of Alirocumab (REGN727/SAR236553) in Patients With heFH (Heterozygous Familial Hypercholesterolemia) Who Are Not Adequately Controlled with Their LMT (Lipid-Modifying Therapy) (Odyssey FH II)", ClinicalTrials.gov Identifier: NCT01709500, Retrieved from: <<https://clinicaltrials.gov/archive/NCT01709500/2013_10_25>>.
ClinicalTrials.gov, (Oct. 25, 2013) "Study to Evaluate the Efficacy and Safety of Every Four Weeks Treatment Regimen of Alirocumab (REGN727/SAR236553) in Patients with Primary Hypercholesterolemia (Odyssey Choice 1)", ClinicalTrials.gov Identifier: NCT01926782, Retrieved from: <<https://clinicaltrials.gov/archive/NCT01926782/2013_10_25>>.
ClinicalTrials.gov, (Oct. 27, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_10_27>>.
ClinicalTrials.gov, (Oct. 6, 2014) "Crystal Structure of The Complex of Rat Neonatal Fc Receptor With Fc", ClinicalTrials.gov

(56) References Cited

OTHER PUBLICATIONS

Identifier: NCT01663402, Retrieved from: <<https://clinicaltrials.gov/archive/NCT01663402/2014_10_06>>.
ClinicalTrials.gov, (Oct. 6, 2014) "Efficacy and Safety of Alirocumab (SAR236553/REGN727) Versus Placebo on Top of Lipid-Modifying Therapy in Patients with Heterozygous Familial Hypercholesterolemia (Odyssey High FH)", ClinicalTrials.gov Identifier: NCT01617655, Retrieved from: <<https://clinicaltrials.gov/archive/NCT01617655/2014_10_06>>.
ClinicalTrials.gov, (Oct. 6, 2014) "Efficacy and Safety of Alirocumab (SAR236553/REGN727) Versus Placebo on Top of Lipid-Modifying Therapy in Patients with Heterozygous Familial Hypercholesterolemia Not Adequately Controlled with Their Lipid-Modifying Therapy (Odyssey FH I)", ClinicalTrials.gov Identifier: NCT01623115, Retrieved from: <<https://clinicaltrials.gov/archive/NCT01623115/2014_10_06>>.
ClinicalTrials.gov, (Oct. 7, 2013) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2013_10_07>>.
ClinicalTrials.gov, (Oct. 7, 2013) "Odyssey Outcomes: Evaluation of Cardiovascular Outcomes After an Acute Coronary Syndrome During Treatment with Alirocumab", ClinicalTrials.gov Identifier: NCT01663402, Retrieved from: <<https://clinicaltrials.gov/archive/NCT01663402/2013_10_07>>.
ClinicalTrials.gov, (Oct. 7, 2013) "Study of Alirocumab (REGN727/SAR236553) in Patients with Primary Hypercholesterolemia and Moderate, High, or Very High Cardiovascular (CV) Risk, Who Are Intolerant to Statins (Odyssey Alternative)", ClinicalTrials.gov Identifier: NCT01709513, Retrieved from: <<https://clinicaltrials.gov/archive/NCT01709513/2013_10_07>>.
ClinicalTrials.gov, (Sep. 22, 2014) "Efficacy and Safety of Alirocumab (SAR236553/REGN727) Versus Ezetimibe on Top of Statin in High Cardiovascular Risk Patients with Hypercholesterolemia (Odyssey Combo II)", ClinicalTrials.gov Identifier: NCT01644188, Retrieved from: <<https://clinicaltrials.gov/archive/NCT01644188/2014_09_22>>.
ClinicalTrials.gov, "A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome", Archive from ClinicalTrials.gov for NCT01663402, Retrieved From: <<https://clinicaltrials.gov/archive/NCT01663402/2014_03_11>>, 3 Pages, Mar. 11, 2014.
ClinicalTrials.gov, "Efficacy and Safety Evaluation of Alirocumab (SAR236553/REGN727) in Patients With Primary Hypercholesterolemia on Stable Atorvastatin Therapy", ClinicalTrials.gov Identifier: NCT01288443, Retrieved From: <<https://clinicaltrials.gov/archive/NCT01288443/2011_02_01>>, Feb. 1, 2011.
ClinicalTrials.gov, "Study of the Safety and Efficacy of REGN727/SAR236553 in Patients With HeFH Hypercholesterolemia", ClinicalTrials.gov Identifier: NCT01266876, Retrieved From: <<https://clinicaltrials.gov/archive/NCT01266876/2010_12_23>>, Dec. 23, 2010.
Conroy, et al., "Estimation of Ten-Year Risk of Fatal Cardiovascular Disease in Europe: the SCORE Project", European Heart Journal, vol. 24, No. 11, pp. 987-1003. (2003).
Davignon, et al. (Jul. 11, 2010) "The Influence of PCSK9 Polymorphisms on Serum Low-Density Lipoprotein Cholesterol and Risk of Atherosclerosis", Current Atherosclerosis Reports, vol. 12, No. 5, pp. 308-315.
Della, et al. (Jun. 2017) "Alirocumab For the Treatment of Hypercholesterolaemia", Expert Review of clinical Pharmacology, vol. 10, No. 6, pp. 571-582.
Demant et al. (2001) "The metabolism of lipoprotein(a) and other apolipoprotein B-containing lipoproteins: a kinetic study in humans," Atherosclerosis 157:325-339.

Denis, et al., "Gene Inactivation of Proprotein Convertase Subtilisin/Kexin Type 9 Reduces Atherosclerosis in Mice", Circulation, vol. 125, No. 7, pp. 894-901, Feb. 21, 2012.
Do, et al., "PCSK9 Inhibitors: Potential in Cardiovascular Therapeutics", Current Cardiology Reports, vol. 15, No. 3, p. 345, Jan. 22, 2013.
Edwards, et al. (Nov. 14, 2003) "The Remarkable Flexibility of the Human Antibody Repertoire; Isolation of Over One Thousand Different Antibodies to a Single Protein, BLyS", Journal of Molecular Biology, vol. 334, No. 1, 103-118.
EPG Health press release, "Odyssey Outcomes trial success for Praluent in reduction of MACE events.—Sanofi + Regeneron", available at: https://www.epgonline.org/global/news/odyssey-outcomes-trial success-for-praluent-inreduction-of-mace-events-sanofi-regeneron-.html, Mar. 11, 2018.
European Office Action corresponding to European Patent Application No. 12701015.5, dated Apr. 24, 2015.
European Office Action corresponding to European Patent Application No. 12701015.5, dated May 30, 2014.
European Office Action corresponding to European Patent Application No. 12701742.4, dated Jun. 1, 2015.
European Office Action corresponding to European Patent Application No. 12701742.4, dated May 28, 2014.
European Public Assessment Report (EPAR) for Praluent ™, European Medicines Agency, 3 Pages, 2016.
Extended European Search Report for European Patent Application No. 21151675.2, dated Aug. 4, 2021.
Extended European Search Report received for European Application No. 19210918.9, dated Jun. 8, 2020.
Extended European Search Report received for European Application No. 19212291.9, dated May 18, 2020.
Extended European Search Report received for European Application No. 20174278.0, dated Nov. 10, 2020.
Extended European Search Report received in European Patent Application No. 16200305.7 dated Jun. 1, 2017.
Extended European Search Report received in European Patent Application No. 21185555.6 dated Mar. 21, 2022.
Ference, et al., Effect of Long-Term Exposure to Lower Low-Density Lipoprotein Cholesterol Beginning Early in Life on the Risk of Coronary Heart Disease, Journal of the American College of Cardiology, vol. 60, Issue 25, pp. 2631-2639, Dec. 25, 2012.
Ferrara, et al. (2015) "Recombinant Renewable Polyclonal Antibodies", mAbs, vol. 7, No. 1, pp. 32-41.
Gandek et al. (2004) "Psychometric evaluation of the SF-36 health survey in Medicare managed care," Health Care rinanc Rev. 25(4):5-25.
Genentech (2014) Actemra Subcutaneous Dosing & Administration Pocket Guide, pp. 1-40.
Gershoni et al. (Jan. 2007) "Epitope mapping—The first step in developing epitope-based vaccines," Biod, Adis International Ltd, NZ, vol. 21, No. 3, pp. 145-156.
Giugliano, et al. (Oct. 28, 2017) "Clinical Efficacy and Safety of Achieving Very Low LDL-Cholesterol Concentrations with the PCSK9 Inhibitor Evolocumab: A Prespecified Secondary Analysis of the FOURIER Trial", LANCET (North American Edition), vol. 390, No. 10106, pp. 1962-1971.
Gouni-Berthold, et al., "PCSK9 Antibodies for the Treatment of Hypercholesterolemia", Nutrients, vol. 6, No. 12, pp. 5517-5533. (2014).
Healio.com, "PCSK9 inhibitors poised for breakthrough as new cholesterol-lowering therapy", Cardiology Today, Apr. 2013, Retrieved from url: https://www.healio.com/news/cardiology/20130411/10_3928_1081_597x_20130101_00_1098093.
Himmler, et al., "Modelling the Societal Impact of IMirocumab in Patients with Severe Hypercholesterolemia Treated with Apheresis in Germany", Value in Health, vol. 20, Abstract No. PCV70, 1 Page. (2017).
Hirsch et al. (Mar. 2006) "ACC/AHA 2005 Practice Guidelines for the Management of Patients with Peripheral Arterial Disease (Lower Extremity, Renal, Mesenteric, and Abdominal Aortic)", Circulation, vol. 113, No. 11, pp. 1475-1547.

(56) References Cited

OTHER PUBLICATIONS

Huijgen et al. (2010) "Two years after molecular diagnosis of familial hypercholesterolemia: majority on cholesterol-lowering treatment but a minority reaches treatment goal," PLoS One. 5(2):e9220. pp. 1-7.
International Nonproprietary Names for Pharmaceutical Substances (INN) WHO Drug Information, vol. 25, No. 4, 2011; 53 pages.
International Search Report and Written Opinion for PCT International Patent Application No. PCT/EP2012/057890, dated Aug. 28, 2012.
International Search Report and Written Opinion for PCT International Patent Application No. PCT/EP2015/055369, dated May 21, 2015.
International Search Report and Written Opinion for PCT International Patent Application No. PCT/IB2018/054182, dated Aug. 31, 2018.
International Search Report and Written Opinion for PCT International Patent Application No. PCT/US2009/068013, dated May 12, 2010.
International Search Report and Written Opinion for PCT International Patent Application No. PCT/US2019/021034, dated Jun. 27, 2016.
Julius, "Current Role of Lipoprotein Apheresis in the Treatment of High-Risk Patients", Journal of Cardiovascular Development and Disease, vol. 5, No. 27, pp. 1-11. (2018).
Julius, et al., "Effects of Lipoprotein Apheresis on PCSK9 Levels", Atherosclerosis Supplements, vol. 18, pp. 180-186. (2015).
Kastelein et al. (Sep. 1, 2015) "Odyssey FH I and FH II: 78-week results with alirocumab treatment in 735 patients with heterozygous familial hypercholesterolemia," Eur Heart J. 36(43):2996-3003.
Keene, et al. (Jul. 2014) "Effect on Cardiovascular Risk of High Density Lipoprotein Targeted Drug Treatments of Niacin, Fibrates, and CETP Inhibitors: Meta-Analysis of Randomised Controlled Trials Including 117411 Patients", British Medical Journal, vol. 349, No. g4379, pp. 1-13.
Kereiakes et al. (Mar. 13, 2015) "Efficacy and safety of the PCSK9 inhibitor alirocumab among high cardiovascular risk patients on maximally tolerated statin therapy: the Odyssey Combo I study," Am Heart J. 169(6):906-915.
Koschinsky et al. (2009) In; Clinical Lipidology: A Companion to Braunwald's Heart Disease. Ed: Ballantyne, pp. 136-143.
Kühnast et al. (2012) "Aliskiren Inhibits Atherosclerosis Development and Imrpoves Plaque Stability in APOE*3Leiden.CETP Transgenic Mice with or without Treatment with Atorvastatin," J. Hypertens, 30(1):21-41.
Kühnast et al. (2013) "Niacin Reduces Atherosclerosis Development in APOE*3Leiden.CETP Mice Mainly by Reducing NonHDL-Cholesterol," Plos One, 8(6):e66467, 13 pages.
Kwon, et al., "Molecular Basis for LDL Receptor Recognition by PCSK9" Proceedings of the National Academy of Sciences, vol. 105, No. 6, pp. 1820-1825, 2008.
Kyratsous, et al., "Reply to Dimitrov Et al.: VelociSuite Technologies Are a Foundation for Rapid Therapeutic Antibody Development", Proceedings of the National Academy of Sciences, vol. 112, No. 37, pp. E5116-E5116, 2015.
Lederman, Lynne, Monoclonal Antibody to PCSK9 Offers New Approach to Treating Hypercholesterolemia, In MD Conference Express, vol. 13, No. 7, pp. 16-17, Aug. 31, 2013.
Lee et al. (2018) "How to Interpret Recent CV Outcome Trials and Future: PCSK9 Inhibitors", Journal of Lipid and Atherosclerosis, 7(1):1-11.
Leebmann et al. (Dec. 17, 2013) Circulation "Lipoprotein Apheresis in Patients With Maximally Tolerated Lipid-Lowering Therapy, Lipoprotein(a)-Hyperlipoproteinemia, and Progressive Cardiovascular Disease," Circulation. 128(24):2567-2576.
Leiter, et al. (Dec. 2017) "Efficacy and Safety of Alirocumab In Insulin-Treated Individuals with Type 1 Or Type 2 Diabetes and High Cardiovascular Risk: The Odyssey DM-Insulin Randomized Trial", Diabetes, Obesity & metabolism, vol. 19, No. 12, pp. 1781-1792.
Leiter, et al. (Jul. 1, 2017) "Lipid-Lowering Efficacy and Safety of Alirocumab In Patients with or without Diabetes: A Sub-Analysis of Odyssey Combo II", Diabetes, Obesity & Metabolism, vol. 19, No. 7, pp. 989-996.
Lo, et al., "Pathogenicity and Epitope Characteristics Do Not Differ in IgG Subclass-Switched Anti-Desmoglein 3 IgG1 and IgG4 Autoantibodies in Pemphigus Vulgaris", PLoS One, vol. 11, No. 6, 2016.
Maxwell, et al., Antibodies to PCSK9 A Superior Way to Lower LDL Cholesterol?, Circulation Research, vol. 111, No. 3, pp. 274-277, 2012.
McKee, "Praluent Slashes Need for Apheresis Treatment", PharmaTimes, 2 Pages. (Aug. 30, 2016).
Müller-Wieland, et al. (2017) "Design and Rationale of The Odyssey DM Dyslipidemia Trial: Lipid Lowering Efficacy and Safety of Alirocumab In Individuals with Type 2 Diabetes and Mixed Dyslipidaemia at High Cardiovascular Risk", Cardiovascular Diabetology, vol. 16, No. 70, pp. 1-10.
Murphy, et al., "Mice with Megabase Humanization of Their Immunoglobulin Genes Generate Antibodies as Efficiently as Normal Mice", Proceedings of the National Academy of Sciences, vol. 111, No. 14, pp. 5153-5158, 2014.
Nair, et al. (Jan. 1, 2016) "A simple practice guide for dose conversion between animals and human", Journal of Basic and Clinical Pharmacy, vol. 7, No. 2, pp. 27-31.
Neil et al. (2004) "Established and emerging coronary risk factors in patients with heterozygous familial hypercholesterolaemia," Heart. 90(12):1431-1437.
Ni et al. (2010) "A proprotein convertase subtilisin-like/kexin type 9 (PCSK9) C-terminal domain antibody antigen-binding fragment inhibits PCSK9 internalization and restores low density lipoprotein uptake," J Biol Chem. 285(17):12882-91.
Opposition from EP Application No. 09793408.7 dated Oct. 11, 2017.
Panka et al., "Variable Region Framework Differences Result in Decreased or Increased Affinity of Variant Anti-Digoxin Antibodies" Proc. Natl. Acad. Sci. USA (May 1988) 85:3080-3084.
Partial European Search Report received in European Patent Application No. 16200305.7 dated Feb. 28, 2017.
Partial European Search Report received in European Patent Application No. 21185555.6 dated Dec. 17, 2021.
Patro et al., "Protein formulation and fill-finish operations," Biotechnol Annu Rev, 8:55-84, (2002). Abstract only.
Pijlman et al. (2010) "Evaluation of cholesterol lowering treatment of patients with familial hypercholesterolemia: a large cross-sectional study in The Netherlands," Atherosclerosis. 209:189-194.
Post et al. (1999) "Acyl-Coenzyne A:Cholesterol Acyltransferase Inhibitor, Avasimibe, Stimulates Bile Acid Synthesis and Cholesterol 7α-Hydroxylase in Cultured Rat Hepatocytes and In Vitro in the Rat," Hepatology, 30(2):491-500.
Post et al. (2003) "Increased Fecal Bile Acid Excretion in Transgenic Mice With Elevated Expression of Human Phospholipid Transfer Protein," ArteriosclerThromb Vase Biol., 23:892-897.
Powchik (Jul. 15, 2010) Regeneron: Investor Day. pp. 1-19.
Press Release, Online, Sankyo Co., Ltd., Retrieved From: <<https://www.sanofi.co.jp/-/media/Project/One-Sanofi-Web/Websites/Asia-Pacific/Sanofi-JP/Home/press-releases/PDF/2012/20121112.pdf>>, Nov. 12, 2012.
Presta (2006) "Engineering of Therapeutic Antibodies to Minimize Immunogenicity and Optimize Function", Advanced Drug Delivery Reviews, pp. 640-656.
Ray, et al. (Dec. 13, 2016) "Reductions in Atherogenic Lipids and Major Cardiovascular Events: A Pooled Analysis of 10 Odyssey Trials Comparing Alirocumab With Control", Circulation, vol. 134, No. 24, pp. 1931-1943.
Redlich et al., "Inflammatory bone loss: pathogenesis and therapeutic intervention", Nat Rev Drug Discov., Mar. 2012, 11(3): 234-250.
Regeneron and Sanofi (Nov. 5, 2012) "IR Conference Call on PCSK9: SAR236553/REGN727 PCSK9 Antibody for Hypercholesterolemia Phase 3 Odyssey Program Underway," Accessible on the Internet at URL: www.sanofi.com/Images/31341_2012-11-05_PCSK9_call.pdf. pp. 1-30. [Last Accessed on Sep. 5, 2017].

(56) References Cited

OTHER PUBLICATIONS

Regeneron Pharmaceuticals (Nov. 5, 2012)"Sanofi and Regeneron Announce Patient Enrollment in Cardiovascular Outcome Trial with Antibody to PCSK9 for Hypercholesterolemia," Press Release. Acquire Media.
Regeneron Pharmaceuticals, Inc. (Jun. 12, 2014) "Sanofi and Regeneron announce new, detailed data from positive sarilumab phase 3 rheumatoid arthritis trial at EULAR," Press Release. Acquire Media.
Reichert et al. (Jan. 1, 2011) "Antibody-based therapeutics to watch in 2011," MAbs. 3:76-99.
Response to Third Party Oppositions corresponding to European Patent Application No. 12761864.3, dated Dec. 9, 2016.
Robinson et al. (2013) "Management of Familial Hypercholesterolemia: A Review of the Recommendations from the National Lipid Association Expert Panel on Familial Hypercholesterolemia," J. Manag. Care Pharm. 19(2):139-149.
Rose-John, et al. (May 17, 2006) "Interleukin-6 Biology is Coordinated by Membrane-Bound and Soluble Receptors: Role in Inflammation and Cancer", Journal of Leukocyte Biology, vol. 80, No. 2, pp. 227-236.
Rudikoff, et al. (Mar. 1, 1982) "Single Amino Acid Substitution Altering Antigen-Binding Specificity", Proceedings of the National Academy of Sciences of the United States of America, vol. 79, pp. 1979-1983.
Sabatine et al., "Evolocumab and Clinical Outcomes in Patients with Cardiovascular Disease", NEJM, May 4, 2017, 376(18): 1713-1722.
Sabatine, et al. (Dec. 2017) "Cardiovascular Safety and Efficacy of The PCSK9 Inhibitor Evolocumab In Patients with and without Diabetes and The Effect of Evolocumab On Glycaemia and Risk of New-Onset Diabetes: A Prespecified Analysis of The FOURIER Randomised Controlled Trial", The Lancet Diabetes & Endocrinology, vol. 5, No. 12, pp. 941-950.
Sanofi "Sanofi and Regeneron Report Positive Top-line Results with Alirocumab from First Phase 3 Study of a PCSK9 Inhibitor for LDL Cholesterol Reduction", Retrieved From: <<https://investor.regeneron.com/news-releases/news-release-details/sanofi-and-regeneron-report-positive-top-line-results-alirocumab>>, 3 Pages. (Dec. 5, 2018).
Sarkar et al. (2002) "Rational cytokine design for increased lifetime and enhanced potency using pH-activated histidine switching," Nature Biotechnology 20:908-913.
Schafer, et al., "Failure is an Option: Learning from Unsuccessful Proof-of-Concept Trials", Drug Discovery Today, vol. 13, Issues 21-22, pp. 913-916, Nov. 2008.
Schiel, et al., "Four Years' Treatment Efficacy of Patients with Severe Hyperlipidemia. Lipid Lowering Drugs versus LDL-Apheresis", The International Journal of Artificial Organs, vol. 18, No. 12, pp. 786-793. (1995).
Schubert-Zsilavecz, et al., Better Blood Sugar Control In Diabetics. Insulin Glargin—A Long-Acting Insulin Analogue, Pharmazie in Unserer Zeit, vol. 30, No. 2 (English Translation), pp. 125-130, Jan. 2001.
Scott et al., "PCSK9 Inhibitors: Wearing FH Patients off Apheresis", MD Magazine, 2 Pages. (Aug. 29, 2016).
Sharrett, et al., "Coronary Heart Disease Prediction From Lipoprotein Cholesterol Levels, Triglycerides, Lipoprotein(A), Apolipoproteins A-I And B, And HDL Density Subfractions", Circulation, vol. 104, No. 10, pp. 1108-1113. (2001).
Sniderman, et al. (May 20, 2014) "The severe hypercholesterolemia phenotype: clinical diagnosis, management, and emerging therapies", Journal of the American College of Cardiology, vol. 3, No. 19, pp. 1935-1947.
Stary et al. (1995) "A Definition of Advanced Types of Atherosclerotic Lesions and a Histological Classification of Atherosclerosis," Arterioscler Thromb Vase Biol., vol. 15, 47 pages.

Stein et al. (Mar. 22, 2012) Protocol for "Effect of a monoclonal antibody to PCSK9 on LDL cholesterol," N Engl J Med 366(12):1108-1118.
Stein et al. (Mar. 22, 2012) Supplementary Appendix to "Effect of a monoclonal antibody to PCSK9 on LDL cholesterol," N Engl J Med 366(12):1108-1118.
Tavori et al. (Oct. 11, 2013) "Loss of Plasma Proprotein Convertase Subtilisin/Kevin 9 (PCSK9) After Lipoprotein Apheresis," Circulation Research. 113(12):1290-1295.
Taylor et al. (1992) "A transgenic mouse that expresses a diversity of human sequence heavy and light chain immunoglobulins," Nucleic Acids Research, 20(23):6287-6295.
The HPS2-Thrive Collaborative GR (Jul. 2014) "Effects of Extended-Release Niacin with Laropiprant in High-Risk Patients", The New England Journal of Medicine, vol. 371, No. 3, pp. 203-212.
Third Party Observations corresponding to European Patent Application No. 12761864.3, dated Jul. 7, 2017.
Third Party Observations received for European Patent Application No. 12761864.3, dated Feb. 24, 2016.
Third Party Opposition received for Colombian Patent Application No. 13203072, dated Dec. 13, 2013.
Third Party Opposition received for Guatemalan Patent Application No. A-2013-0186, dated Sep. 18, 2014.
Thomas, et al., "Clinical Development Success Rates 2006-2015", BIO Industry Analysis, 28 Pages, Jun. 2016.
Thompsen et al. (2006) "A systematic review of LDL apheresis in the treatment of cardiovascular disease," Atherosclerosis. 189:31-38.
Thygesen et al. (Oct. 16, 2012) "Third Universal Definition of Myocardial Infarction", Journal of the American College of Cardiology, vol. 60, No. 16, pp. 1581-1598.
Uchiyama, et al. (2008) "Tocilizumab, A Humanized Anti-Interleukin-6 Receptor Antibody, Ameliorates Joint Swelling in Established Monkey Collagen-Induced Arthritis", Biological and Pharmaceutical Bulletin, vol. 31, No. 6, pp. 1159-1163.
Van Bruggen et al., "Evolocumab's Long-Term Mortality Risk Unlear Due to Shortened Follow-Up of FOURIER", Amer Journ Cardio Drugs, 2022, 22: 5-8.
Van Wissen et al. (2003) "Long term statin treatment reduces lipoprotein(a) concentrations in heterozygous familial hypercholesterolaemia," Heart. 89(8):893-896.
Verschuren et al. (2005) "Effect of Low Dose Atorvastatin Versus Diet-Induced Cholesterol Lowering on Atherosclerotic Lesion Progression and Inflammation in Apolipoprotein E*3-Leiden Transgenic Mice," Arterioscler Thromb Vase. Biol., 25:161-167.
Villa, et al., "Ldl-C Lowering Efficacy of Evolocumab (Amg 145) Could Reduce Apheresis in Patients At High Risk for Cardiovascular Events in Germany", Value in Health, vol. 17, No. 7, pp. A504-A505. (2014).
Walji (2013) "Lipoprotein Apheresis for the Treatment of Familial Hypercholesterolemia," Clinical Lipidology. 8(5):573-586.
Warnick et al. (2008) "Standardization of Measurements for Cholesterol, Triglycerides, and Major Lipoproteins," Lab Med. 39(8):481-490.
Whalley et al. (1997) "Quality of life in rheumatoid arthritis," Br. J. Rheumatol. 36:884-888.
WHO (Jan. 1, 2012) "International Nonproprietary Names for Pharmaceutical Substances (INN)", World Health Organization, Drug Information, vol. 26, No. 4, pp. 401-471.
Yoshimura, et al. (2009) "Comprehensive Analysis of Inflammatory Immune Mediators in Vitreoretinal Diseases", PLoS One, vol. 4, No. 12, pp. 1-9.
Zhang, et al. (Apr. 11, 2018) "Usefulness of Alirocumab and Evolocumab for the Treatment of Patients with Diabetic Dyslipidemia", Proceedings, vol. 31, No. 2, pp. 180-184.

* cited by examiner

SEQUENCE LISTING

<160> NUMBER OF SEQ ID NOS: 9

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Asp Trp Val
        35                  40                  45

-continued

```
Ser Thr Ile Ser Gly Ser Gly Gly Thr Thr Asn Tyr Ala Asp Ser Val
        50                  55                  60

Lys Gly Arg Phe Ile Ile Ser Arg Asp Ser Ser Lys His Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Ser Asn Trp Gly Asn Phe Asp Leu Trp Gly Arg Gly Thr
            100                 105                 110

Leu Val Thr Val Ser Ser
            115

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Asn Asn Tyr Ala
 1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Gly Ser Gly Gly Thr Thr
 1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Asp Ser Asn Trp Gly Asn Phe Asp Leu
 1               5                  10

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Arg Asn Phe Leu Gly Trp Tyr Gln Gln Lys Pro Gly Gln
        35                  40                  45
```

```
Pro Pro Asn Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Tyr Thr Phe Gly Gln Gly Thr Lys Leu Glu Ile
            100                 105                 110

Lys

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Val Leu Tyr Arg Ser Asn Asn Arg Asn Phe
 1               5                  10

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Ala Ser
 1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Tyr Tyr Thr Thr Pro Tyr Thr
 1               5

<210> SEQ ID NO 9
<211> LENGTH: 692
<212> TYPE: PRT
<213> ORGANISM: Homo sapiens

<400> SEQUENCE: 9

Met Gly Thr Val Ser Ser Arg Arg Ser Trp Trp Pro Leu Pro Leu Pro
 1               5                  10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Asp Ala Pro Glu His Gly Ala Thr Ala Thr Phe
 50                  55                  60

His Arg Cys Ala Lys Asp Pro Trp Arg Leu Pro Gly Thr Tyr Val Val
 65                  70                  75                  80
```

```
Val Leu Lys Glu Glu Thr His Arg Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His His Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Ala Arg Tyr Arg Ala Asp Glu Tyr Gln Pro Pro Lys Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Ser Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Gly Leu Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Phe Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Arg Ser Gly
    370                 375                 380

Thr Ser Gln Ala Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Arg Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Gln Asp
465                 470                 475                 480

Glu Glu Leu Leu Ser Cys Ser Ser Phe Ser Arg Ser Gly Lys Arg Arg
                485                 490                 495
```

-continued

```
Gly Glu Arg Ile Glu Ala Gln Gly Gly Lys Arg Val Cys Arg Ala His
            500                 505                 510

Asn Ala Phe Gly Gly Glu Gly Val Tyr Ala Ile Ala Arg Cys Cys Leu
            515                 520                 525

Leu Pro Gln Val Asn Cys Ser Val His Thr Ala Pro Pro Ala Gly Ala
        530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
            580                 585                 590

Glu Ala Ser Ile His Ala Ser Cys Cys His Ala Pro Gly Leu Glu Cys
            595                 600                 605

Lys Val Lys Glu His Gly Ile Pro Ala Pro Gln Glu Gln Val Ile Val
            610                 615                 620

Ala Cys Glu Asp Gly Trp Thr Leu Thr Gly Cys Ser Pro Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Lys Glu Ala Val
                660                 665                 670

Ala Ala Val Ala Ile Cys Cys Arg Ser Arg His Leu Val Gln Ala Ser
            675                 680                 685

Gln Glu Leu Gln
    690
```

STABILIZED FORMULATIONS CONTAINING ANTI-PCSK9 ANTIBODIES

CROSS-REFERENCE TO RELATED APPLICATIONS

This application is a continuation of U.S. patent application Ser. No. 16/384,298, filed Apr. 15, 2019, which is a continuation of U.S. patent application Ser. No. 15/603,732, filed May 24, 2017, now U.S. Pat. No. 10,472,425, which is a continuation of U.S. patent application Ser. No. 14/918,109, filed Oct. 20, 2015, which is a continuation of U.S. patent application Ser. No. 14/319,730 filed Jun. 30, 2014, now U.S. Pat. No. 9,193,801, which is a continuation of U.S. patent application Ser. No. 13/559,862, filed on Jul. 27, 2012, now U.S. Pat. No. 8,795,669, which claims the benefit under 35 USC § 119(e) of U.S. Provisional Patent Application No. 61/512,666, filed Jul. 28, 2011. The contents of all of the above referenced applications are herein specifically incorporated by reference in their entireties.

FIELD

The present invention relates to the field of therapeutic antibody formulations. More specifically, the present invention relates to the field of pharmaceutical formulations comprising a human antibody that specifically binds to human proprotein convertase subtilisin/kexin type 9 (PCSK9).

SEQUENCE LISTING

The instant application contains a Sequence Listing which has been submitted electronically in ASCII format and is hereby incorporated by reference in its entirety. Said ASCII copy, created on Nov. 12, 2020, is named 707789_SA9-152CON5_ST25.txt, and is 10,048 bytes in size.

BACKGROUND

Therapeutic macromolecules (e.g., antibodies) must be formulated in a manner that not only makes the molecules suitable for administration to patients, but also maintains their stability during storage and subsequent use. For example, therapeutic antibodies in liquid solution are prone to degradation, aggregation or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, and the visual quality or appeal of the formulation. Thus, when formulating a therapeutic antibody, great care must be taken to arrive at a formulation that remains stable, contains an adequate concentration of antibody, and possesses a suitable viscosity as well as other properties that enable the formulation to be conveniently administered to patients.

Antibodies to the human proprotein convertase subtilisin/kexin type 9 protein (PCSK9) are one example of a therapeutically relevant macromolecule that requires proper formulation. Anti-PCSK9 antibodies are clinically useful for the treatment or prevention of diseases such as hypercholesterolemia and other dyslipidemias, and other conditions. Exemplary anti-PCSK9 antibodies are described, inter alia, in WO 2008/057457, WO 2008/057458, WO 2008/057459, WO 2008/063382, WO 2008/125623, U.S. Pat. No. 7,572,618, WO 2010/077854, US 2010/0166768, and US 2011/0065902.

Although anti-PCSK9 antibodies are known, there remains a need in the art for novel pharmaceutical formulations comprising anti-PCSK9 antibodies that are sufficiently stable and suitable for administration to patients.

SUMMARY

The present invention satisfies the aforementioned need by providing pharmaceutical formulations comprising a human antibody that specifically binds to human proprotein convertase subtilisin/kexin type 9 protein (PCSK9).

In one aspect, a liquid pharmaceutical formulation is provided, comprising: (i) a human antibody that specifically binds to human proprotein convertase subtilisin/kexin type 9 protein (PCSK9); (ii) a buffer; (iii) an organic cosolvent; (iv) a stabilizer; and optionally (v) a viscosity reducer.

In one embodiment, the antibody is provided at a concentration from about 50±7.5 mg/mL to about 200±30 mg/mL. In another embodiment, the antibody is provided at a concentration of about 50 mg/ml±7.5 mg/mL. In another embodiment, the antibody is provided at a concentration of about 100 mg/mL±15 mg/mL. In another embodiment, the antibody is provided at a concentration of about 150 mg/mL±22.5 mg/mL. In another embodiment, the antibody is provided at a concentration of about 175 mg/mL±26.25 mg/mL. In another embodiment, the antibody is provided at a concentration of about 200 mg/mL±30 mg/mL.

In one embodiment, the antibody comprises any one or more of an amino acid sequence of SEQ ID NO:1-8. In one embodiment, the antibody comprises (a) a heavy chain variable region (HCVR) comprising heavy chain complementarity determining regions 1, 2 and 3 (HCDR1-HCDR2-HCDR3) each comprising a sequence of SEQ ID NO:2, SEQ ID NO:3 and SEQ ID NO:4, respectively; and (b) a light chain variable region (LCVR) comprising light chain complementarity determining regions 1, 2 and 3 (LCDR1-LCDR2-LCDR3) each comprising a sequence of SEQ ID NO:6, SEQ ID NO:7 and SEQ ID NO:8, respectively. In a specific embodiment, the antibody comprises an HCVR and an LCVR, each of which comprises the amino acid sequence of SEQ ID NO:1 and SEQ ID NO:5, respectively.

In one embodiment, the pH of the liquid formulation is about pH 6.0±0.5, pH 6.0±0.4, pH 6.0±0.3, pH 6.0±0.2, pH 6.0±0.1, pH 6.0±0.05, pH 6.0±0.01, or pH 6.0. In a specific embodiment, the pH of the liquid formulation is about pH 6.0±0.3. In one embodiment, the liquid pharmaceutical buffer comprises one or more buffers, which has an effective buffering range of about pH 5.5 to about pH 7.4, or a pKa of about 6.0.

In one embodiment, the buffer is histidine. In one embodiment, the histidine is at a concentration of 5 mM±0.75 mM to 50 mM±7.5 mM. In one embodiment, the histidine is at a concentration of 10 mM±1.5 mM or about 10 mM. In one embodiment, the histidine is at a concentration of 20 mM±3 mM or about 20 mM. In one embodiment, the histidine is at a concentration of 40 nM±6 mM or about 40 nM.

In one embodiment, the organic cosolvent is a nonionic polymer containing a polyoxyethylene moiety. In some embodiments, the organic cosolvent is any one or more of polysorbate 20, poloxamer 188 and polyethylene glycol 3350. In a specific embodiment, the organic cosolvent is polysorbate 20.

In one embodiment, the organic cosolvent is at a concentration of from about 0.005%±0.00075% to about 1%±0.15% "weight to volume" or "w/v", wherein, e.g., 0.1 g/ml=10% and 0.01 g/ml=1%. In one embodiment, the organic cosolvent is polysorbate 20, which is at a concentration of about 0.2%±0.03% w/v. In another embodiment, the organic cosolvent is polysorbate 20, which is at a concentration of 0.01%±0.0015% w/v or about 0.01% w/v.

In one embodiment, the stabilizer is a sugar. In one embodiment, the sugar is selected from the group consisting of sucrose, mannitol and trehalose. In a specific embodiment, the stabilizer is sucrose.

In one embodiment, the stabilizer is at a concentration of from 1%±0.15% w/v to 20%±3% w/v. In a specific embodiment, the stabilizer is sucrose at a concentration of 5%±0.75% w/v or about 5% w/v. In another specific embodiment, the stabilizer is sucrose at a concentration of 10%±1.5% w/v or about 10% w/v. In another specific embodiment, the stabilizer is sucrose at a concentration of 12%±1.8% w/v or about 12% w/v.

In one embodiment, the viscosity reducer is a salt selected from the group consisting of arginine hydrochloride, sodium thiocyanate, ammonium thiocyanate, ammonium sulfate, ammonium chloride, calcium chloride, zinc chloride and sodium acetate. In one embodiment, the viscosity reducer is L-arginine hydrochloride.

In one embodiment, the viscosity reducer is at a concentration of from 10 mM±1.5 mM to 150 mM±22.5 mM. In one embodiment, the viscosity reducer is L-arginine hydrochloride at a concentration of 50 mM±7.5 mM or about 50 mM. In one embodiment, the viscosity reducer is L-arginine hydrochloride at a concentration of 40 mM±6 mM or about 40 mM.

In one embodiment, the viscosity of the liquid or reconstituted lyophilized pharmaceutical formulation at 25° C. is less than or equal to about 15 cPoise±10%. In one embodiment, the viscosity at 25° C. is between 1.0 cPoise±10% and 18 cPoise±10%. In one embodiment, the viscosity at 25° C. is 1.6 cPoise±10%, 1.7 cPoise±10%, 3.3 cPoise±10%, 3.5 cPoise±10%, 4.8 cPoise±10%, 6.0 cPoise±10%, 7.0 cPoise±10%, 7.1 cPoise±10%, 7.2 cPoise±10%, 7.9 cPoise±10%, 8.9 cPoise±10%, 10.0 cPoise±10%, 10.6 cPoise±10%, 11.4 cPoise±10%, 11.6 cPoise±10%, 11.8 cPoise±10%, 12.4 cPoise±10%, 13.9 cPoise±10%, 14.0 cPoise±10%, 15.5 cPoise±10%, or 17.9 cPoise±10%.

In one embodiment, the osmolality of the liquid pharmaceutical formulation is between 100±15 mOsm/kg and 460±69 mOsm/kg. In one embodiment, the osmolality of the liquid pharmaceutical formulation is 103±15 mOsm/kg or about 103 mOsm/kg. In one embodiment, the osmolality of the liquid pharmaceutical formulation is 195±29 mOsm/kg or about 195 mOsm/kg. In one embodiment, the osmolality of the liquid pharmaceutical formulation is 220±33 mOsm/kg or about 220 mOsm/kg. In one embodiment, the osmolality of the liquid pharmaceutical formulation is 330±50 mOsm/kg or about 330 mOsm/kg. In one embodiment, the osmolality of the liquid pharmaceutical formulation is 435±65 mOsm/kg or about 435 mOsm/kg. In one embodiment, the osmolality of the liquid pharmaceutical formulation is 440±66 mOsm/kg or about 440 mOsm/kg. In one embodiment, the osmolality of the liquid pharmaceutical formulation is 458±69 mOsm/kg or about 458 mOsm/kg.

In one embodiment, at least 96% or at least 97% of the non-aggregated and non-degraded form of the anti-PCSK9 antibody is recovered from the liquid pharmaceutical formulation after three months of storage of the liquid pharmaceutical formulation at −80° C., as determined by size exclusion chromatography. In one embodiment, at least 56% of the non-basic and non-acidic form (i.e., main peak or main charge form) of the anti-PCSK9 antibody is recovered from the liquid pharmaceutical formulation after three months of storage of the liquid pharmaceutical formulation at −80° C., as determined by ion exchange chromatography.

In one embodiment, at least 96% or at least 97% of the non-aggregated and non-degraded form of the anti-PCSK9 antibody is recovered from the liquid pharmaceutical formulation after three months of storage of the liquid pharmaceutical formulation at −30° C., as determined by size exclusion chromatography. In one embodiment, at least 56% of the main charge form of the anti-PCSK9 antibody is recovered from the liquid pharmaceutical formulation after three months of storage of the liquid pharmaceutical formulation at −30° C., as determined by ion exchange chromatography.

In one embodiment, at least 96% or at least 97% of the non-aggregated and non-degraded form of the anti-PCSK9 antibody is recovered from the liquid pharmaceutical formulation after three months of storage of the liquid pharmaceutical formulation at −20° C., as determined by size exclusion chromatography. In one embodiment, at least 56% of the main charge form of the anti-PCSK9 antibody is recovered from the liquid pharmaceutical formulation after three months of storage of the liquid pharmaceutical formulation at −20° C., as determined by ion exchange chromatography.

In one embodiment, at least 96% of the non-aggregated and non-degraded form of the anti-PCSK9 antibody is recovered from the liquid pharmaceutical formulation after six months of storage of the liquid pharmaceutical formulation at 5° C., as determined by size exclusion chromatography. In one embodiment, at least 58% or 59% of the main charge form of the anti-PCSK9 antibody is recovered from the liquid pharmaceutical formulation after three months of storage of the liquid pharmaceutical formulation at 5° C., as determined by ion exchange chromatography.

In one embodiment, at least 94% of the non-aggregated and non-degraded form of the anti-PCSK9 antibody is recovered from the liquid pharmaceutical formulation after six months of storage of the liquid pharmaceutical formulation at 25° C., as determined by size exclusion chromatography. In one embodiment, at least 45% or 47% of the non-basic and non-acidic form of the anti-PCSK9 antibody is recovered from the liquid pharmaceutical formulation after six months of storage of the liquid pharmaceutical formulation at 25° C., as determined by ion exchange chromatography.

In one embodiment, at least 91% or 92% of the non-aggregated and non-degraded form of the anti-PCSK9 antibody is recovered from the liquid pharmaceutical formulation after 28 days of storage of the liquid pharmaceutical formulation at 45° C., as determined by size exclusion chromatography. In one embodiment, at least 35% or 37% of the non-basic and non-acidic form of the anti-PCSK9 antibody is recovered from the liquid pharmaceutical formulation after 28 days of storage of the liquid pharmaceutical formulation at 45° C., as determined by ion exchange chromatography.

In one aspect, a liquid pharmaceutical formulation is provided, comprising: (i) from 50±7.5 mg/ml to 175±26 mg/ml of a human antibody that specifically binds to human PCSK9; (ii) from 0 mM to 40±6 mM histidine; (iii) from 0% to 0.2%±0.03% (w/v) polysorbate 20; (iv) from 0% to 12%±1.8% (w/v) sucrose; and (v) from 0 mM to 50±7.5 mM arginine, at a pH of from about 5.3 to about 6.7. The anti-PCSK9 antibody of this aspect comprises a heavy chain variable region (HCVR) and a light chain variable region (LCVR) such that the HCVR/LCVR combination comprises heavy and light chain complementarity determining regions (HCDR1-HCDR2-HCDR3/LCDR1-LCDR2-LCDR3), which comprise the amino acid sequences of SEQ ID NOs:2-3-4/SEQ ID NOs:6-7-8, respectively. In a particular embodiment, the anti-PCSK9 antibody comprises a heavy chain variable region (HCVR) and light chain variable region (LCVR) comprising an amino acid sequence of SEQ ID NO:1 and SEQ ID NO:5, respectively (hereinafter "mAb-316P").

In one embodiment of this aspect, the liquid formulation comprises (i) 50±7.5 mg/mL of mAb-316P; (ii) 10±1.5 mM histidine; (iii) 0.1%±0.015% (w/v) polysorbate 20; and (iv) 6%±0.9% (w/v) sucrose, at a pH of 6.0±0.3. In one embodiment of this particular formulation, the viscosity is about 1.7 cPoise. In one embodiment of this particular formulation, the osmolality is 220±44 mOsm/kg.

In another embodiment, the liquid formulation comprises (i) 100±20 mg/mL of mAb-316P; (ii) 20±4 mM histidine; (iii) 0.2%±0.04% (w/v) polysorbate 20; and (iv) 12%±2.4% (w/v) sucrose, at a pH of 6.0±0.3. In one embodiment of this particular formulation, the viscosity is about 3.5 cPoise. In one embodiment of this particular formulation, the osmolality is 440±88 mOsm/kg.

In another embodiment, the liquid formulation comprises (i) 150±22.5 mg/mL of mAb-316P; (ii) 10±1.5 mM histidine; (iii) 0.2%±0.03% or 0.01%±0.0015% (w/v) polysorbate 20; and (iv) 10%±1.5% (w/v) sucrose, at a pH of 6.0±0.3. In one embodiment of this particular formulation, the viscosity is about 6 cPoise. In one embodiment of this particular formulation, the osmolality is 435±65.25 mOsm/kg. In one embodiment of this particular formulation, after storage of the formulation at 45° for 28 days, ≥92% of the antibody is native and ≥35% of the antibody is of the main charge form. In one embodiment of this particular formulation, after storage of the formulation at 25° for six months, ≥94% of the antibody is native and ≥45% of the antibody is of the main charge form. In one embodiment of this particular formulation, after storage of the formulation at 5° for six months, ≥96% of the antibody is native and ≥58% of the antibody is of the main charge form. In one embodiment of this particular formulation, after storage of the formulation at −20° for twelve months, ≥97% of the antibody is native and 56% of the antibody is of the main charge form. In one embodiment of this particular formulation, after storage of the formulation at −30° for twelve months, ≥97% of the antibody is native and ≥56% of the antibody is of the main charge form. In one embodiment of this particular formulation, after storage of the formulation at −80° for twelve months, ≥97% of the antibody is native and ≥56% of the antibody is of the main charge form.

In some embodiments of this particular formulation, ≥85% of the antibody retains its biological potency after 28 days at 45° C., ≥82% after 28 days at 37° C., and/or ≥98% after 28 days at 25° C. In some embodiments of this particular formulation, ≥85% of the antibody retains its biological potency after six months at −20° C., ≥70% after six months at −30° C., and/or ≥79% after six months at −80° C. In some embodiments of this particular formulation, ≥81% of the antibody retains its biological potency after eight freeze-thaw cycles, and/or ≥84% of the antibody retains its biological activity after 120 minutes of agitation.

In another embodiment of this aspect, the liquid formulation comprises (i) 175±26.25 mg/mL of mAb-316P; (ii) 10±1.5 mM histidine; (iii) 0.01%±0.0015% (w/v) polysorbate 20; (iv) 5%±0.75% (w/v) sucrose; and (v) 50±7.5 mM arginine, at a pH of 6.0±0.3. In one embodiment of this particular formulation, the viscosity is about 10.6 cPoise. In one embodiment of this particular formulation, the osmolality is 330±50 mOsm/kg. In one embodiment of this particular formulation, after storage of the formulation at 45° for 28 days, ≥91% of the antibody is native and ≥38% of the antibody is of the main charge form. In one embodiment of this particular formulation, after storage of the formulation at 25° for six months, ≥94% of the antibody is native and ≥47% of the antibody is of the main charge form. In one embodiment of this particular formulation, after storage of the formulation at 5° for six months, ≥96% of the antibody is native and ≥59% of the antibody is of the main charge form. In one embodiment of this particular formulation, after storage of the formulation at −20° for three months, ≥96% of the antibody is native and ≥56% of the antibody is of the main charge form. In one embodiment of this particular formulation, after storage of the formulation at −30° for three months, ≥96% of the antibody is native and ≥56% of the antibody is of the main charge form. In one embodiment of this particular formulation, after storage of the formulation at −80° for three months, ≥96% of the antibody is native and ≥56% of the antibody is of the main charge form.

In one aspect, a liquid pharmaceutical formulation of any of the preceding aspects is provided in a container. In one embodiment, the container is a polycarbonate vial. In another embodiment, the container is a glass vial. In one embodiment, the glass vial is a type 1 borosilicate glass vial with a fluorocarbon-coated butyl rubber stopper. In another embodiment, the container is a microinfuser. In another embodiment, the container is a syringe. In a specific embodiment, the syringe comprises a fluorocarbon-coated plunger. In one specific embodiment, the syringe is a 1 mL long glass syringe containing less than about 500 parts per billion of tungsten equipped with a 27-G needle, a fluorocarbon-coated butyl rubber stopper, and a latex-free, non-cytotoxic rubber tip cap. In a more specific embodiment, the syringe is a Nuova Ompi 1 mL long glass syringe equipped with a 27-G thin wall needle, a FluroTec®-coated 4023/50 rubber stopper, and a FM 27 rubber tip cap. In another specific embodiment, the syringe is a 1 mL or 3 mL plastic syringe fitted with a 27-G needle. In a more specific embodiment, the plastic syringe is distributed by Becton Dickinson.

In one aspect, a pharmaceutical formulation comprising (a) 175 mg/mL±26.25 mg/mL of an anti-PCSK9 antibody, (b) 10 mM±1.5 mM histidine, pH 6±0.3, (c) 0.01% w/v±0.0015% polysorbate 20, (d) 5% w/v±0.75% sucrose, and (e) 50 mM±7.5 mM arginine, is provided, wherein (a) the antibody comprises an HCVD of SEQ ID NO:1 and an LCVD of SEQ ID NO:5, (b) over 90% of the antibodies in the formulation have a molecular weight of 155 kDa±1 kDa, (c) over 50% of the antibodies in the formulation have an isoelectric point of about 8.5, and (d) from 75% to 90% of the antibodies in the formulation are fucosylated.

In one embodiment, the pharmaceutical formulation consists of (a) 175 mg/mL±26.25 mg/mL of the anti-PCSK9 antibody of the immediately preceding paragraph, (b) 10 mM±1.5 mM histidine, pH 6±0.3, (c) 0.01% w/v±0.0015% polysorbate 20, (d) 5% w/v±0.75% sucrose, and (e) 50 mM±7.5 mM arginine, in water.

In one aspect, a pharmaceutical formulation comprising (a) 150 mg/mL±22.5 mg/mL of an anti-PCSK9 antibody, (b) 10 mM±1.5 mM histidine, pH 6±0.3, (c) 0.2% w/v±0.03% polysorbate 20, and (d) 10% w/v±1.5% sucrose is provided, wherein (i) the antibody comprises an HCVD of SEQ ID NO:1 and an LCVD of SEQ ID NO:5, (ii) over 90% of the antibodies in the formulation have a molecular weight of 155 kDa±1 kDa, (iii) over 50% of the antibodies in the formulation have an isoelectric point of about 8.5, and (iv) from 75% to 90% of the antibodies in the formulation are fucosylated.

In one embodiment, the pharmaceutical formulation consists of (a) 150 mg/mL±22.5 mg/mL of the anti-PCSK9 antibody of the immediately preceding paragraph, (b) 10 mM±1.5 mM histidine, pH 6±0.3, (c) 0.2% w/v±0.03% polysorbate 20, and (d) 10% w/v±1.5% sucrose, in water.

In one aspect, a pharmaceutical formulation comprising (a) 150 mg/mL±22.5 mg/mL of an anti-PCSK9 antibody, (b) 10 mM±1.5 mM histidine, pH 6±0.3, (c) 0.01% w/v±0.0015% polysorbate 20, and (d) 10% w/v±1.5% sucrose is provided, wherein (i) the antibody comprises an HCVD of SEQ ID NO:1 and an LCVD of SEQ ID NO:5, (ii) over 90% of the antibodies have a molecular weight of 155 kDa±1 kDa, (iii) over 50% of the antibodies in the formulation have an isoelectric point of about 8.5, and (iv) from 75% to 90% of the antibodies in the formulation are fucosylated.

In one embodiment, the pharmaceutical formulation consists of (a) 150 mg/mL±22.5 mg/mL of the anti-PCSK9 antibody of the immediately preceding paragraph, (b) 10 mM±1.5 mM histidine, pH 6±0.3, (c) 0.01% w/v±0.0015% polysorbate 20, and (d) 10% w/v±1.5% sucrose, in water.

In one aspect, a pharmaceutical formulation comprising (a) 100 mg/mL±15 mg/mL of an anti-PCSK9 antibody, (b) 20 mM±3 mM histidine, pH 6±0.3, (c) 0.2% w/v±0.03% polysorbate 20, and (d) 12% w/v±1.8% sucrose is provided, wherein (i) the antibody comprises an HCVD of SEQ ID NO:1 and an LCVD of SEQ ID NO:5, (ii) over 90% of the antibodies in the formulation have a molecular weight of 155 kDa±1 kDa, (iii) over 50% of the antibodies in the formulation have an isoelectric point of about 8.5, and (iv) from 75% to 90% of the antibodies in the formulation are fucosylated.

In one embodiment, the pharmaceutical formulation consists of (a) 100 mg/mL±15 mg/mL of the anti-PCSK9 antibody of the immediately preceding paragraph, (b) 20 mM±3 mM histidine, pH 6±0.3, (c) 0.2% w/v±0.03% polysorbate 20, and (d) 12% w/v±1.8% sucrose, in water.

In one aspect, a pharmaceutical formulation comprising (a) 50 mg/mL±7.5 mg/mL of an antibody, (b) 10 mM±1.5 mM histidine, pH 6±0.3, (c) 0.1% w/v±0.015% polysorbate 20, and (d) 6% w/v±0.9% sucrose is provided, wherein (i) the antibody comprises an HCVD of SEQ ID NO:1 and an LCVD of SEQ ID NO:5, (ii) over 90% of the antibodies in the formulation have a molecular weight of 155 kDa±1 kDa, (iii) over 50% of the antibodies in the formulation have an isoelectric point of about 8.5, and (iv) from 75% to 90% of the antibodies in the formulation are fucosylated.

In one embodiment, the pharmaceutical formulation consists of (a) 50 mg/mL±7.5 mg/mL of the anti-PCSK9 antibody of the immediately preceding paragraph, (b) 10 mM±1.5 mM histidine, pH 6±0.3, (c) 0.1% w/v±0.015% polysorbate 20, and (d) 6% w/v±0.9% sucrose, in water.

In one aspect, a method is provided for preparing a freeze-dried composition that comprises an anti-PCSK9 antibody and less than 0.3% water. The method comprises the steps of (a) combining in a glass vial water, an anti-PCSK9 antibody, histidine, sucrose, and polysorbate 20, (b) then holding the combination at about 5° C. for about 60 minutes, (c) then decreasing the temperature at a rate of about 0.5° C. per minute, (d) then holding the combination at about −45° C. for about 120 minutes, (e) then reducing the atmospheric pressure to about 100 mTorr, (f) then increasing the temperature at a rate of about 0.5° C. per minute, (g) then holding the combination at about −25° C. for about 78 hours, (h) then increasing the temperature at a rate of 0.2° C. per minute, (i) then holding the combination at about 35° C. for about 6 hours, (j) then decreasing the temperature at a rate of about 0.5° C., (k) and then holding the combination at about 25° for about 60 minutes, prior to storage.

In one embodiment, the method further comprises the steps of (l) backfilling the glass vial containing the combination of step (k) with nitrogen gas, and (m) stoppering the vial under about 80% of atmospheric pressure. In one embodiment, the composition is brought to 2-8° C. after step (i), (j) or (k) and prior to the step of stoppering the vial.

In some embodiments, at step (a) the anti-PCSK9 antibody is at 50 mg/mL±7.5 mg/mL, the histidine is at 10 mM±1.5 mM (pH 6.0), the polysorbate 20 is at 0.1%±0.015%, and the sucrose is at 6%±0.9%. In one embodiment, the anti-PCSK9 antibody comprises an HCDR1 of SEQ ID NO:2, an HCDR2 of SEQ ID NO:3, an HCDR3 of SEQ ID NO:4, an LCDR1 of SEQ ID NO: 6, an LCDR2 of SEQ ID NO:7, and an LCDR3 of SEQ ID NO:8.mAb-316P. In one embodiment, the anti-PCSK9 antibody comprises an HCVD of SEQ ID NO:1 and an LCVD of SEQ ID NO:5. In one embodiment, (i) the antibody comprises an HCVD of SEQ ID NO:1 and an LCVD of SEQ ID NO:5, (ii) over 90% of the antibodies in the combination have a molecular weight of 155 kDa±1 kDa, (iii) over 50% of the antibodies in the combination have an isoelectric point of about 8.5, and (iv) from 75% to 90% of the antibodies in the combination are fucosylated.

In one aspect, a freeze-dried pharmaceutical composition comprising an anti-PCSK9 antibody and less than 0.3% water, which is produced according to the method of the preceding aspect, is provided.

In one aspect, a pharmaceutical composition is provided, which comprises the freeze-dried pharmaceutical composition of the preceding aspect resuspended in water. In one embodiment, the pharmaceutical composition consists of 50 mg/mL±7.5 mg/mL of the anti-PCSK9 antibody, 10 mM±1.5 mM histidine (pH 6.0), 0.1%±0.015% polysorbate 20, and 6%±0.9% sucrose, in water. In one embodiment, the pharmaceutical composition consists of 100 mg/mL±15 mg/mL of the anti-PCSK9 antibody, 20 mM±3 mM histidine (pH 6.0), 0.2%±0.03% polysorbate 20, and 12%±1.8% sucrose, in water. In another embodiment, the pharmaceutical composition consists of 150 mg/mL±22.5 mg/mL of the anti-PCSK9 antibody, 30 mM±4.5 mM histidine (pH 6.0), 0.3%±0.045% polysorbate 20, and 18%±2.7% sucrose, in water. In yet another embodiment, the pharmaceutical composition consists of 175 mg/mL±26.25 mg/mL of the anti-PCSK9 antibody, 35 mM±5.25 mM histidine (pH 6.0), 0.35%±0.0525% polysorbate 20, and 21%±3.15% sucrose, in water.

In some embodiments, the anti-PCSK9 antibody comprises an HCVD of SEQ ID NO:1 and an LCVD of SEQ ID NO:5, and (b) over 90% of the antibodies in the composition have a molecular weight of 155 kDa±1 kDa, (c) over 50% of the antibodies in the composition have an isoelectric point of about 8.5, and (d) from 75% to 90% of the antibodies in the composition are fucosylated.

In one aspect, a pharmaceutical composition of any one of the preceding aspects is provided, wherein said composition is contained in a container. In one embodiment, the container is a vial, which in some embodiments is a glass vial. In another embodiment, the container is a syringe. In some embodiments, the syringe is a low-tungsten glass syringe. In one embodiment, the syringe is a Nuova Ompi 1 mL long glass syringe equipped with a 27-G thin wall needle, a FluroTec®-coated 4023/50 rubber stopper, and a FM 27 rubber tip cap.

In one aspect, a kit comprising a pharmaceutical composition of any one of the preceding aspects, a container, and instructions is provided. In one embodiment, the container is a prefilled syringe. In a particular embodiment, the syringe is a Nuova Ompi 1 mL long glass syringe equipped with a 27-G thin wall needle, a FluroTec®-coated 4023/50 rubber stopper, and a FM 27 rubber tip cap. Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All publications mentioned herein are incorporated herein by reference to describe in their entirety.

Pharmaceutical Formulations

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human proprotein convertase subtilisin/kexin type 9 (PCSK9) protein. More specifically, the present invention includes pharmaceutical formulations that comprise: (i) a human antibody that specifically binds to human PCSK9 (ii) a histidine buffer; (iii) an organic cosolvent that is a non-ionic surfactant; (iv) thermal stabilizer that is a carbohydrate; and, optionally, (v) a viscosity reducer that is a salt. Specific exemplary components and formulations included within the present invention are described in detail below.

Antibodies that Bind Specifically to PCSK9

The pharmaceutical formulations of the present invention may comprise a human antibody, or an antigen-binding fragment thereof, that binds specifically to human PCSK9. As used herein, the term "PCSK9" means a human proprotein convertase belonging to the proteinase K subfamily of the secretory subtilase family. Evidence suggests that PCSK9 increases plasma LDL levels by binding to the low-density lipoprotein particle receptor and promoting its degradation. An exemplary human PCSK9 amino acid sequence is described in SEQ ID NO:9. Antibodies to human PCSK9 are described in patent application publications US 2010/0166768, US 2011/0065902, and WO 2010/077854.

The term "antibody", as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementary determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody", as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to human PCSK9 or an epitope thereof.

An "isolated antibody", as used herein, is intended to refer to an antibody that is substantially free of other antibodies having different antigenic specificities (e.g., an isolated antibody that specifically binds human PCSK9 is substantially free of antibodies that specifically bind antigens other than human PCSK9).

The term "specifically binds", or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds human PCSK9 may, however, have cross-reactivity to other antigens, such as PCSK9 molecules from other species (orthologs). In the context of the present invention, multispecific (e.g., bispecific) antibodies that bind to human PCSK9 as well as one or more additional antigens are deemed to "specifically bind" human PCSK9. Moreover, an isolated antibody may be substantially free of other cellular material or chemicals.

Exemplary anti-human PCSK9 antibodies that may be included in the pharmaceutical formulations of the present invention are set forth in patent application publications US 2010/0166768, US 2011/0065902, and WO 2010/077854, the disclosures of which are incorporated by reference in their entirety.

According to certain embodiments of the present invention, the anti-human PCSK9 mAb-316P antibody is a human IgG1 comprising a heavy chain variable region that is of the IGHV3-23 subtype and a light chain variable region that is of the IGKV4-1 subtype (see Barbie and Lefranc, The Human Immunoglobulin Kappa Variable (IGKV) Genes and Joining (IGKJ) Segments, Exp. Clin. Immunogenet. 1998; 15:171-183; and Scaviner, D. et al., Protein Displays of the Human Immunoglobulin Heavy, Kappa and Lambda Variable and Joining Regions, Exp. Clin. Immunogenet., 1999; 16:234-240).

In some embodiments, the anti-human PCSK9 mAb-316P comprises at least one amino acid substitution, which results in a charge change at an exposed surface of the antibody relative to the germline IGKV4-1 sequence. The germline IGKV4-1 sequence, and the amino acid position assignment numbers presented herein comport with the international Immunogenetics (IMGT) information system, as described in Lefranc, M.-P., et al., IMGT®, the international ImMunoGeneTics information System®, Nucl. Acids Res, 37, D1006-D1012 (2009). In some embodiments, the exposed surface comprises a complementarity determining region (CDR). In some embodiments, the amino acid substitution or substitutions are selected from the group consisting of a basic amino acid substituted for an uncharged polar amino acid within CDR1 (e.g., at position 32) of IGKV4-1. Unique permutations in the charge distribution of an antibody, especially at an environmental interface (such as, e.g., in a CDR) would be expected to create unpredictable conditions for maintaining or advancing the stability of the antibody in solution.

In some embodiments, the anti-human PCSK9 mAb-316P antibody comprises at least one amino acid substitution, which creates a charge change within a framework region of a variable region of the antibody relative to the germline IGHV3-23 sequence or the germ line IGKV4-1 sequence. In some embodiments, the amino acid substitution or substitutions are selected from the group consisting of (a) a hydrophobic amino acid substituted for a polar amino acid in framework region 3 (FR3) (e.g., at position 77) of IGHV3-23, and (b) a polar amino acid substituted for a basic amino acid in framework region 2 (FR2) (e.g., at position 51) of IGKV4-1. Changes in the ability of the peptide chain to fold, especially within a framework region, which affects the CDR interface with the solvent, would be expected to create unpredictable conditions for maintaining or advancing the stability of the antibody in solution.

According to certain embodiments of the present invention, the anti-human PCSK9 antibody, or antigen-binding fragment thereof, comprises a heavy chain complementary determining region (HCDR) 1 of SEQ ID NO: 2, an HCDR2 of SEQ ID NO:3, and an HCDR3 of SEQ ID NO: 4. In certain embodiments, the anti-human PCSK9 antibody, or antigen-binding fragment thereof, comprises an HCVD of SEQ ID NO:1.

According to certain embodiments of the present invention, the anti-human PCSK9, or antigen-binding fragment thereof, comprises a light (kappa) chain complementary determining region (LCDR) 1 of SEQ ID NO: 6, an LCDR2 of SEQ ID NO: 7, and an LCDR3 of SEQ ID NO: 8. In certain embodiments, the anti-human PCSK9 antibody, or antigen-binding fragment thereof, comprises an LCVD of SEQ ID NO:5.

The non-limiting, exemplary antibody used in the Examples herein is referred to as "mAb-316P". This antibody is also referred to in U.S. Pat. No. 7,608,693 as H4H098P. mAb-316P (H4H098P) comprises an HCVR/LCVR amino acid sequence pair having SEQ ID NOs:1/5, and HCDR1-HCDR2-HCDR3/LCDR1-LCDR2-LCDR3 domains represented by SEQ ID NOs:2-3-4/SEQ ID NOs: 6-7-8.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 50±7.5 mg/mL to 250±37.5 mg/mL of antibody; 60±9 mg/mL to 240±36 mg/mL of antibody; 70±10.5 mg/mL to 230±34.5 mg/mL of antibody; 80±12 mg/mL to 220±33 mg/mL of antibody; 90±13.5 mg/mL to 210±31.5 mg/mL of antibody; 100±15 mg/mL to 200±30 mg/mL of antibody; 110±16.5 mg/mL to 190±28.5 mg/mL of antibody; 120±18 mg/mL to 180±27 mg/mL of antibody; 130±19.5 mg/mL to 170±25.5 mg/mL of antibody; 140±21 mg/mL to 160±24 mg/mL of antibody; 150±22.5 mg/mL of antibody; or 175±26.25 mg/ml. For example, the formulations of the present invention may comprise about 50 mg/mL; about 60 mg/mL; about 65 mg/mL; about 70 mg/mL; about 75 mg/mL; about 80 mg/mL; about 85 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; about 200 mg/mL; about 205 mg/mL; about 210 mg/mL; about 215 mg/mL; about 220 mg/mL; about 225 mg/mL; about 230 mg/mL; about 235 mg/mL; about 240 mg/mL; about 245 mg/mL; or about 250 mg/mL of an antibody or an antigen-binding fragment thereof, that binds specifically to human PCSK9.

Excipients and pH

The pharmaceutical formulations of the present invention comprise one or more excipients. The term "excipient", as used herein, means any non-therapeutic agent added to the formulation to provide a desired consistency, viscosity or stabilizing effect.

In certain embodiments, the pharmaceutical formulation of the invention comprises at least one organic cosolvent in a type and in an amount that stabilizes the human PCSK9 antibody under conditions of rough handling or agitation, such as, e.g., vortexing. In some embodiments, what is meant by "stabilizes" is the prevention of the formation of more than 3% aggregated antibody of the total amount of antibody (on a molar basis) over the course of rough handling. In some embodiments, rough handling is vortexing a solution containing the antibody and the organic cosolvent for about 60 minutes or about 120 minutes.

In certain embodiments, the organic cosolvent is a non-ionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN® 20 (polysorbate 20), sorbitan monolaurate and polyoxyethylenesorbitan monolaurate. Poloxamer 188 is also known as Pluronic® F-68.

The amount of non-ionic surfactant contained within the pharmaceutical formulations of the present invention may vary depending on the specific properties desired of the formulations, as well as the particular circumstances and purposes for which the formulations are intended to be used. In certain embodiments, the formulations may contain 0.01%±0.0015% to 0.2%±0.03% surfactant. For example, the formulations of the present invention may comprise about 0.0085%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; or about 0.23% polysorbate 20 or poloxamer 188.

The pharmaceutical formulations of the present invention may also comprise one or more stabilizers in a type and in an amount that stabilizes the human PCSK9 antibody under conditions of thermal stress. In some embodiments, what is meant by "stabilizes" is maintaining greater than about 91% of the antibody in a native conformation when the solution containing the antibody and the thermal stabilizer is kept at about 45° C. for up to about 28 days. In some embodiments, what is meant by "stabilizes" is wherein less than about 6% of the antibody is aggregated when the solution containing the antibody and the thermal stabilizer is kept at about 45° C. for up to about 28 days. As used herein, "native" means the major form of the antibody by size exclusion, which is generally an intact monomer of the antibody.

In certain embodiments, the thermal stabilizer is a sugar or sugar alcohol selected from sucrose, trehalose and mannitol, or any combination thereof, the amount of which contained within the formulation can vary depending on the specific circumstances and intended purposes for which the formulation is used. In certain embodiments, the formulations may contain about 3% to about 14% sugar or sugar alcohol; about 4% to about 13% sugar or sugar alcohol; about 5% to about 12% sugar or sugar alcohol; about 6% to about 11% sugar or sugar alcohol; about 7% to about 10% sugar or sugar alcohol; about 8% to about 9% sugar or sugar alcohol; about 4% to about 6% sugar or sugar alcohol; about 5% to about 7% sugar or sugar alcohol; about 9% to about 11% sugar or sugar alcohol; or about 11% to about 13% sugar or sugar alcohol. For example, the pharmaceutical formulations of the present invention may comprise 4%±0.6%; 5%±0.75%; 6%±0.9%; 7%±1.05%; 8%±1.2%; 9%±1.35%; 10%±1.5%; 11%±1.65%; 12%±1.8%; 13%±1.95%; or about 14%±2.1% sugar or sugar alcohol (e.g., sucrose, trehalose or mannitol).

The pharmaceutical formulations of the present invention may also comprise a buffer or buffer system, which serves to maintain a stable pH and to help stabilize the human PCSK9 antibody. In some embodiments, what is meant by "stabilizes" is wherein less than 4.5%±0.5% or less than 6.0%±0.5% of the antibody is aggregated when the solution containing the antibody and the buffer is kept at about 45° C. for up to about 28 days. In some embodiments, what is meant by "stabilizes" is wherein less than 3%±0.5% or less than 2.6%±0.5% of the antibody is aggregated when the solution containing the antibody and the buffer is kept at about 37° C. for up to about 28 days. In some embodiments, what is meant by "stabilizes" is wherein at least 91%±0.5% or at least 92%±0.5% of the antibody is in its native conformation as determined by size exclusion chromatography when the solution containing the antibody and the buffer is kept at about 45° C. for up to about 28 days. In some embodiments, what is meant by "stabilizes" is wherein at least 94%±0.5% or at least 95%±0.5% of the antibody is in its native conformation as determined by size exclusion chromatography when the solution containing the antibody and the buffer is kept at about 37° C. for up to about 28 days. By "native" or "native conformation", what is meant is the antibody fraction that is not aggregated or degraded. This is generally determined by an assay that measures the relative size of the antibody entity, such as a size exclusion chromatographic assay. The non-aggregated and non-degraded antibody elutes at a fraction that equates to the native antibody, and is generally the main elution fraction. Aggregated antibody elutes at a fraction that indicates a size greater than the native antibody. Degraded antibody elutes at a fraction that indicates a size less than the native antibody.

In some embodiments, what is meant by "stabilizes" is wherein at least 38%±0.5% or at least 29%±0.5% of the antibody is in its main charge form as determined by cation exchange chromatography when the solution containing the antibody and the buffer is kept at about 45° C. for up to about 28 days. In some embodiments, what is meant by "stabilizes" is wherein at least 46%±0.5% or at least 39%±0.5% of the antibody is in its main charge form as determined by cation exchange chromatography when the solution containing the antibody and the buffer is kept at about 37° C. for up to about 28 days. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present invention may have a pH of from about 5.2 to about 6.4. For example, the formulations of the present invention may have a pH of about 5.5; about 5.6; about 5.7; about 5.8; about 5.9; about 6.0; about 6.1; about 6.2; about 6.3; about 6.4; or about 6.5. In some embodiments, the pH is 6.0±0.4; 6.0±0.3; 6.0±0.2; 6.0±0.1; about 6.0; or 6.0.

In some embodiments, the buffer or buffer system comprises at least one buffer that has a buffering range that overlaps fully or in part the range of pH 5.5-7.4. In one embodiment, the buffer has a pKa of about 6.0±0.5. In certain embodiments, the buffer comprises a histidine buffer. In certain embodiments, the histidine is present at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In certain embodiments, the buffer system comprises histidine at 10 mM±1.5 mM, at a pH of 6.0±0.3.

The pharmaceutical formulations of the present invention may also comprise one or more excipients that serve to maintain a reduced viscosity or to lower the viscosity of formulations containing a high concentration of anti-PCSK9 antibody drug substance (e.g., generally >150 mg/ml of antibody). In some embodiments, the formulation comprises arginine in an amount sufficient to maintain the viscosity of the liquid formulation at less than 20±3 cPoise, less than 15±2.25 cPoise, or less than 11±1.65 cPoise. In some embodiments, the formulation comprises arginine in an amount sufficient to maintain the viscosity at or below 10.6±1.59 cPoise. In certain embodiments, the pharmaceutical formulation of the present invention contains arginine, preferably as L-arginine hydrochloride, at a concentration of 10 mM±1.5 mM to 90 mM±13.5 mM, 20 mM±3 mM to 80 mM±12 mM, 30 mM 4.5 mM to 70 mM±10.5, 40 mM 6 mM to 60±9 mM or 50 mM±7.5 mM.

Exemplary Formulations

According to one aspect of the present invention, the pharmaceutical formulation is a low viscosity, generally physiologically isotonic liquid formulation, which comprises: (i) a human antibody that specifically binds to human PCSK9 (e.g., mAb-316P), at a concentration of 50 mg/mL±7.5 mg/mL, 100 mg/ml±15 mg/mL, 150 mg/mL±22.5 mg/mL, or 175 mg/mL±26.25 mg/mL; (ii) a buffer system that provides sufficient buffering at about pH 6.0±0.3; (iii) a sugar which serves inter alia as a thermal stabilizer; (iv) an organic cosolvent, which protects the structural integrity if the antibody; and (v) a salt of an amino acid, which serves to keep the viscosity manageable for injection in a convenient volume for subcutaneous administration.

According to one embodiment, the pharmaceutical formulation comprises: (i) a human IgG1 antibody that specifically binds to human PCSK9 and which comprises a substituted IGHV3-23 type heavy chain variable region and a substituted IGLV4-1 type light chain variable region (e.g., mAb-316P) at a concentration from 50±7.5 mg/mL to about 175±26.25 mg/mL; (ii) a buffer system comprising histidine, which buffers effectively at about pH 6.0±0.3; (iii) sucrose; (iv) a non-ionic detergent, such as a polysorbate; and optionally (v) an arginine salt.

According to one embodiment, the pharmaceutical formulation comprises: (i) a human IgG1 antibody that specifically binds to human PCSK9, and which comprises an HCDR1 of SEQ ID NO:2, an HCDR2 of SEQ ID NO:3, an HCDR3 of SEQ ID NO:4, an LCDR1 of SEQ ID NO:6, an LCDR2 of SEQ ID NO:7, and an LCDR3 of SEQ ID NO:8, at a concentration of about 150 mg/ml±22.5 mg/mL; (ii) histidine at 10 mM±1.5 mM, which buffers at pH 6.0±0.3; (iii) sucrose at 10% w/v±1.5% w/v; and (iv) polysorbate 20 at 0.2% w/v±0.03% w/v or 0.01% w/v±0.0015% w/v.

According to one embodiment, the pharmaceutical formulation comprises: (i) a human IgG1 antibody that specifically binds to human PCSK9, and which comprises an HCDR1 of SEQ ID NO:2, an HCDR2 of SEQ ID NO:3, an HCDR3 of SEQ ID NO:4, an LCDR1 of SEQ ID NO:6, an LCDR2 of SEQ ID NO:7, and an LCDR3 of SEQ ID NO:8, at a concentration of about 100 mg/mL±15 mg/mL; (ii) histidine at about 20 mM±3 mM, which buffers at pH 6.0±0.3; (iii) sucrose at 12% w/v±1.8% w/v; and (iv) polysorbate 20 at 0.2% w/v±0.03% w/v or 0.01% w/v±0.0015% w/v.

According to one embodiment, the pharmaceutical formulation comprises: (i) a human IgG1 antibody that specifically binds to human PCSK9, and which comprises an HCDR1 of SEQ ID NO:2, an HCDR2 of SEQ ID NO:3, an HCDR3 of SEQ ID NO:4, an LCDR1 of SEQ ID NO:6, an LCDR2 of SEQ ID NO:7, and an LCDR3 of SEQ ID NO:8, at a concentration of about 50 mg/mL±7.5 mg/mL; (ii) histidine at 10 mM±1.5 mM, which buffers at pH 6.0±0.3; (iii) sucrose at 6% w/v±0.9% w/v; and (iv) polysorbate 20 at 0.1% w/v±0.015% w/v or 0.01% w/v±0.0015% w/v.

According to one embodiment, the pharmaceutical formulation comprises: (i) a human IgG1 antibody that specifically binds to human PCSK9, and which comprises a heavy chain variable domain of SEQ ID NO:1, and a light chain variable domain of SEQ ID NO:5, at a concentration of 175 mg/ml±26.25 mg/mL; (ii) histidine at 10 mM±1.5 mM, which buffers at pH 6.0±0.3; (iii) sucrose at 5% w/v±0.75% w/v; (iv) polysorbate 20 at 0.01% w/v±0.0015% w/v; and (v) L-arginine hydrochloride at 50 mM±7.5 mM.

According to one embodiment, the pharmaceutical formulation comprises: (i) a human IgG1 antibody that specifically binds to human PCSK9, and which comprises a heavy chain variable domain of SEQ ID NO:1, and a light chain variable domain of SEQ ID NO:5, at a concentration of about 150 mg/ml±22.5 mg/mL; (ii) histidine at 10 mM±1.5 mM, which buffers at pH 6.0±0.3; (iii) sucrose at 10% w/v±1.5% w/v; and (iv) polysorbate 20 at 0.2% w/v±0.03% w/v or 0.01% w/v±0.0015% w/v.

According to one embodiment, the pharmaceutical formulation comprises: (i) a human IgG1 antibody that specifically binds to human PCSK9, and which comprises a heavy chain variable domain of SEQ ID NO:1, and a light chain variable domain of SEQ ID NO:5, at a concentration of about 100 mg/mL±15 mg/mL; (ii) histidine at about 20 mM±3 mM, which buffers at pH 6.0±0.3; (iii) sucrose at 12% w/v±1.8% w/v; and (iv) polysorbate 20 at 0.2% w/v±0.03% w/v or 0.01% w/v±0.0015% w/v.

According to one embodiment, the pharmaceutical formulation comprises: (i) a human IgG1 antibody that specifically binds to human PCSK9, and which comprises a heavy chain variable domain of SEQ ID NO:1, and a light chain variable domain of SEQ ID NO:5, at a concentration of about 50 mg/mL±7.5 mg/mL; (ii) histidine at 10 mM±1.5 mM, which buffers at pH 6.0±0.3; (iii) sucrose at 6% w/v±0.9% w/v; and (iv) polysorbate 20 at 0.1% w/v±0.015% w/v or 0.01% w/v±0.0015% w/v.

Additional non-limiting examples of pharmaceutical formulations encompassed by the present invention are set forth elsewhere herein, including the working Examples presented below.

Stability and Viscosity of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion high performance liquid chromatography [SE-HPLC]), such that native means non-aggregated and non-degraded. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., about 35° C., about 37° C., or about 45° C. For example, a pharmaceutical formulation may be deemed stable if after 6 months of storage at 5° C., greater than about 95%, 96%, 97% or 98% of native antibody is detected by SE-HPLC. A pharmaceutical formulation may also be deemed stable if after 6 months of storage at 25° C., greater than about 94%, 95%, 96%, 97% or 98% of native antibody is detected by SE-HPLC. A pharmaceutical formulation may also be deemed stable if after 28 days of storage at 45° C., greater than about 91%, 92%, 93%, 94%, 95%, 96%, 97% or 98% of native antibody is detected by SE-HPLC. A pharmaceutical formulation may also be deemed stable if after three months of storage at −20° C., greater than about 96%, 97%, or 98% of native antibody is detected by SE-HPLC. A pharmaceutical formulation may also be deemed stable if after three months of storage at −30° C., greater than about 96%, 97% or 98% of native antibody is detected by SE-HPLC. A pharmaceutical formulation may also be deemed stable if after three months of storage at −80° C., greater than about 96%, 97% or 98% of native antibody is detected by SE-HPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion high performance liquid chromatography [SE-HPLC]). An "acceptable degree of stability", as that phrase is used herein, means that at most 6% of the antibody is in an aggregated form detected in the formulation after storage for a defined amount of time at a given temperature. In certain embodiments an acceptable degree of stability means that at most about 6%, 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., about 35° C., about 37° C. or about 45° C. For example, a pharmaceutical formulation may be deemed stable if after six months of storage at 5° C., less than about 3%, 2%, 1%, 0.5%, or 0.1% of the antibody is detected in an aggregated form. A pharmaceutical formulation may also be deemed stable if after six months of storage at 25° C., less than about 4%, 3%, 2%, 1%, 0.5%, or 0.1% of the antibody is detected in an aggregated form. A pharmaceutical formulation may also be deemed stable if after 28 days of storage at 45° C., less than about 6%, 5%, 4%, 3%, 2%, 1%, 0.5%, or 0.1% of the antibody is detected in an aggregated form. A pharmaceutical formulation may also be deemed stable if after three months of storage at −20° C., −30° C., or −80° C. less than about 3%, 2%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, PNAS, Apr. 16, 2002, 99(8):5283-5288). The percentage of "acidified" antibody can be determined by, inter alia, ion exchange chromatography (e.g., cation exchange high performance liquid chromatography [CEX-HPLC]). An "acceptable degree of stability", as that phrase is used herein, means that at most 49% of the antibody is in a more acidic form detected in the formulation after storage for a defined amount of time at a defined temperature. In certain embodiments an acceptable degree of stability means that at most about 49%, 45%, 40%, 35%, 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°–8° C., about 5° C., about 25° C., or about 45° C. For example, a pharmaceutical formulation may be deemed stable if after three months of storage at −80° C., −30° C., or −20° C. less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 5° C., less than about 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 25° C., less than about 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Measuring the biological activity or binding affinity of the antibody to its target may also be used to assess stability. For example, a formulation of the present invention may be regarded as stable if, after storage at e.g., 5° C., 25° C., 45° C., etc. for a defined amount of time (e.g., 1 to 12 months), the anti-PCSK9 antibody contained within the formulation binds to PCSK9 with an affinity that is at least 90%, 95%, or more of the binding affinity of the antibody prior to said storage. Binding affinity may be determined by e.g., ELISA or plasmon resonance. Biological activity may be determined by a PCSK9 activity assay, such as e.g., contacting a cell that expresses PCSK9 with the formulation comprising the anti PCSK9 antibody. The binding of the antibody to such a cell may be measured directly, such as e.g., via FACS analysis. Alternatively, the downstream activity of the PCSK9 system may be measured in the presence of the antibody, and compared to the activity of the PCSK9 system in the absence of antibody. In some embodiments, the PCSK9 may be endogenous to the cell. In other embodiments, the PCSK9 may be ectopically expressed in the cell.

Additional methods for assessing the stability of an antibody in formulation are demonstrated in the Examples presented below.

The liquid pharmaceutical formulations of the present invention may, in certain embodiments, exhibit low to moderate levels of viscosity. "Viscosity" as used herein may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present invention, will exhibit an absolute viscosity of less than about 15 cPoise (cP). For example, a fluid formulation of the invention will be deemed to have "low viscosity", if, when measured using standard viscosity measurement techniques, the formulation exhibits an absolute viscosity of about 15 cP, about 14 cP, about 13 cP, about 12 cP, about 11 cP, about 10 cP, about 9 cP, about 8 cP, or less. As used herein, a moderate level of viscosity, in reference to a fluid formulation of the present invention, will exhibit an absolute viscosity of between about 35 cP and about 15 cP. For example, a fluid formulation of the invention will be deemed to have "moderate viscosity", if when measured using standard viscosity measurement techniques, the formulation exhibits an absolute viscosity of about 34 cP, about 33 cP, about 32 cP, about 31 cP, about 30 cP, about 29 cP, about 28 cP, about 27 cP, about 26 cP, about 25 cP, about 24 cP, about 23 cP, about 22 cP, about 21 cP, about 20 cP, about 19 cP, 18 cP, about 17 cP, about 16 cP, or about 15.1 cP.

As illustrated in the examples below, the present inventors have made the surprising discovery that low to moderate viscosity liquid formulations comprising high concentrations of an anti-human PCSK9 antibody (e.g., from about 100 mg/ml up to at least 200 mg/mL) can be obtained by formulating the antibody with arginine from about 25 mM to about 100 mM. In addition, it was further discovered that the viscosity of the formulation could be decreased to an even greater extent by adjusting the sucrose content to less than about 10%.

Containers and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod, which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®", available from West Pharmaceutical Services, Inc. (Lionville, Pa.). FluroTec® is an example of a fluorocarbon coating used to minimize or prevent drug product from adhering to the rubber surfaces.

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to Autopen® (Owen Mumford, Inc., Woodstock, UK), Disetronic Pen (Disetronic Medical Systems, Bergdorf, Switzerland), Humalog® Mix75/25™ pen, Humalog® pen, Humulin® 70/30 pen (Eli Lilly and Co., Indianapolis, Ind.), NovoPen® I, II and III (Novo Nordisk, Copenhagen, Denmark), NovoPen® Junior (Novo Nordisk, Copenhagen, Denmark), BD™ pen (Becton Dickinson, Franklin Lakes, N.J.), OptiPen®, OptiPen Pro®, OptiPen Starlet™, and OptiClik® (Sanofi-Aventis, Frankfurt, Germany). Examples of disposable pen or autoinjector delivery devices having applications in subcutaneous delivery of a pharmaceutical composition of the present invention include, but are not limited to the SoloSTAR® pen (Sanofi-Aventis), the FlexPen® (Novo Nordisk), and the KwikPen™ (Eli Lilly), the SureClick™ Autoinjector (Amgen, Thousand Oaks, Calif.), the Penlet® (Haselmeier, Stuttgart, Germany), the EpiPen® (Dey, L. P.), and the Humira® Pen (Abbott Labs, Abbott Park, Ill.).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In one embodiment, the liquid pharmaceutical formulation containing about 150 mg/mL±22.5 mg/mL anti-PCSK9 antibody is administered subcutaneously in a volume of approximately 1 mL±0.15 ml in a prefilled syringe. In one embodiment, the syringe is a 1 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM 27 rubber needle shield, and a FluroTec® coated 4023/50 rubber plunger.

In one embodiment, the liquid pharmaceutical formulation containing about 150 mg/mL±22.5 mg/mL anti-PCSK9 antibody is administered subcutaneously in a volume of approximately 1 mL±0.15 ml in a prefilled syringe. In one embodiment, the syringe is a 1 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FluroTec® coated 4023/50 rubber plunger.

Therapeutic Uses of the Pharmaceutical Formulations

The pharmaceutical formulations of the present invention are useful, inter alia, for the treatment, prevention or amelioration of any disease or disorder associated with PCSK9 activity, including diseases or disorders mediated by PCSK9. Exemplary, non-limiting diseases and disorders that can be treated or prevented by the administration of the pharmaceutical formulations of the present invention include various dyslipidemias such as, e.g., hypercholesterolemia, familial hypercholesterolemia, hyperlipidemia, familial hyperlipidemia, dysbetalipoproteinemia, familial dysbetalipoproteinemia, hypertriglyceridemia, and familial hypertriglyceridemia.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, temperature is in degrees Centigrade, and pressure is at or near atmospheric pressure.

Initial formulation development activities involved screening organic cosolvents, thermal stabilizers, and buffers in liquid and lyophilized formulations of mAb-316P (anti-PCSK9 antibodies of the invention) to identify excipients that are compatible with the protein and enhance its stability, while maintaining near physiologic osmolality and low viscosity for intravenous and subcutaneous injection. Buffer conditions were also examined to determine the optimal pH for maximum protein stability.

Example 1: Development of Anti-PCSK1 MAB-316P Formulation

Various buffers, organic cosolvents, and thermal stabilizers were screened to identify excipients that enhance the stability of the PCSK9 antibody. Buffer conditions were also examined to determine the optimal pH for maximum antibody stability. Results generated from these studies were used to develop a stable liquid formulation, as well as a stable lyophilized formulation suitable for clinical use, for either intravenous (IV) or subcutaneous administration (SC). For the lyophilized drug product, a single, dual use formulation was developed which can be reconstituted with sterile water for injection (WFI) to a concentration of either 50 mg/mL for IV or 100 mg/mL for SC administration. Once reconstituted to 50 mg/mL, the drug product can be further diluted into an IV bag containing 0.9% sodium chloride for IV delivery. For the liquid formulation, mAb-316P was formulated at 175±27 mg/ml and 150±23 mg/ml. In one embodiment, the 175±27 mg/mL mAb-316P is formulated in 10±1.5 mM histidine (pH 6.0±0.3), 0.01%±0.0015% polysorbate 20, 5%±0.75% sucrose. In one embodiment, the 150±23 mg/mL mAb-316P is formulated in 10±1.5 mM histidine (pH 6.0±0.3), 0.2%±0.03% or 0.01%±0.0015% polysorbate 20, 10%±1.5% sucrose.

Example 2: Anti-PCSK1 MAB-316P Buffer and pH

The effect of pH and buffer type on the stability of the PCSK9 antibodies was examined in liquid formulations. 2 mg/mL anti-PCSK9 mAb-316P was incubated at 45° C. in 10 mM each of either acetate (pH 5.0-5.5), citrate (pH 5.5-6.0), succinate (pH 6.0), histidine (pH 6.0), phosphate (pH 6.0-7.5), or Tris (pH 8.0) buffer to assess the effect of buffer and pH on the thermal stability of the protein (Table 1). For this experiment, the liquid formulations were each kept as 0.35 mL in a 2 mL capacity Type 1 borosilicate glass vial with a FluroTec® coated 4432/50 butyl rubber stopper. The total amount of mAb-316P recovered was determined using reverse-phase chromatography. The percentage of the native versus aggregated form of mAb-316P was determined using size-exclusion chromatography. The percentage of acidic and basic species of the mAb-316P was determined using cation exchange chromatography. Maximum protein stability was observed, as determined by both size exclusion chromatography (SE) and cationic exchange chromatography (CEX), when anti-PCSK9 mAb-316P was formulated in 10 mM histidine buffer at pH 6.0.

The optimal pH for mAb-316P was then determined by incubating 10 mg/mL of mAb-316P at 45° C. in histidine buffer between pH 5.5 and pH 6.5. Maximum protein stability was observed, as determined by SE and CEX, when mAb-316P was formulated in histidine buffered at pH 6.0 (Table 2). These analyses also revealed that the main protein degradation pathways were the formation of aggregates, cleavage products, and charge variants. Based on these results, 10 mM histidine buffer at pH 6.0 was chosen for development of a liquid and lyophilized mAb-316P formulation.

Results from formulation development studies indicate that under basic conditions (pH≥6.5), anti-PCSK9 mAb-316P in solution may undergo deamidation reactions. Conversely, at pH≤5.5, an increased rate of formation of molecular weight variants of mAb-316P was observed. Based on these data, the buffer pH used for the formulation of the mAb-316P is maintained between pH 5.7 and pH 6.3. The accelerated stability of mAb-316P is similar over this pH range.

Example 3: Selection of Protectants Against Agitation Stress

Various cosolvents were individually tested for their ability to minimize the formation of particulates in mixtures containing mAb-316P due to agitation stress. Turbidity analysis of agitated drug substance demonstrated an increase in the optical density (OD) at 405 nm when a solution containing mAb-316P (0.35 mL of 25 mg/mL mAb-316P, 10 mM histidine, pH 6.0±0.2 in a 2 mL capacity Type 1 borosilicate glass vial with a FluroTec® coated 4432/50 butyl rubber stopper) was vortexed for 10 minutes (Table 3). Formulation with any of the evaluated cosolvents appears to have prevented the agitation-induced increase in turbidity. However, 20% PEG 300, 10% PEG 300, and 20% propylene glycol significantly decreased the thermal stability of mAb-316P as determined by SE (Table 4; same mAb-316P concentration, buffer, and container conditions as in the vortex study above). Formulations with polysorbate 20, polysorbate 80, Pluronic® F-68, and PEG 3350 had no significant effect on the thermal stability of mAb-316P as determined by SE and CEX, making these cosolvents suitable for formulating anti-PCSK9 mAb-316P. Polysorbate 20 was chosen as the organic cosolvent for development of both a lyophilized and liquid formulation of mAb-316P because it demonstrated good stability attributes in both the agitation and thermal studies of mAb-316P.

Example 4: Selection of Protectants Against Thermal Stress

Various excipients, which were selected from a varied list containing sugars, amino acids, and inorganic salts, were individually tested to optimally increase the thermal stability of mAb-316P. A summary of some the thermal stabilizers that were examined is presented in Table 5. For these experiments, the "thermal stabilizer" excipients were included in a solution of 20 mg/mL mAb-316P in 10 mM histidine (0.35 mL in 2 mL capacity Type 1 borosilicate glass vial with a FluroTec® coated 4432/50 butyl rubber stopper). Formulations containing sucrose, sorbitol, mannitol, and trehalose had the least amount of mAb-316P degradation as determined by SE analysis. However, those formulations containing sorbitol showed a surprising increase in turbidity compared to those formulations containing sucrose, trehalose, and mannitol (Table 5). While sucrose, trehalose, and mannitol were observed to have no effect on the formation of charge variants of the anti-PCSK9 mAb-316P, mannitol was observed to destabilize the protein during multiple freeze-thaw cycles. Thus, mAb-316P has similar stability when formulated with sucrose or trehalose.

Example 5: Lyophilized Formulation

A lyophilized formulation was developed to increase the stability of anti-PCSK9 mAb-316P, particularly with respect to charge variants, and to increase the maximum deliverable concentration of mAb-316P. Various lyoprotectants were combined with 0.7 mL of 50 mg/mL mAb-316P, 10 mM histidine, in a 2 mL capacity Type 1 borosilicate glass vial with a FluroTec® coated 4432/50 butyl rubber stopper, lyophilized, and examined for their ability to stabilize lyophilized mAb-316P when incubated at 50° C. Prior to analysis, the lyophilized cake was reconstituted to 100 mg/mL mAb-316P. The two lyophilized formulations with the greatest stability as determined by SE and CEX contained: 1) 6% sucrose or 2) 2% sucrose plus 2% arginine. 6% sucrose was chosen for the mAb-316P drug product formulation. Thus, the anti-PCSK9 mAb-316P lyophilized drug product was produced by lyophilization in an optimized, aqueous buffered formulation containing 10 mM histidine, pH 6.0±0.1, 0.1% (w/v) polysorbate 20, 6% (w/v) sucrose, and 50 mg/mL anti-PCSK9 mAb-316P. The storage and stress stability of this lyophilized formulation is presented in Table 7.

The anti-pPCSK9 mAb-316P lyophilization cycle was developed based on the measured Tg' (frozen glass transition temperature) of the formulation, which was measured using subambient modulated differential scanning calorimetry (mDSC). The product temperature must not go above the Tg' during primary drying, which was determined to be −27.9° C.

Lyophilized mAb-316P was produced by filling 5.3 mL of the 50 mg/mL mAb-316P, 10 mM histidine (pH 6.0), 0.1% polysorbate 20, 6% sucrose formulation into 20 mL Type 1 glass vials and lyophilizing according to the following steps:

| | | |
|---|---|---|
| 1. | Shelf temperature required during loading: | 5-25° C. |
| 2. | Initial Hold at: | 5° C. for 60 minutes |
| 3. | Ramp rate (time) for freezing: | 0.5° C./min (100 minutes) |
| 4. | Hold at: | −45° C. for 120 minutes |
| 5. | Vacuum Set Point: | 100 mTorr |
| 6. | Ramp rate (time) for heating to primary drying: | 0.5° C./min (40 minutes) |
| 7. | Shelf Temperature of Primary Drying: | −25° C. |
| 8. | Length of Primary Drying: | 78 hours |
| 9. | Ramp rate (time) for heating to secondary drying: | 0.2° C./min (300 minutes) |

| | |
|---|---|
| 10. Shelf temperature of Secondary Drying: | 35° C. |
| 11. Length of Secondary Drying: | 6 hours |
| 12. Ramp rate (time) for cooling: | 0.5° C./min (20 minutes) |
| 13. Hold at: | 25° C. for 60 minutes* |
| 14. Backfill with nitrogen gas | |
| 15. Stoppering under vacuum: | 80% of Atmospheric pressure (608,000 mTorr) |

When extensive storage is needed after secondary drying and prior to the stoppering step, the shelf temperature of the lyophilizer is brought to 2-8° C. Lyophilized drug product that was produced using the final cycles described above had good cake appearance, low moisture content (0.3%), reconstitution time less than 4 minutes, and no turbidity of the reconstituted solution.

The appearance of the lyophilized cake was unaffected when the mAb-316P drug product (mAb-316P DP) was incubated for 2 months at 50° C. or stored for 3 months at 5° C. There was no affect on pH, appearance, or turbidity of the reconstituted mAb-316P drug product, and no significant difference in the amount of mAb-316P recovered. After 2 months of incubation at 50° C., the lyophilized mAb-316P drug product was 1.1% more degraded as determined by SE-HPLC and 8.3% more degraded as determined by CEX-HPLC. No significant degradation was observed when the lyophilized mAb-316P drug product was stored for 3 months at 5° C. No significant loss of potency, as determined using an anti-PCSK9 bioassay, was observed for any of the stressed samples.

Example 6: Liquid and Reconstituted MAB-316P

There are two methods to reconstitute lyophilized mAb-316P drug product depending on the route of administration. For IV administration, mAb-316P drug product is reconstituted with 5.0 mL of sterile WFI resulting in 5.3 mL of solution containing 50 mg/mL mAb-316P, 10 mM histidine, pH 6.0, 0.1% (w/v) polysorbate 20, and 6% (w/v) sucrose. For SC administration, mAb-316P drug product is reconstituted with 2.3 mL of sterile WFI resulting in 2.7 mL solution containing 100 mg/mL REGN727, 20 mM histidine, pH 6.0, 0.2% (w/v) polysorbate 20, and 12% (w/v) sucrose. The volume available for withdrawal is 4.8 mL for IV and 2.0 mL for SC injection; an overage of 0.7 mL of reconstituted solution is contained in the SC vial.

In the alternative, liquid mAb-316P is formulated as a liquid formulation, without the intervening step of lyophilization. The liquid mAb-316P formulations are at either 150 mg/mL (±15%) or 175 mg/mL (±15%) anti-PCSK9 mAb-316P, in 10±1.5 mM histidine (pH 6.0±0.3), polysorbate 20 at 0.01%±0.0015% or 0.2%±0.03%, sucrose at 5%±0.75% or 10%±1.5%, and, in the case of the 175 mg/mL formulation, arginine at 50±7.5 mM.

Anti-PCSK9 mAb-316P was found to be stable when sterile filtered. A Millipore Millipak® filtration unit was used in the manufacture of the clinical supplies, while a filter of identical composition was used in research studies (Millipore Millex® Durapore®). Compared to storage in glass vials, the stability of mAb-316P formulated drug substance (mAb-316P FDS) was not significantly affected when stored in either a polypropylene tube, a polystyrene tube, a polycarbonate tube, or in a glass vial containing a stainless steel ball bearing (Table 8).

Example 7: Liquid Formulation in Prefilled Syringes

Formulation development studies were conducted with the goal of developing a high concentration, liquid formulation of mAb-316P that could be used in pre-filled syringes (PFS) for SC delivery. Results from the development phase of the lyophilized REGN727 formulation demonstrated that the optimal buffer, pH, organic cosolvent, and thermal stabilizer were histidine, pH 6.0, polysorbate 20, and sucrose, respectively (supra). These same excipients were used to develop both the 150 mg/mL and 175 mg/mL mAb-316P drug product formulations. Arginine was added to the 175 mg/mL version of the mAb-316P drug product to reduce the viscosity of the formulation. The stress stability of 150 and 175 mg/mL mAb-316P drug product was examined in 1 mL long, glass Nuova Ompi Pre-filled Syringes (PFS) and compared to the stability of 150 and 175 mg/mL drug product in control, glass vials. No significant difference in the amount of physical or chemical degradation was observed after incubation of 150 or 175 mg/mL mAb-316P drug product at 45° C. between the OMPI PFS and the glass control vial. These data indicate that the 150 and 175 mg/mL anti-PCSK9 mAb-316P drug product formulations are sufficiently stable for use in PFS.

Example 8: Stability of MAB-316P Formulated Drug Substance

Stability studies were performed to determine both the storage and stress stability of 150 and 175 mg/mL mAb-316P formulations. Turbidity and RP-HPLC assays were used to assess the physical stability of mAb-316P. Physical stability is defined as the recovery of soluble forms of the anti-PCSK9 mAb-316P in solution. Loss of protein could be due to either protein precipitation or surface adsorption. The presence of particulates in solution can be detected by visual inspection or by optical density (OD) measurements at 405 nm (turbidity measurements). In this latter assay, an increase in OD indicates an increase in turbidity due to the formation of particulates. The presence of particulates as determined by OD measurements indicates that the sample has failed to maintain stability. Recovery of mAb-316P is measured by RP-HPLC. In the RP-HPLC assay, the ant-PCSK9 mAb-316P antibody is eluted from the reverse phase column as a single peak. The concentration of each test sample is determined from the area of the eluted mAb-316P antibody peak compared to a calibration curve generated using mAb-316P standards of defined protein loads.

Chemical stability refers to the integrity of the chemical structure of the anti-PCSK9 antibody (mAb-316P) in a sample. Most chemical instability can be attributed to the formation of covalently modified forms of the protein, (e.g. covalent aggregates, cleavage products, or charge variants) and non-covalently modified forms of the protein (e.g. non-covalent aggregates). Thus far, the only degradation products of mAb-316P that have been detected are species that differ in either molecular weight or charge. The higher and lower molecular weight degradation products can be separated from native mAb-316P by SE-HPLC. The percentage of native mAb-316P in the size exclusion chromatographic method is determined by the ratio of the area of the native peak to the total area of all mAb-316P antibody peaks.

Charge variant forms of mAb-316P are resolved from native mAb-316P using cation exchange chromatography. Peaks that elute from the CEX-HPLC column with retention times earlier than that of the main peak are labeled "Acidic Peaks", while those that elute from the CEX-H PLC column with retention times later than that of the main peak are labeled "Basic Peaks". The percentage of degraded mAb-316P in the cation exchange chromatographic method is determined by the change in the relative percentage of the main, acidic, and basic peak areas compared to the total area of all mAb-316P peaks.

Evaluation of mAb-316P under accelerated conditions was performed by subjecting the antibody to a variety of stress tests. These tests represent the extreme handling conditions that the formulated drug substance may be subjected to during the manufacture of drug product. mAb-316P formulated drug substance was filled in 5 mL polycarbonate vials for the agitation, cycles of freeze/thaw, and frozen storage conditions. mAb-316P formulated drug substance was filled in glass vials to examine stress stability at high temperatures.

Example 9: Storage Stability Studies of Formulated Drug Substance (FDS)

150 mg/mL mAb-316P formulated drug substance (FDS; 0.5 mL in 5 mL polycarbonate vial; 150 mg/mL mAb-316P antibody, 10 mM histidine (pH 6.0), 0.2% polysorbate 20, and 10% sucrose) was found to be physically and chemically stable when stored at ≤−20° C. for 12 months. No significant loss of mAb-316P was observed and no significant chemical degradation was detected by size exclusion or ion exchange chromatography. Greater than 97% of the recovered mAb-316P was of the "native" structure as determined by size exclusion, and greater than 56% of the recovered mAb-316P was of the "main charge variant" as determined by cation exchange. The results are summarized in Table 9.

175 mg/mL mAb-316P formulated drug substance (FDS; 0.75 mL in 5 mL polycarbonate vial; 175 mg/mL mAb-316P antibody, 10 mM histidine (pHs 6.0), 0.01% polysorbate 20, 5% sucrose, and 50 mM arginine) was found to be physically and chemically stable when stored at ≤−20° C. for 3 months. No significant loss of mAb-316P was observed and no significant chemical degradation was detected by size exclusion or ion exchange chromatography. Greater than 96% of the recovered mAb-316P was of the "native" structure as determined by size exclusion, and greater than 56% of the recovered mAb-316P was of the "main charge variant" as determined by cation exchange. The results are summarized in Table 10.

Example 10: Stress Stability Studies of Formulated Drug Substance

Stress stability studies were performed on the 150 mg/mL mAb-316P formulated drug substance (FDS) (0.35 mL-0.5 mL of 150 mg/mL mAb-316P, 10 mM histidine (pH 6.0), 0.2% polysorbate 20, 10% sucrose) and the 175 mg/mL mAb-316P formulated drug substance (0.5 mL-1.7 mL of 175 mg/mL mAb-316P, 10 mM histidine (pH 6.0), 0.01% polysorbate 20, 5% sucrose, 50 mM arginine). High temperature studies were conducted in a 2 mL capacity Type 1 borosilicate glass, FluroTec® coated 4432/50 butyl rubber stopper; the remaining studies were performed in a 5 mL polycarbonate vial. The 150 mg/mL and the 175 mg/mL anti-PCSK9 mAb-316P formulated drug substance were found to be physically and chemically stable when agitated (vortexed) for two hours. The solution remained visibly clear, no loss of protein occurred, and no molecular weight species or charge variants were formed (Tables 11 & 12). MAb-316P was also observed to be both physically and chemically stable when subjected to eight cycles of freezing to −80° C. and thawing to room temperature. Following the eight freeze/thaw cycles, the protein solution remained visibly clear and no loss of protein was observed. No molecular weight (either soluble aggregates or cleavage products) or charge variant forms were detected by either SE or CEX assays, respectively.

Although the 150 and the 175 mg/mL anti-PCSK9 mAb-316P formulated drug substance were physically stable when incubated at 37° C. or 45° C. for 28 days, some chemical degradation was nonetheless observed (Tables 11 & 12). These stress tests indicated that the main degradation pathways were the formation of aggregates, cleavage products, and charge variants. As expected, the rate of degradation of anti-PCSK9 mAb-316P antibody was slower at 37° C. than at 45° C. There was no significant change in the physical or chemical stability of 150 or 175 mg/mL mAb-316P formulated drug substance when incubated at 25° C. for 28 days.

Example 11: Storage Stability of Drug Product (DP)

The 150 mg/mL mAb-316P drug product consists of 10 mM histidine, pH 6.0, 0.01% polysorbate 20, 10% sucrose, and 150 mg/mL anti-PCSK9 mAb-316P antibody. The 175 mg/mL mAb-316P drug product consists of 10 mM histidine, pH 6.0, 0.01% polysorbate 20, 5% sucrose, 50 mM arginine, and 175 mg/mL anti-PCSK9 mAb-316P antibody. There was no change in the physical and chemical stability of either the 150 mg/mL or the 175 mg/mL mAb-316P drug product (DP) when stored at 5° C. for 6 months in the pre-filled syringe (PFS; OMPI 1 mL long lass syringe with a 27 gauge thin wall needle and FM 27 rubber needle shield closed with a FluroTec® coated 4023/50 rubber plunger) (Table 13 and Table 14). The solutions remained visibly clear, no loss of protein was observed, and no change in pH occurred after these stresses. In addition, there was no significant change in molecular weight species or charge variants were detected by SE and CEX, respectively.

Example 12: Stress Stability of Drug Product (DP)

The stress stabilities of 150 mg/mL mAb-316P drug product and 175 mg/ml mAb-316P drug product were examined by incubating the pre-filled syringes at 25° C. and 45° C. Each respective drug product was physically stable when incubated at 45° C. for 28 days or incubated at 25° C. for 6 months (Tables 13 & 14). The solution remained visibly clear, no loss of protein was observed, and no change in pH occurred after these stresses. However, aggregates and charge variants were detected when the protein was incubated at 45° C. and 25° C. This stress test indicates these are the main degradation pathways for drug product. Of the 150 mg/mL drug product, the mAb-316P aggregate increased 1.9% and acidic species increased 19.1% after incubation at 45° C. for 28 days. A reduced level of chemical degradation was detected when the protein was incubated at 25° C. There was a 0.8% increase in the relative amount of aggregate and a 10.3% increase in acidic species after 6 months of incubation at 25° C. Of the 175 mg/mL drug product, the mAb-316P aggregate increased 1.8% and acidic species increased 17.0% after incubation at 45° C. for 28 days. A reduced level of chemical degradation was detected when the protein was incubated at 25° C. There was 0.7% increase in aggregate and a 9.4% increase in acidic species after 6 months of incubation at 25° C. For both the 150 and 175 mg/mL drug products, there was no significant change in the stability of mAb-316P after 1 month of incubation at 25° C.

Example 13: Fill Volumes

The injectable volume from a pre-filled syringe (PFS) containing 150 mg/mL REGN727 drug product is 1.0 mL. The injectable volume from a PFS containing 175 mg/mL REGN727 drug product is 1.14 mL. No overage is included in either PFS because the dead volume in the syringe is negligible (0.005 to 0.01 mL).

Example 14: Stability of Mab-316P in Storage Materials

Anti-PCSK9 mAb-316P was found to be stable when sterile filtered. A Millipore Millipak® filtration unit was used for research studies and in the manufacture of the clinical supplies. Compared to storage in glass vials, the stability of 150 and 175 mg/mL mAb-316P formulated drug substance was not significantly affected when stored in a polypropylene tube, a polystyrene tube, a polycarbonate tube, or in a glass vial containing a stainless steel gasket (Table 15 and Table 16). Although degradation was observed when the formulated drug substance was incubated at 40° C. for 14 days, no significant difference in the amount of mAb-316P degradation was observed between the control, glass vial and exposure to the plastic containers and stainless steel.

Example 15: Characterization of Ant-PCSK9 Antibody Mab-316P

At least two lots of mAb-316P (Lot 1 and Lot 2) were analyzed by size exclusion chromatography and multi-angle laser light scattering (SEC-MALLS), an analytical method that gives an estimate of the molar mass of a protein or glycoprotein. Lots 1 and 2 had respective molar masses of 154.5 and 154.6 kDa. Other lots had molar masses ranging from 154.4 to 154.8 kDa (average of about 155 kDa) for the main species peak eluted from the SE matrix. This main peak represented about 96.7-99.2% of the total protein peak area and corresponds to intact mAb-316P monomer (i.e., "native" as used herein).

mAb-316P was analyzed by capillary isoelectric focusing (cIEF) to determine the isoelectric points for the major constituent isoforms. The pI and average peak area (% total peak area) of mAb-316P samples determined by cIEF are summarized in Table 17. Each lot exhibited a main species (peak 5) with a calculated pI of approximately 8.5, which was present at 66.4% and 68.0% for lots 1 and 2, respectively. The dominant species (peak 5) most likely represents intact fully glycosylated antibody lacking the C-terminal lysine (i.e., "main charge form" as used herein).

Mass spectrometric (MS) analysis of the reduced mAb-316P tryptic maps from Lot 1 and Lot 2 resulted in the confirmation of a single glycosylation site, Asn298, within the Fc domain in both lots. The major covalently linked glycan forms this glycosylation site are summarized in Table 18. Overall, both lots were determined to possess complex bi-antennary glycans, with majority of them fucosylated at Asn298. However, the relative amount of fucosylated agalactosyl (G0) containing sugar chain species in Lot 2 was slightly higher relative to the amount of this glycoform in Lot 1. Conversely, the relative amounts of fucosylated digalactosyl (G2) and fucosylated monogalactosyl (G1) containing sugar chain forms in Lot 2 were reduced compared to the relative amounts of these sugar chain structures in Lot 1. Analysis of the LC/MS results of the two drug substance samples (peak 16) also identified 2.9% and 8.4% of heavy chain peptide lacking glycan occupancy at Asn298 on Lot 1 and Lot 2, respectively.

Glycan profiles generated by HPLC after release of oligosaccharides from each of the two mAb-316P lots were analyzed. In each chromatogram, the derivatized oligosaccharides were separated into two main groups: non-fucosylated bi-antennary species and fucosylated bi-antennary species. Within each group (fucosylated vs. non-fucosylated), the oligosaccharides were further separated into digalactosyl (G2), monogalactosyl (G1), and agalactosyl (G0) forms. Oligosaccharide structure assignments were obtained via MALDI-TOF mass spectrometry. Integration of each peak in the two chromatograms revealed that the fucosylation level of the two mAb-316P lots was generally high, with 80.0% and 86.9% fucosylation observed in Lots 1 and 2, respectively.

Although the total percent fucosylation of the two lots was similar, there were quantitative differences in the relative abundance of each of the glycan forms present in the two lots (Table 19). For Lot 1, peak area percentages of 34.4%, 39.6%, and 11.7%, were determined for the G0, G1, and G2 fucosylated glycan structures, respectively. In contrast, peak area percentages for Lot 2 were 45.8%, 33.3%, and 7.1%, for the G0, G1, and G2 fucosylated glycoform structures, respectively, indicating differences in the extent of galactosylation between the two lots. A high mannose glycan (man5 glycan) peak (peak 2) was detected at a relative abundance of 1.8-2.9% relative to the total amount of sugar chain observed in both lots (Table 19). A total of nine unidentified peaks with peak area percentages ranging from 0.5% to 1.5% were also detected in both lots examined by this method and represent≤3% of the total glycan peak areas detected in each lot. Analysis of an equimolar co-mixture of the two lots yielded no new peaks and the peak area percentages of all peaks in the co-mixture correlated well with expected values based on individual analysis of each lot (Table 19).

TABLE 1

Effect of buffer and pH on mAb-316P stability at 45° C. for 28 days

| pH/Buffer | Turbidity [1] | Total (mg/mL) | % Native | % Aggr. | % Main | % Acidic | % Basic |
|---|---|---|---|---|---|---|---|
| no incubation[2] | 0.00 | 1.8 | 98.1 | 0.3 | 57.0 | 33.0 | 10.0 |
| pH 8.0, Tris | 0.00 | 1.7 | 88.9 | 0.8 | 15.2 | 82.4 | 2.4 |
| pH 8.0, Phosphate | 0.01 | 2.0 | 89.4 | 1.3 | NA | NA | NA |
| pH 7.5, Phosphate | 0.01 | 1.9 | 91.7 | 0.9 | NA | NA | NA |
| pH 7.0, Phosphate | 0.01 | 2.1 | 92.4 | 0.7 | 16.7 | 78.8 | 4.5 |
| pH 6.5, Phosphate | 0.00 | 2.0 | 93.2 | 0.6 | 25.0 | 68.3 | 6.6 |
| pH 6.0, Phosphate | 0.00 | 1.8 | 93.9 | 0.3 | 29.8 | 62.3 | 8.0 |
| pH 6.0, Histidine | 0.00 | 1.9 | 94.5 | 0.0 | 36.9 | 54.0 | 9.1 |
| pH 6.0, Succinate | 0.00 | 1.9 | 93.1 | 0.4 | 31.9 | 59.8 | 8.3 |
| pH 6.0, Citrate | 0.00 | 1.9 | 95.1 | 0.4 | 32.1 | 58.1 | 9.9 |
| pH 5.5, Citrate | 0.00 | 2.1 | 94.6 | 0.4 | 28.0 | 62.0 | 9.9 |

TABLE 1-continued

Effect of buffer and pH on mAb-316P stability at 45° C. for 28 days

| pH/Buffer | Turbidity[1] | Total (mg/mL) | % Native | % Aggr. | % Main | % Acidic | % Basic |
|---|---|---|---|---|---|---|---|
| pH 5.5, Acetate | 0.00 | 2.0 | 92.4 | 0.2 | 34.5 | 56.9 | 8.5 |
| pH 5.0, Acetate | 0.00 | 1.8 | 93.0 | 0.2 | 31.1 | 57.5 | 11.4 |

[1] Turbidity = change in OD at 405 nm relative to starting material.
[2] Average values of the non-incubated material for all 12 formulations

TABLE 2

Effect of pH on 10 mg/mL mAb-316P, 10 mM Histidine at 45° C. for 28 Days

| pH/Buffer | Turbidity[1] | Total (mg/mL) | % Native | % Aggregate | % Main | % Acidic | % Basic |
|---|---|---|---|---|---|---|---|
| no incubation[2] | 0.00 | 9.5 | 98.1 | 0.2 | 57.8 | 31.1 | 11.1 |
| pH 5.5 | 0.01 | 9.5 | 94.3 | 0.5 | 34.7 | 52.2 | 13.1 |
| pH 6.0 | 0.01 | 9.7 | 94.7 | 0.9 | 37.5 | 51.8 | 10.6 |
| pH 6.5 | 0.01 | 10.1 | 93.4 | 1.8 | 35.7 | 55.2 | 9.1 |

[1] Turbidity = change in OD at 405 nm relative to starting material.
[2] Average values of the non-incubated material for all 3 formulations

TABLE 3

Effect of Cosolvents on 25 mg/mL mAb-316P Vortexed for 120 Minutes

| Organic Cosolvent | Turbidity[1] | Total (mg/mL) | % Native | % Agg'd | % Main | % Acidic | % Basic |
|---|---|---|---|---|---|---|---|
| No vortexing[2] | 0.00 | 25.6 | 97.3 | 0.5 | 50.6 | 39.2 | 10.3 |
| No Cosolvent | 0.10 | 25.6 | 97.3 | 0.5 | 51.1 | 39.0 | 9.9 |
| 0.2% Polysorbate 20 | 0.01 | 24.7 | 97.2 | 0.5 | 51.1 | 38.9 | 10.1 |
| 0.2% Polysorbate 80 | 0.01 | 24.7 | 97.3 | 0.5 | 50.9 | 38.9 | 10.2 |
| 0.2% Pluronic F68 | 0.01 | 25.2 | 96.9 | 0.5 | 50.5 | 39.2 | 10.3 |
| 3% PEG 3350 | 0.01 | 25.3 | 97.1 | 0.5 | 50.7 | 39.0 | 10.2 |
| 1.5% PEG 3350 | 0.01 | 24.9 | 97.1 | 0.5 | 50.8 | 39.1 | 10.1 |
| 20% PEG 300 | 0.00 | 26.7 | 97.0 | 0.6 | 48.8 | 40.5 | 10.7 |
| 10% PEG 300 | 0.01 | 25.7 | 97.2 | 0.5 | 49.9 | 39.8 | 10.3 |
| 20% Propylene Glycol | 0.01 | 25.8 | 96.9 | 0.5 | 51.1 | 38.6 | 10.3 |

[1] Turbidity = change in OD at 405 nm relstive to starting material.
[2] Average values of the non-vortexed material for all 9 formulations

TABLE 4

Effect of Cosolvents on 25 mg/mL mAb-316P Incubated at 45° C. for 28 Days

| Organic Cosolvent | Turb'ty[1] | pH | Total mg/mL | % Native | % Agg'd | % Main | % Acidic | % Basic |
|---|---|---|---|---|---|---|---|---|
| no incubation[2] | 0.00 | 6.1 | 25.6 | 97.3 | 0.5 | 50.6 | 39.2 | 10.3 |
| No Cosolvent | 0.02 | 6.2 | 24.9 | 94.5 | 0.7 | 34.8 | 54.7 | 10.5 |
| 0.2% Polysorbate 20 | 0.03 | 6.2 | 24.3 | 94.6 | 0.5 | 35.2 | 54.3 | 10.5 |
| 0.2% Polysorbate 80 | 0.02 | 6.2 | 24.3 | 94.8 | 0.6 | 35.1 | 54.5 | 10.4 |
| 0.2% Pluronic F68 | 0.03 | 6.1 | 24.6 | 94.7 | 0.6 | 33.8 | 55.6 | 10.6 |
| 3% PEG 3350 | 0.03 | 6.2 | 24.8 | 95.0 | 0.7 | 35.9 | 53.5 | 10.6 |
| 1.5% PEG 3350 | 0.02 | 6.2 | 24.4 | 94.8 | 0.6 | 36.0 | 53.5 | 10.5 |
| 20% PEG 300 | 0.12 | 4.8 | 25.4 | 88.8 | 4.2 | NA | NA | NA |
| 10% PEG 300 | 0.09 | 5.4 | 25.0 | 93.7 | 0.9 | 24.1 | 67.0 | 8.9 |
| 20% Propylene Glycol | 0.03 | 6.1 | 24.6 | 89.9 | 5.6 | 34.6 | 54.2 | 11.2 |

[1] Turbidity = change in OD at 405 nm relstive to starting material.
[2] Average values of the non-vortexed material for all 9 formulations

TABLE 5

Effect of stabilizer on 20 mg/mL mAb-316P, 10 mM histidine at 45° C. for 28 days

| Excipient | Visual | Turb'ty[1] | pH | Total mg/mL | % Native | % Agg'd | % Main | % Acidic | % Basic |
|---|---|---|---|---|---|---|---|---|---|
| no incubation[2] | Pass | 0.00 | 6.0 | 20.2 | 97.7 | 0.5 | 51.1 | 39.3 | 9.6 |
| No Stabilizer | Pass | 0.02 | 6.1 | 19.8 | 93.6 | 2.0 | 33.5 | 56.5 | 10.1 |
| 150 mM NaCl | Fail | 0.03 | 6.0 | 20.0 | 91.0 | 4.6 | 35.3 | 51.0 | 13.6 |
| 20% Sucrose | Pass | 0.04 | 6.0 | 22.6 | 94.4 | 1.0 | 32.1 | 57.0 | 10.9 |
| 20% Sorbitol | Pass | 0.16 | 5.8 | 21.8 | 94.3 | 1.0 | 23.5 | 67.4 | 9.1 |
| 10% Mannitol | Pass | 0.02 | 6.0 | 21.2 | 94.8 | 0.9 | 34.4 | 54.5 | 11.1 |
| 20% Trehalose | Pass | 0.05 | 6.0 | 22.7 | 94.7 | 0.5 | 33.2 | 56.6 | 10.2 |
| 5% Glycerol | Pass | 0.10 | 5.9 | 20.8 | 90.2 | 5.4 | NA | NA | NA |
| 3% Arginine | Pass | 0.02 | 6.1 | 21.1 | 92.9 | 3.0 | 37.5 | 49.2 | 13.3 |
| 3% Glycine | Pass | 0.03 | 6.1 | 19.8 | 93.7 | 1.7 | 31.0 | 58.0 | 10.9 |

[1] Turbidity = change in OD at 405 nm relative to starting material.
[2] Average values of the non-incubated material for all 9 formulations

TABLE 6

Effect of lyoprotectants on lyophilized mAb-316P incubated at 50° C. for 28 days

| Excipient | Visual | Turb'ty[1] | pH | Total mg/mL | % Native | % Agg'd | % Main | % Acidic | % Basic |
|---|---|---|---|---|---|---|---|---|---|
| no incubation | Pass | 0.00 | 6.0 | 100 | 97.1 | 1.2 | 51.0 | 38.3 | 10.7 |
| No Lyoprotectant | Fail | 0.09 | 6.1 | 100 | 70.0 | 28.5 | 24.2 | 35.1 | 40.7 |
| 2% Sucrose | Pass | 0.02 | 6.1 | 104 | 90.7 | 7.4 | 37.4 | 39.1 | 23.6 |
| 6% Sucrose | Pass | 0.00 | 6.1 | 105 | 96.1 | 1.8 | 46.8 | 39.2 | 14.1 |
| 2% Sucr., 2% Gly | Pass | 0.02 | 6.0 | 114 | 94.5 | 3.4 | 40.9 | 42.4 | 16.8 |
| 2% Sucr., 2% Arg | Pass | 0.00 | 5.9 | 109 | 95.9 | 2.0 | 47.2 | 38.4 | 14.4 |

[1]Turbidity = change in OD at 405 nm relstive to starting material.
[2]Lyophilized Drug Product reconstituted to 100 mg/mL REGN727 prior to analysis.
[3]Average values of the starting material of 4 formulations.

TABLE 7

Stability of lyophilized Drug Product Reconstituted to 100 mg/ml

| | Storage Temperature | | | | |
|---|---|---|---|---|---|
| | No storage | 5° C. 4 mo. | 25° C. 3 mo. | 40° C. 3 mo. | 50° C. 2 mo. |
| Turbidity[1] | 0.00 | 0.01 | 0.01 | 0.02 | 0.02 |
| pH | 6.2 | 6.3 | 6.2 | 6.2 | 6.2 |
| % Total Recvr'd | 100 | 104 | 100 | 98 | 105 |
| % Native | 96.0 | 96.5 | 96.2 | 95.7 | 94.9 |
| % Aggregate | 1.7 | 1.4 | 1.7 | 2.4 | 2.9 |
| % Main | 50.6 | 51.5 | 49.2 | 46.2 | 43.5 |
| % Acidic | 38.0 | 37.9 | 38.2 | 39.5 | 40.1 |
| % Basic | 11.4 | 10.5 | 12.7 | 14.3 | 16.2 |
| Bioassay (% Ref. Std.)[2] | 146 | NP | NP | NP | 152 |

[1]Turbidity = change in OD at 405 nm relative to starting material.
[2]Acceptance criteria: 50-200% of reference standard

TABLE 8

Compatibility of 50 mg/mL mAb-316P for 14 days at 40° C. and 75% humidity

| | No Storage | Storage | | | | |
|---|---|---|---|---|---|---|
| | | Glass | Poly-propylene | Poly-styrene | Poly-carbonate | Stainless Steel |
| Turbidity[1] | 0.00 | 0.00 | 0.01 | 0.00 | 0.01 | 0.01 |
| % Total | 100 | 98 | 99 | 104 | 103 | 98 |
| % Native | 97.0 | 96.3 | 96.3 | 96.2 | 96.2 | 96.1 |
| % Aggregate | 2.0 | 1.9 | 1.9 | 2.0 | 2.0 | 2.0 |
| % Main | 50.8 | 45.7 | 44.9 | 45.2 | 45.6 | 45.5 |
| % Acidic | 38.1 | 42.8 | 43.6 | 43.0 | 42.5 | 43.2 |
| % Basic | 11.2 | 11.5 | 11.6 | 11.9 | 11.8 | 11.2 |

[1]Turbidity = change in OD at 405 nm relative to starting material.

TABLE 9

Stability of 150 mg/mL anti-PCSK9 mAb-316P for 12 months −80° C.

| Storage Temperature | control | −80° C. | −30° C. | −20° C. |
|---|---|---|---|---|
| Turbidity (OD 405 nm) | 0.00 | 0.00 | 0.01 | 0.01 |
| % Total mAb-316P Recovered | 100 | 104 | 108 | 111 |
| % Native Recovered | 97.5 | 97.3 | 97.2 | 97.2 |
| % Aggregate Recovered | 1.7 | 1.8 | 1.8 | 1.9 |
| % Main Recovered | 56.2 | 56.5 | 56.4 | 56.3 |
| % Acidic Recovered | 26.5 | 25.7 | 25.7 | 25.4 |
| % Basic Recovered | 17.4 | 17.9 | 17.9 | 18.2 |

TABLE 10

Stability of 175 mg/mL anti-PCSK9 mAb-316P for 3 months −80° C.

| Storage Temperature | control | −80° C. | −30° C. | −20° C. |
|---|---|---|---|---|
| Turbidity (OD 405 nm)[1] | 0.00 | 0.01 | 0.01 | 0.01 |
| % Total REGN727 Recovered (RP-HPLC) | 100 | 100 | 104 | 101 |
| % Native REGN727 Recovered (SE-HPLC) | 96.2 | 96.5 | 96.4 | 96.3 |
| % REGN727 Aggregate Recovered (SE-HPLC) | 2.7 | 2.5 | 2.6 | 2.7 |
| % Main REGN727 Recovered (CEX-HPLC) | 58.5 | 56.2 | 56.6 | 56.7 |
| % Acidic REGN727 Recovered (CEX-HPLC) | 29.4 | 29.4 | 29.4 | 29.4 |
| % Basic REGN727 Recovered (CEX-HPLC) | 12.2 | 14.5 | 14.0 | 13.9 |

[1]Turbidity = change in OD at 405 nm relative to starting material.

TABLE 11

Stability of 150 mg/mL mAb-316P FDS[1] under stress conditions

| | Stress Test | | | | | | | | |
|---|---|---|---|---|---|---|---|---|---|
| | No Stress[2] | Agitation | | 45° C. Incubation | | 37° C. Incubation | | 25° C. Incubation | Freeze/Thaw |
| | Time of Stress | | | | | | | | |
| | 0 min | 60 min | 120 min | 14 days | 28 days | 14 days | 28 days | 14 days | 28 days | 8 cycles |
| Visual Appearance | Pass | Pass | Pass | Pass | Pass | Pass | Pass | Pass | Pass | Pass |

TABLE 11-continued

Stability of 150 mg/mL mAb-316P FDS[1] under stress conditions

| | Stress Test | | | | | | | | | |
|---|---|---|---|---|---|---|---|---|---|---|
| | No Stress[2] | Agitation | | 45° C. Incubation | | 37° C. Incubation | | 25° C. Incubation | | Freeze/Thaw |
| | | | | | Time of Stress | | | | | |
| | 0 min | 60 min | 120 min | 14 days | 28 days | 14 days | 28 days | 14 days | 28 days | 8 cycles |
| Turbidity[3] | 0.00 | 0.00 | 0.00 | 0.02 | 0.03 | 0.00 | 0.01 | 0.00 | 0.00 | 0.00 |
| pH | 6.0 | 6.0 | 6.0 | 6.0 | 6.0 | 6.0 | 6.0 | 6.0 | 6.0 | 6.0 |
| % Total Recovered | 100 | 101 | 102 | 98 | 98 | 99 | 98 | 100 | 99 | 101 |
| % Native Recovered | 97.4 | 97.5 | 97.2 | 94.2 | 92.4 | 95.7 | 95.1 | 96.7 | 96.2 | 97.1 |
| % Aggregate Recovered | 1.6 | 1.7 | 2.1 | 3.4 | 4.1 | 2.4 | 2.6 | 2.0 | 2.2 | 1.7 |
| % Main Recovered | 53.6 | 53.7 | 54.7 | 38.7 | 29.0 | 46.3 | 39.5 | 51.5 | 49.1 | 53.9 |
| % Acidic Recovered | 27.2 | 26.1 | 25.9 | 39.5 | 48.6 | 31.9 | 36.9 | 27.8 | 28.9 | 26.5 |
| % Basic Recovered | 19.3 | 20.2 | 19.5 | 21.8 | 22.5 | 21.8 | 23.7 | 20.7 | 22.0 | 19.6 |
| Bioassay (% Relative Potency)[4] | 84 | NP | 84 | NP | 85 | NP | 82 | NP | 98 | 81 |

[1]10 mM histidine, pH 6.0, 0.2% polysorbate 20, 10% sucrose, 150 mg/mL anti-PCSK9 mAb-316P
[2]'No stress' values are averages from both stability studies.
[3]Turbidity is reported as the relative change in OD at 405 nm as compared to the starting material
[4]Percent relative potency; Acceptance criteria: 50-200% of reference standard

TABLE 12

Stability of 175 mg/mL mAb-316P FDS[1] under stress conditions

| | Stress Test | | | | | | | | | |
|---|---|---|---|---|---|---|---|---|---|---|
| | No Stress[2] | Agitation | | 45° C. Incubation | | 37° C. Incubation | | 25° C. Incubation | | Freeze/Thaw |
| | | | | | Time of Stress | | | | | |
| | 0 min | 60 min | 120 min | 14 days | 28 days | 14 days | 28 days | 14 days | 31 days | 8 cycles |
| Visual Appearance | Pass | Pass | Pass | Pass | Pass | Pass | Pass | NA | Pass | Pass |
| Turbidity[3] | 0.00 | 0.00 | 0.01 | 0.01 | 0.03 | 0.00 | 0.01 | NA | 0.00 | 0.01 |
| pH | 6.0 | 6.0 | 6.0 | 6.1 | 6.1 | 6.0 | 6.0 | NA | 6.0 | 6.0 |
| % Total Recovered | 100 | 96 | 98 | 101 | 98 | 100 | 96 | NA | 99 | 98 |
| % Native Recovered | 96.5 | 96.3 | 96.4 | 94.5 | 91.7 | 95.7 | 94.7 | NA | 96.2 | 96.1 |
| % Aggregate Recovered | 2.5 | 2.5 | 2.5 | 3.6 | 5.2 | 2.8 | 3.0 | NA | 2.6 | 2.3 |
| % Main Recovered | 59.5 | 58.3 | 59.0 | 47.1 | 38.4 | 56.3 | 46.9 | NA | 58.2 | 59.3 |
| % Acidic Recovered | 30.1 | 29.3 | 29.4 | 39.5 | 47.6 | 32.3 | 39.8 | NA | 30.9 | 29.5 |
| % Basic Recovered | 10.3 | 12.4 | 11.6 | 13.4 | 14.1 | 11.4 | 13.4 | NA | 11.0 | 11.1 |
| Bioassay (% Relative Potency)[4] | 0.00 | 0.00 | 0.01 | 0.01 | 0.03 | 0.00 | 0.01 | NA | 0.00 | 0.01 |

[1]10 mM histidine, pH 6.0, 0.01% polysorbate 20, 5% sucrose, 50 mM arginine 175 mg/mL anti-PCSK9 mAb-316P.
[2]'No stress' values are averages from both stability studies.
[3]Turbidity = change in OD at 405 nm relative to starting material.
[4]Percent relative potency; Acceptance criteria: 50-200% of reference standard

TABLE 13

Stability of 150 mg/mL mAb-316P DP in PFS

| Storage | 0 | 5° C. at 6 | 25° C. at 6 | 45° C. at 28 |
|---|---|---|---|---|
| Appearance | Pass | Pass | Pass | Pass |
| Turbidity[1] | 0.00 | 0.00 | 0.00 | 0.02 |
| pH | 6.1 | 6.1 | 6.1 | 6.1 |
| % Total Recovered | 100 | 102 | 102 | 97 |
| % Native Recovered | 96.6 | 96.1 | 94.2 | 92.4 |
| % Aggregate | 2.4 | 2.6 | 3.2 | 4.3 |
| % Main Recovered | 58.4 | 58.5 | 45.7 | 35.8 |
| % Acidic Recovered | 31.8 | 31.3 | 42.1 | 50.9 |
| % Basic Recovered | 9.8 | 10.2 | 12.2 | 13.4 |

[1]Turbidity = change in OD at 405 nm relative to starting material.

TABLE 14

Stability of 175 mg/mL mAb-316P DP in PFS

| Storage | 0 | 5° C. at 6 | 25° C. at 6 | 45° C. at 28 |
|---|---|---|---|---|
| Appearance | Pass | Pass | Pass | Pass |
| Turbidity[1] | 0.00 | 0.00 | 0.02 | 0.04 |
| pH | 6.1 | 6.1 | 6.1 | 6.1 |
| % Total Recovered | 100 | 103 | 101 | 100 |
| % Native Recovered | 96.7 | 96.3 | 94.6 | 91.6 |
| % Aggregate | 2.3 | 2.4 | 3.0 | 5.4 |
| % Main Recovered | 59.1 | 59.7 | 47.1 | 37.7 |
| % Acidic Recovered | 31.2 | 30.6 | 40.6 | 48.2 |
| % Basic Recovered | 9.7 | 9.7 | 12.3 | 14.2 |

[1]Turbidity = change in OD at 405 nm relative to starting material.

TABLE 15

Compatibility of 150 mg/mL mAb-316P[1] for 14 Days at 40° C.

| | Storage | | | | | |
|---|---|---|---|---|---|---|
| | No Storage, Glass | Glass | Poly-carbonate | Poly-propylene | Poly-styrene | Stainless Steel |
| Turbidity[2] | 0.00 | 0.00 | 0.00 | 0.01 | 0.01 | 0.01 |
| pH | 6.0 | 6.1 | 6.0 | 6.0 | 6.0 | 6.0 |
| % Total Recovered | 100 | 97 | 104 | 99 | 105 | 104 |
| % Native Recovered | 97.4 | 95.9 | 95.8 | 95.7 | 95.7 | 95.5 |
| % Agg'ate Recvr'd | 1.7 | 2.5 | 2.6 | 2.7 | 2.6 | 2.7 |
| % Main Recovered | 53.3 | 45.8 | 45.8 | 44.7 | 45.6 | 45.1 |
| % Acidic Recovered | 26.9 | 33.0 | 32.9 | 33.8 | 33.0 | 33.5 |
| % Basic Recovered | 19.8 | 21.3 | 21.6 | 21.6 | 21.5 | 21.4 |

[1]10 mM Histidine, pH 6.0, 0.2% Polysorbate 20, 10% Sucrose, and 150 mg/mL mAb
[2]Turbidity = OD at 405 nm relative to the starting material.

TABLE 16

Compatibility of 175 mg/mL mAb-316P[1] for 14 Days at 40° C.

| | Storage | | | | | |
|---|---|---|---|---|---|---|
| | No Storage, Glass | Glass | Poly-carbonate | Poly-propylene | Poly-styrene | Stainless Steel |
| Turbidity[3] | 0.00 | 0.00 | 0.00 | 0.00 | 0.00 | 0.01 |
| pH | 6.1 | 6.1 | 6.1 | 6.0 | 6.1 | 6.1 |
| % Total Recovered | 100 | 98 | 104 | 100 | 105 | 98 |
| % Native Recovered | 96.6 | 95.3 | 95.2 | 95.1 | 95.2 | 94.9 |
| % Agg'ate Recvr'd | 2.4 | 3.0 | 3.1 | 3.2 | 3.1 | 3.3 |
| % Main Recovered | 57.7 | 51.3 | 51.0 | 50.6 | 51.0 | 50.4 |
| % Acidic Recovered | 30.0 | 34.5 | 34.5 | 35.0 | 34.5 | 35.2 |
| % Basic Recovered | 12.3 | 14.2 | 14.5 | 14.4 | 14.4 | 14.4 |

[1]10 mM Histidine, pH 6.0, 0.01% Polysorbate 20, 5% Sucrose, 50 mM arginine, and 175 mg/mL mAb
[2]Turbidity = OD at 405 nm relative to the starting material.

TABLE 17

Charge Heterogeneity of mAb-316P by cIEF

| Peak No. | Lot 1 | | Lot 2 | | Lot 1:Lot 2 (1:1 mix) | |
|---|---|---|---|---|---|---|
| | pI | Peak Area, % | pI | Peak Area, % | pI | Peak Area, % |
| 1 | 7.99 (0.01) | 0.8 (0.1) | 7.99 (0.01) | 0.8 (0.0) | 7.98 (0.01) | 0.7 (0.1) |
| 2 | 8.15 (0.00) | 2.6 (0.1) | 8.15 (0.00) | 2.6 (0.1) | 8.14 (0.01) | 2.6 (0.1) |
| 3 | 8.29 (0.00) | 6.9 (0.1) | 8.29 (0.00) | 7.0 (0.0) | 8.28 (0.01) | 6.9 (0.1) |
| 4 | 8.42 (0.00) | 18.4 (0.2) | 8.42 (0.00) | 18.6 (0.2) | 8.42 (0.01) | 18.5 (0.1) |
| 5 | 8.54 (0.01) | 66.4 (0.3) | 8.55 (0.00) | 68.0 (0.3) | 8.54 (0.00) | 67.3 (0.1) |
| 6 | 8.65 (0.00) | 4.0 (0.1) | 8.65 (0.00) | 2.8 (0.1) | 8.64 (0.01) | 3.4 (0.0) |
| 7 | 8.82 (0.00) | 0.9 (0.1) | 8.81 (0.00) | 0.3 (0.1) | 8.81 (0.01) | 0.6 (0.1) |

TABLE 18 mAb-316P glycosylated peptides

| Peak No. | Heavy Chain Fragment | Observed mass (Da) Lot 1 | Lot 2 | Comments |
|---|---|---|---|---|
| 15a | 294-302 | 2957.15 | 2957.19 | (Fuc)$_1$(GlcNAc)$_2$(Man)$_3$(GlcNAc)$_2$(Gal)$_2$ |
|  | 294-302 | 2795.11 | 2795.11 | (Fuc)$_1$(GlcNAc)$_2$(Man)$_3$(GlcNAc)$_2$(Gal)$_1$ |
|  | 294-302 | 2404.94 | 2404.94 | (GlcNAc)$_2$(Man)$_5$ |
|  | 294-302 | 2592.02 | 2591.96 | (Fuc)$_1$(GlcNAc)$_2$(Man)$_3$(GlcNAc)$_1$(Gal)$_1$ |
|  | 294-302 | 2267.94 | 2267.92 | (Fuc)$_1$(GlcNAc)$_2$(Man)$_2$(GlcNAc)$_1$ |
|  | 294-302 | 2121.82 | 2121.80 | (GlcNAc)$_2$(Man)$_2$(GlcNAc)$_1$ |
| 15b | 294-302 | 2283.91 | 2283.91 | (GlcNAc)$_2$(Man)$_3$(GlcNAc)$_1$ |
|  | 294-302 | 2429.98 | 2429.98 | (Fuc)$_1$(GlcNAc)$_2$(Man)$_3$(GlcNAc)$_1$ |
|  | 294-302 | 2486.99 | 2486.97 | (GlcNAc)$_2$(Man)$_3$(GlcNAc)$_2$ |
|  | 294-302 | 2633.05 | 2633.06 | (Fuc)$_1$(GlcNAc)$_2$(Man)$_3$(GlcNAc)$_2$ |
| 16 | 294-302 | 1188.52 | 1188.53 | non-glycosylated NST site |
| 17a | 290-302 | 3439.44 | 3439.44 | (Fuc)$_1$(GlcNAc)$_2$(Man)$_3$(GlcNAc)$_2$(Gal)$_2$ |
|  | 290-302 | 3278.40 | 3277.35 | (Fuc)$_1$(GlcNAc)$_2$(Man)$_3$(GlcNAc)$_2$(Gal)$_1$ |
|  | 290-302 | 2887.20 | 2887.26 | (GlcNAc)$_2$(Man)$_5$ |
| 17b | 290-302 | 2766.24 | 2766.21 | (GlcNAc)$_2$(Man)$_3$(GlcNAc)$_1$ |
|  | 290-302 | 2969.34 | 2969.25 | (GlcNAc)$_2$(Man)$_3$(GlcNAc)$_2$ |
|  | 290-302 | 2912.28 | 2912.25 | (Fuc)$_1$(GlcNAc)$_2$(Man)$_3$(GlcNAc)$_1$ |
|  | 290-302 | 3115.32 | 3115.35 | (Fuc)$_1$(GlcNAc)$_2$(Man)$_3$(GlcNAc)$_2$ |

TABLE 19

Integrated Peak Areas of Glycans Identified by Capillary Electrophoresis

|  | Lot 1 Peak Area[a], % | Lot 2 Peak Area, % | 1:1 lot mixture Peak Area, % | Glycan Identity [1] |
|---|---|---|---|---|
| 1 | 8.6 (0.2) | 6.8 (0.1) | 7.6 (0.2) | G0-Fuc |
| 2 | 1.8 (0.0) | 2.9 (0.1) | 2.3 (0.1) | Man5 |
| 3 | 0.7 (0.0) | 0.5 (0.0) | 0.6 (0.0) | Minor peak is unidentified |
| 4 | Below LOQ | Below LOQ | Below LOQ | Minor peak is unidentified |
| 5 | Below LOQ | Below LOQ | Below LOQ | Minor peak is unidentified |
| 6 | 34.4 (0.1) | 45.8 (0.2) | 40.4 (0.2) | G0 |
| 7 | 1.5 (0.0) | 0.7 (0.0) | 1.1 (0.0) | Minor peak is unidentified |
| 8 | Below LOQ | 0.9 (0.0) | 0.6 (0.0) | Minor peak is unidentified |
| 9 | Below LOQ | 0.7 (0.0) | 0.6 (0.0) | Minor peak is unidentified |
| 10 | 29.5 (0.1) | 24.7 (0.0) | 27.0 (0.1) | G1(1-6) |
| 11 | 10.1 (0.1) | 8.6 (0.0) | 9.3 (0.1) | G1(1-3) and/or G2-Fuc |
| 12 | Below LOQ | Below LOQ | Below LOQ | Minor peak is unidentified |
| 13 | Below LOQ | Below LOQ | Below LOQ | Minor peak is unidentified |
| 14 | 11.7 (0.0) | 7.1 (0.1) | 9.4 (0.2) | G2 |

[1] G#-fuc and G# refer to non-fucosylated and fucosylated glycans, respectively. The symbol # refers to 0, 1, or 2.
LOQ = Limit of Quantification.

What is claimed is:

1. A pre-filled pen delivery device comprising a liquid pharmaceutical formulation, wherein the liquid pharmaceutical formulation consists of:
    (a) 50±7.5 mg/mL to 250±37.5 mg/mL of an antibody or antigen-binding fragment thereof that specifically binds human proprotein convertase subtilisin kexin-9 (PCSK9), wherein the antibody or antigen-binding fragment comprises a heavy chain variable domain (HCVD) comprising SEQ ID NO:1, and a light chain variable domain (LCVD) comprising SEQ ID NO:5;
    (b) 5±0.75 mM to 10±1.5 mM histidine, pH 6.0±0.3;
    (c) 0.01±0.0015% w/v polysorbate 20; and
    (d) 10±1.5% w/v sucrose.

2. A pre-filled pen delivery device comprising a liquid pharmaceutical formulation, wherein the liquid pharmaceutical formulation consists of:
    (a) 75 mg/mL of an antibody or antigen-binding fragment thereof that specifically binds human proprotein convertase subtilisin kexin-9 (PCSK9), wherein the antibody or antigen-binding fragment comprises a heavy chain variable domain (HCVD) comprising SEQ ID NO:1, and a light chain variable domain (LCVD) comprising SEQ ID NO:5;
    (b) 8±1.2 mM histidine, pH 6.0±0.3;
    (c) 0.01±0.0015% w/v polysorbate 20; and
    (d) 10±1.5% w/v sucrose.

3. A pre-filled pen delivery device comprising a liquid pharmaceutical formulation, wherein the liquid pharmaceutical formulation consists of:
    (a) 150 mg/mL of an antibody or antigen-binding fragment thereof that specifically binds human proprotein convertase subtilisin kexin-9 (PCSK9), wherein the antibody or antigen-binding fragment comprises a heavy chain variable domain (HCVD) comprising SEQ ID NO:1, and a light chain variable domain (LCVD) comprising SEQ ID NO:5;
    (b) 6±0.9 mM histidine (pH 6.0±0.3);
    (c) 0.01±0.0015% w/v polysorbate 20; and
    (d) 10±1.5% w/v sucrose.

* * * * *